(12) United States Patent
Judson et al.

(10) Patent No.: US 11,957,882 B2
(45) Date of Patent: Apr. 16, 2024

(54) MEDICAL DELIVERY DEVICE WITH AXIALLY EXPANDABLE DRIVE RIBBON

(71) Applicant: Eli Lilly and Company, Indianapolis, IN (US)

(72) Inventors: Jared Alden Judson, Medford, MA (US); Timothy Lee Moulton, Newport, RI (US); Russell Wayne Perkins, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 806 days.

(21) Appl. No.: 16/764,638

(22) PCT Filed: Nov. 30, 2018

(86) PCT No.: PCT/US2018/063201
§ 371 (c)(1),
(2) Date: May 15, 2020

(87) PCT Pub. No.: WO2019/112886
PCT Pub. Date: Jun. 13, 2019

(65) Prior Publication Data
US 2021/0379289 A1    Dec. 9, 2021

Related U.S. Application Data

(60) Provisional application No. 62/596,167, filed on Dec. 8, 2017.

(51) Int. Cl.
*A61M 5/315* (2006.01)
*A61M 5/24* (2006.01)
*A61M 5/31* (2006.01)

(52) U.S. Cl.
CPC .......... *A61M 5/31511* (2013.01); *A61M 5/24* (2013.01); *A61M 5/31501* (2013.01);
(Continued)

(58) Field of Classification Search
CPC ......... A61M 2005/31518; A61M 2005/14506; A61M 2005/3152; A61M 5/1454;
(Continued)

(56) References Cited

U.S. PATENT DOCUMENTS

| 4,313,439 A | 2/1982 | Babb et al. |
| 4,875,660 A | 10/1989 | Gagnon et al. |

(Continued)

FOREIGN PATENT DOCUMENTS

| EP | 2238997 | 10/2010 |
| EP | 2698180 | 2/2014 |

(Continued)

OTHER PUBLICATIONS

Patent Cooperation Treaty International Search Report pertaining to International Application No. PCT/US2018/063201; International Filing Date: Nov. 30, 2018; dated Mar. 4, 2019.
(Continued)

*Primary Examiner* — Robert J Utama
*Assistant Examiner* — Leah J Swanson
(74) *Attorney, Agent, or Firm* — M. Daniel Spillman

(57) ABSTRACT

A medication delivery device usable with a medication container wherein advancement of a piston within the container expels medication. The device includes a housing and a drive assembly. The drive assembly includes a drive ribbon having distal and proximal edge sections. The drive ribbon has a retracted configuration defining a spiral and an extended configuration defining a helix. The drive ribbon is movable from the retracted configuration to the extended configuration with the movement defining a drive axis and advancing the piston. In some embodiments, the drive ribbon may not rotate as the drive ribbon is advanced while in other embodiments, the ribbon does rotate. Disclosed drive assemblies include manually driven assemblies, spring
(Continued)

driven assemblies and motor driven assemblies. The container may be replaceable to allow for reuse of the device. In some embodiments, replaceable cartridges which include both the medication container and the drive ribbon are employed.

29 Claims, 54 Drawing Sheets

(52) U.S. Cl.
CPC . *A61M 5/31585* (2013.01); *A61M 2005/3125* (2013.01); *A61M 2005/31518* (2013.01); *A61M 2005/31588* (2013.01)

(58) Field of Classification Search
CPC .......... A61M 5/31511; A61M 5/31501; A61M 5/315; A61M 5/31565; A61M 5/31576; A61M 5/31578; A61M 5/3158; A61M 5/31588; A61M 5/24; A61M 5/31585; A61M 5/31551; A61M 5/31581; A61M 5/178; A61M 2005/31588; A61M 2205/52; A61M 2205/6081; A61M 2205/502; A61M 2205/3379; A61M 2005/3125; A61M 5/2422
See application file for complete search history.

(56) References Cited

U.S. PATENT DOCUMENTS

| | | | |
|---|---|---|---|
| 4,908,017 A * | 3/1990 | Howson | A61M 5/1452 604/154 |
| 5,178,609 A | 1/1993 | Ishikawa | |
| 5,478,316 A | 12/1995 | Bitdinger et al. | |
| 5,637,095 A | 6/1997 | Nason et al. | |
| 6,537,251 B2 | 3/2003 | Klitmose | |
| 6,547,216 B1 | 4/2003 | Bouchard et al. | |
| 7,066,909 B1 | 6/2006 | Peter et al. | |
| 7,213,796 B2 | 5/2007 | Laforest | |
| 7,220,248 B2 | 5/2007 | Mernøe | |
| 7,500,959 B2 | 3/2009 | Munk | |
| 8,105,279 B2 * | 1/2012 | Mernoe | A61M 5/14244 604/890.1 |
| 8,517,988 B2 | 8/2013 | Smith | |
| 8,517,991 B2 * | 8/2013 | Clemente | B05C 17/0103 604/154 |
| 9,289,556 B2 | 3/2016 | Manke et al. | |
| 10,149,943 B2 | 12/2018 | Bar-El et al. | |
| 10,898,652 B2 | 1/2021 | Judson et al. | |
| 2001/0023637 A1 | 9/2001 | Kitmose et al. | |
| 2002/0091358 A1 | 7/2002 | Klitmose | |
| 2004/0045555 A1 | 3/2004 | Nelson et al. | |
| 2006/0276753 A1 | 12/2006 | Kronestedt et al. | |
| 2009/0069785 A1 * | 3/2009 | Miller | A61M 5/172 604/151 |
| 2010/0094253 A1 | 4/2010 | Boyd et al. | |
| 2010/0249706 A1 | 9/2010 | Clemente | |
| 2011/0118694 A1 * | 5/2011 | Yodfat | A61M 5/172 604/93.01 |
| 2011/0184351 A1 * | 7/2011 | Holmqvist | A61M 5/2033 604/187 |
| 2011/0226264 A1 | 9/2011 | Friedman et al. | |
| 2011/0306929 A1 | 12/2011 | Levesque et al. | |
| 2012/0010568 A1 | 1/2012 | Smith | |
| 2012/0041387 A1 | 2/2012 | Brüggemann et al. | |
| 2012/0172817 A1 | 7/2012 | Brüggemann et al. | |
| 2014/0214001 A1 | 7/2014 | Mortazavi | |
| 2015/0290392 A1 | 10/2015 | Henderson et al. | |
| 2016/0158453 A1 | 6/2016 | Oakley | |
| 2017/0049968 A1 | 2/2017 | Choi | |
| 2017/0296750 A1 | 10/2017 | Morris | |

FOREIGN PATENT DOCUMENTS

| | | |
|---|---|---|
| KR | 20090082490 | 7/2009 |
| KR | 20170065622 | 6/2017 |
| WO | 05077441 | 8/2005 |
| WO | 2006066963 | 6/2006 |
| WO | 2010037759 | 4/2010 |
| WO | 2014138506 | 9/2014 |
| WO | 2017099894 | 6/2017 |
| WO | 2017139741 | 8/2017 |
| WO | 2017165154 | 9/2017 |

OTHER PUBLICATIONS

Patent Cooperation Treaty Written Opinion of the International Searching Authority pertaining to International Application No. PCT/US2018/063201; International Filing Date: Nov. 30, 2018; dated Mar. 4, 2019.

"Paco Spiralift," webpage <http://www.pacospiralift.com>, 1 page, Mar. 8, 2016, retrieved from Internet Archive Wayback Machine <http://web.archive.org/web/20160308060858/http://pacospiralift.com/> on May 12, 2023).

* cited by examiner

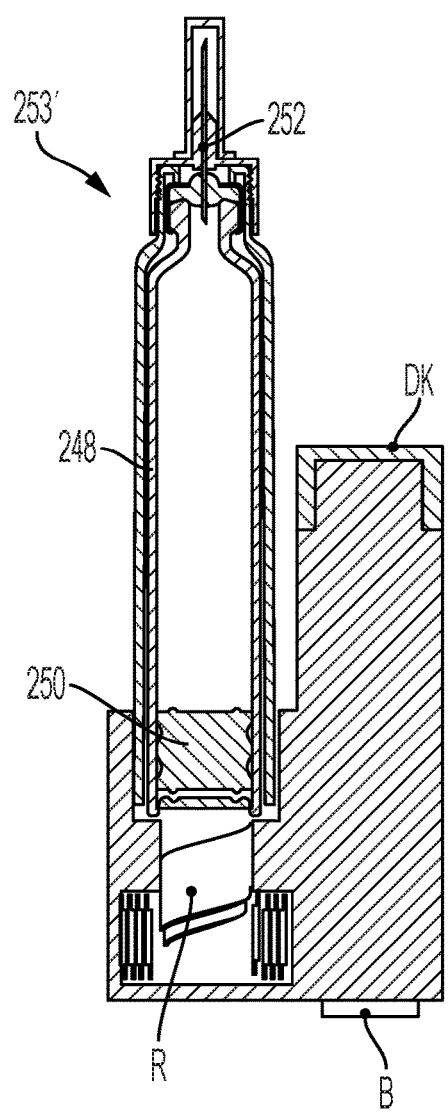
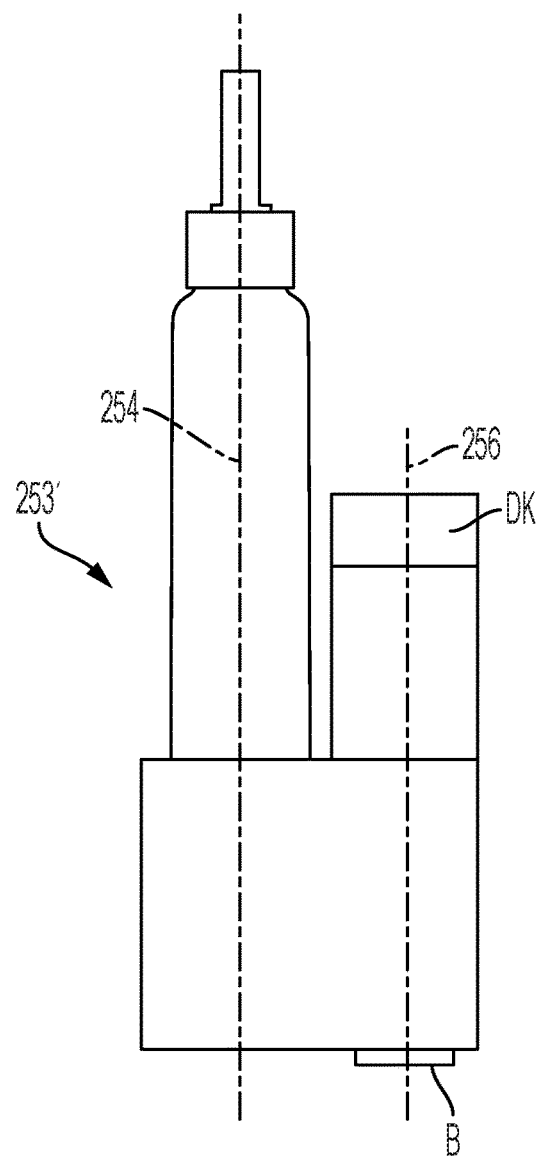
Fig. 52    Fig. 53
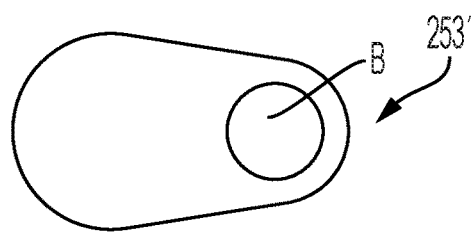
Fig. 54

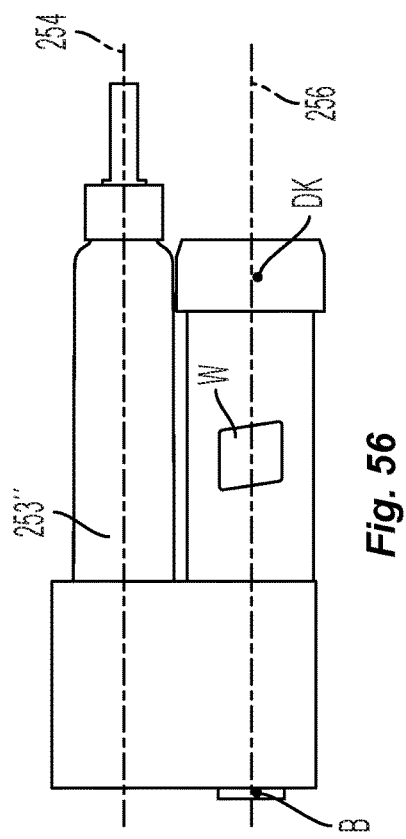
Fig. 55
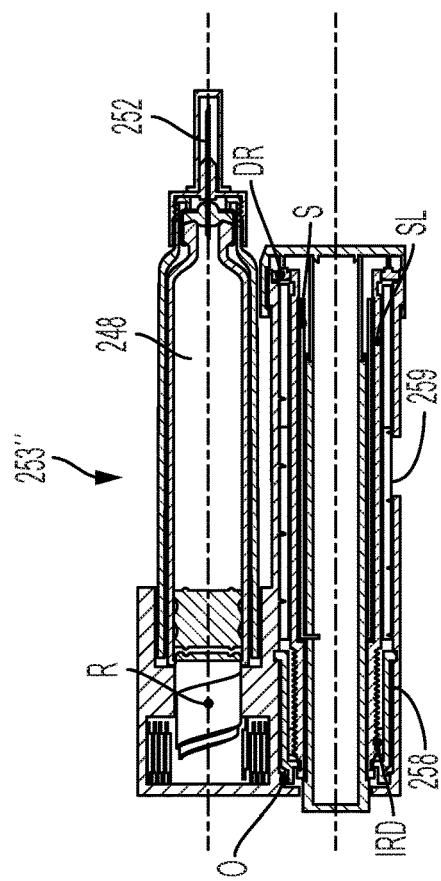
Fig. 56
Fig. 57
Fig. 58
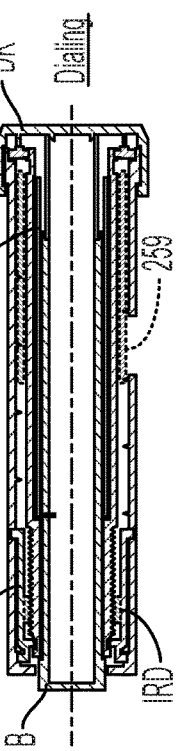
Fig. 59
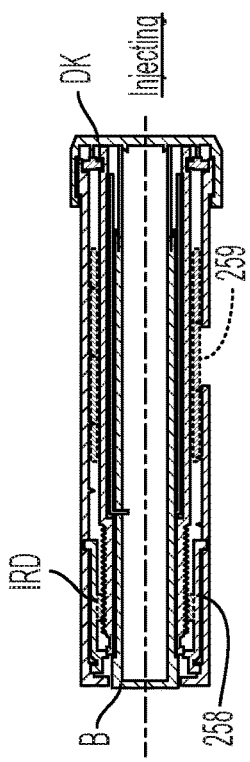
Fig. 60

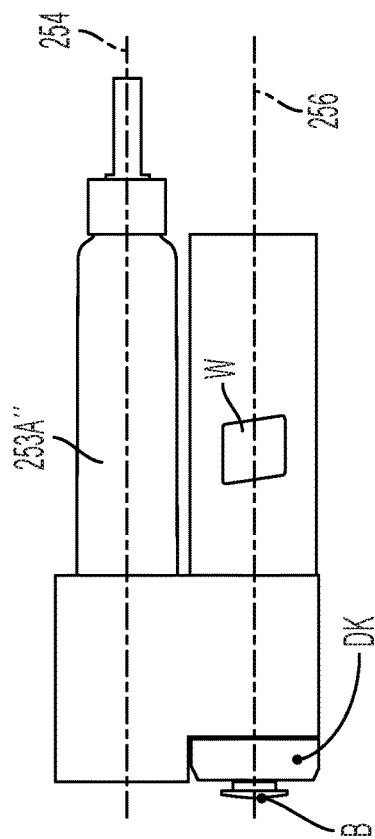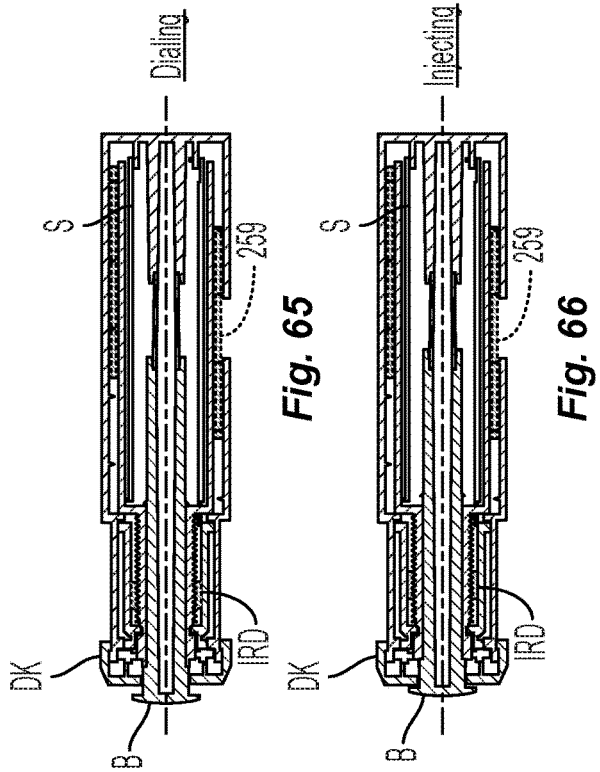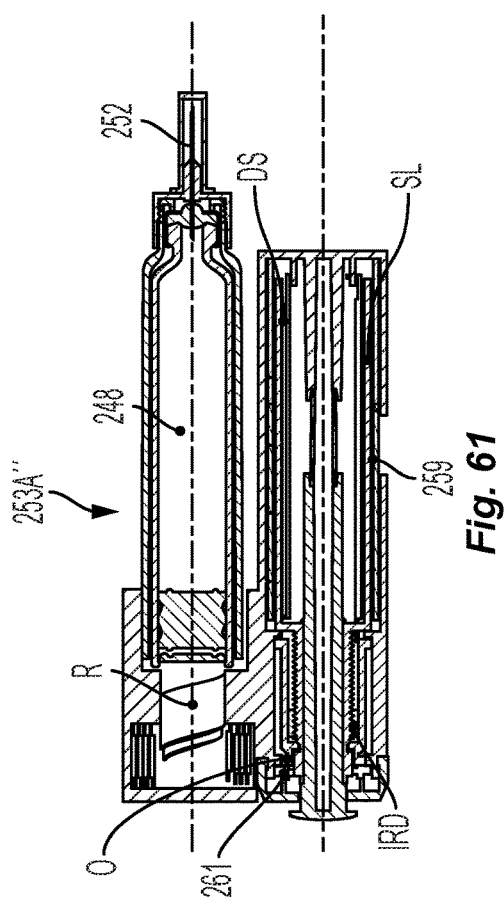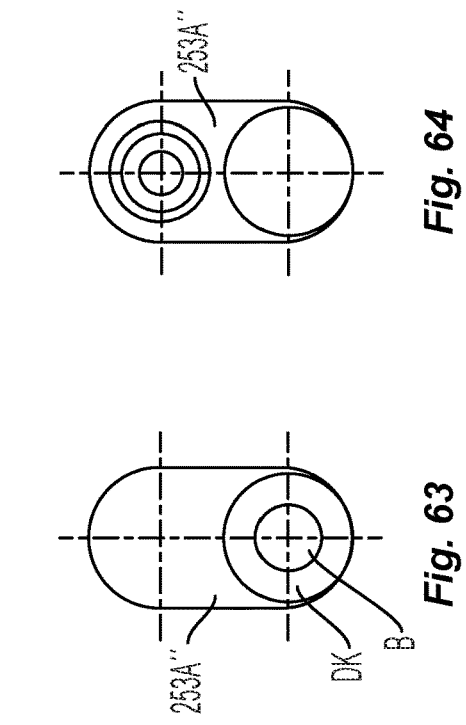
Fig. 61
Fig. 62
Fig. 63
Fig. 64
Fig. 65
Fig. 66

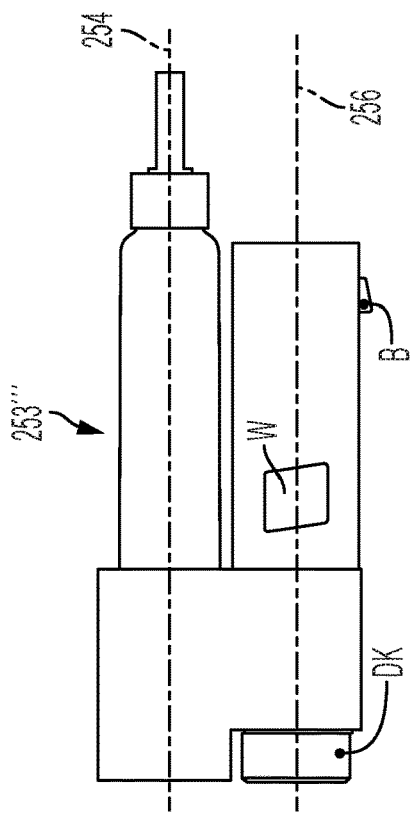
*Fig. 67*
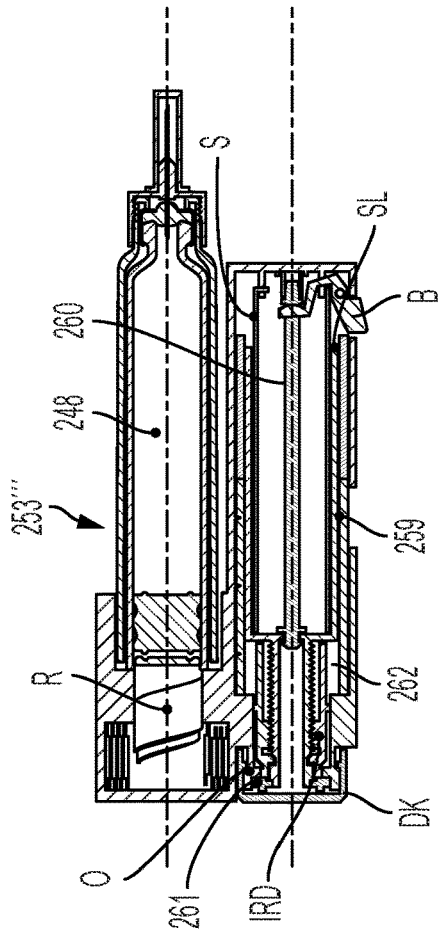
*Fig. 68*
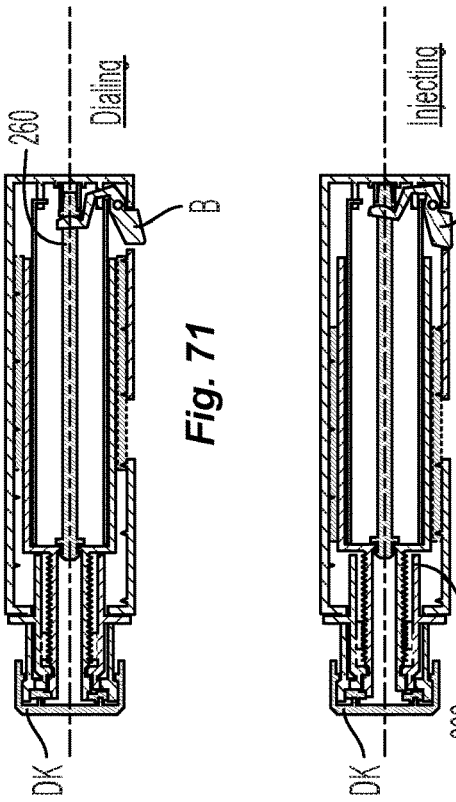
*Fig. 71*
*Fig. 72*
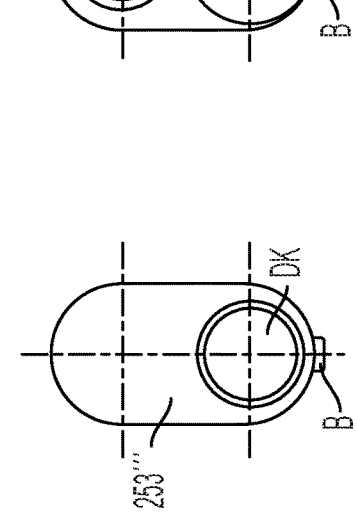
*Fig. 70*
*Fig. 69*

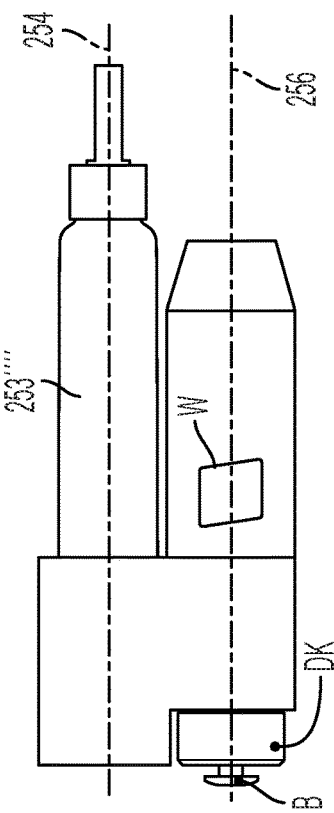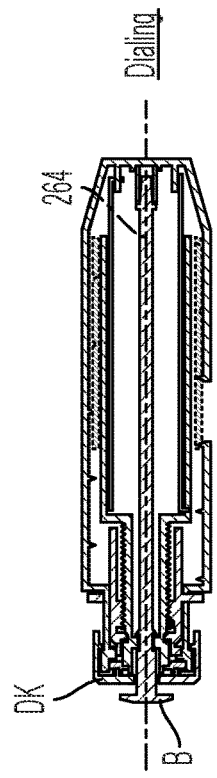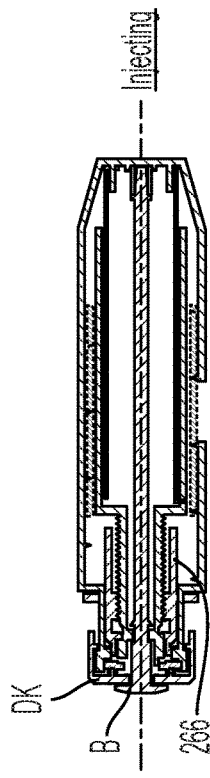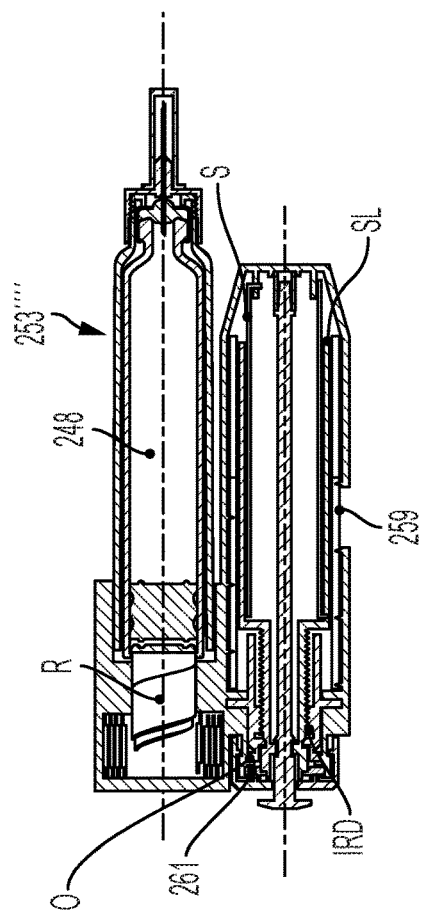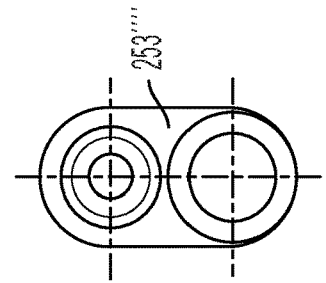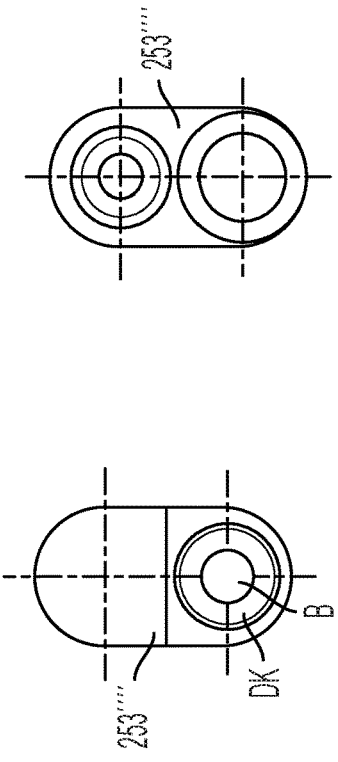

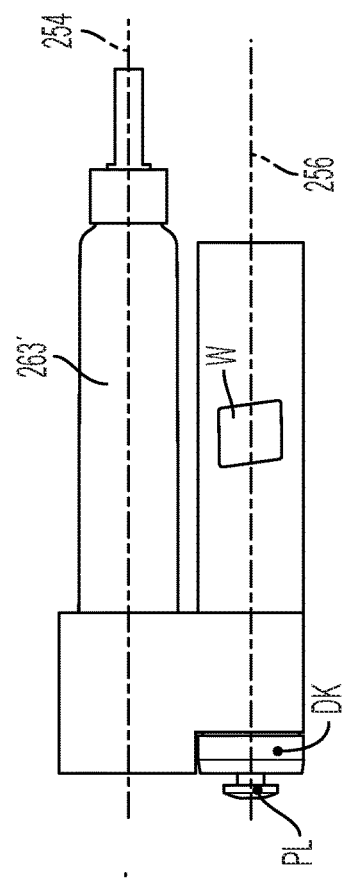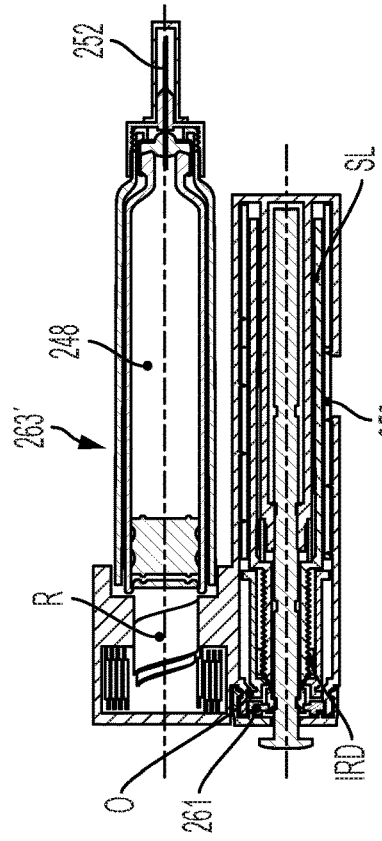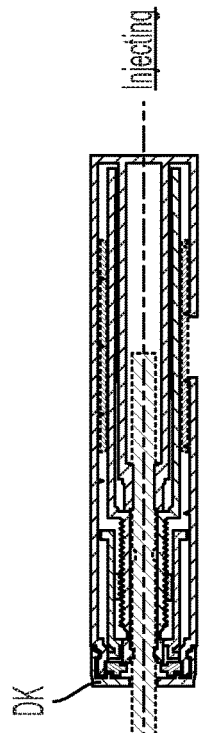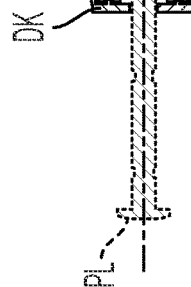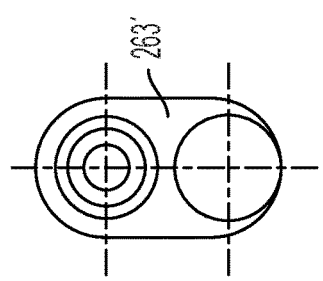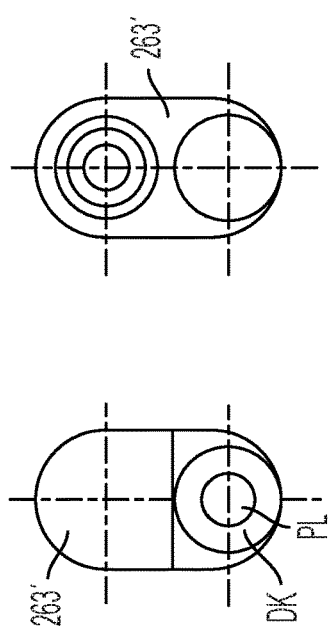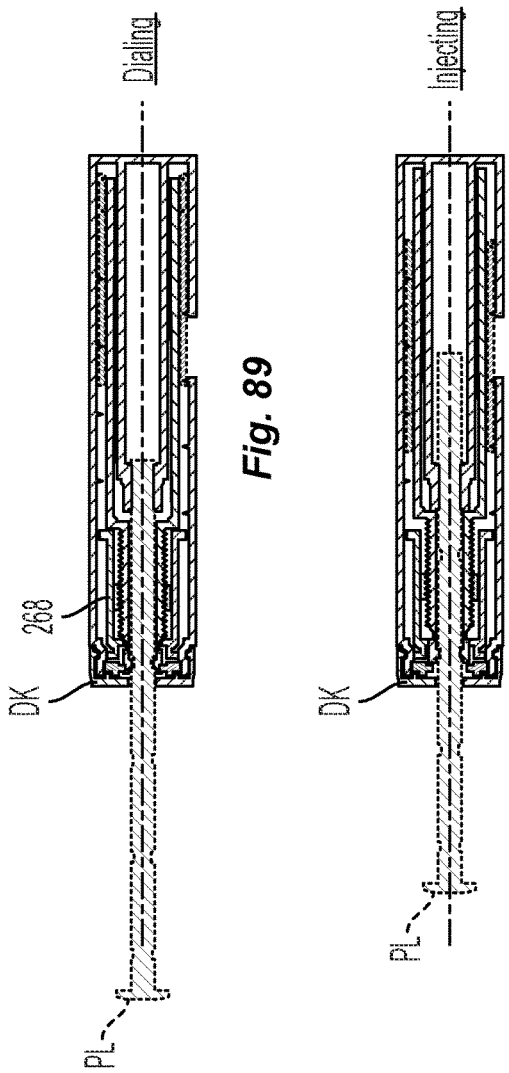
*Fig. 86*
*Fig. 89*
*Fig. 90*
*Fig. 85*
*Fig. 88*
*Fig. 87*

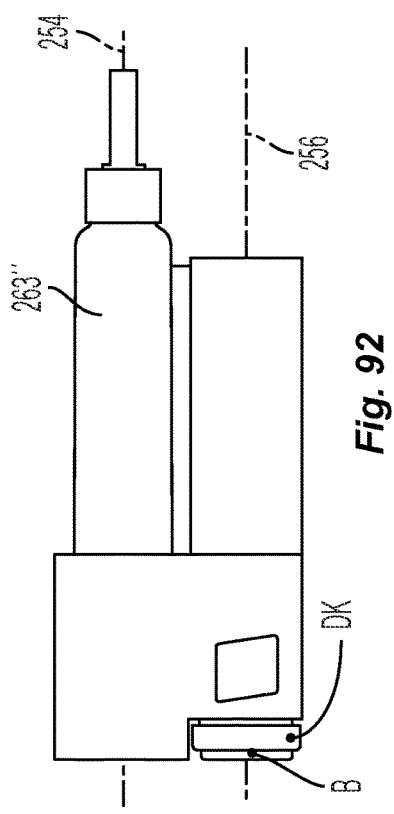
*Fig. 92*
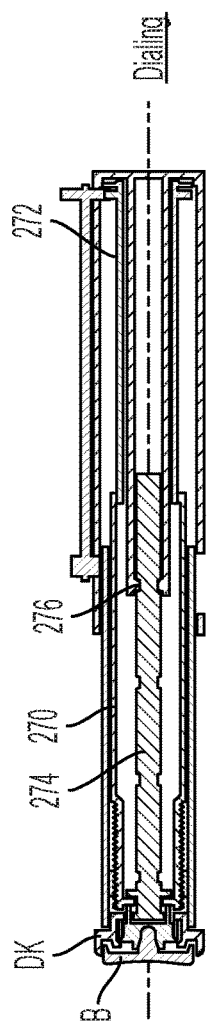
*Fig. 95*
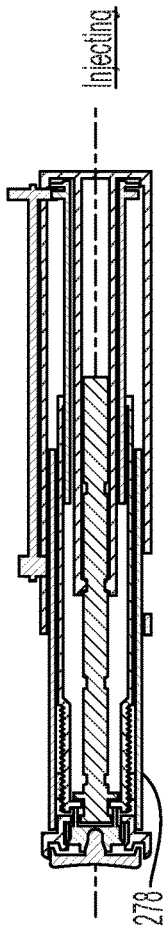
*Fig. 96*
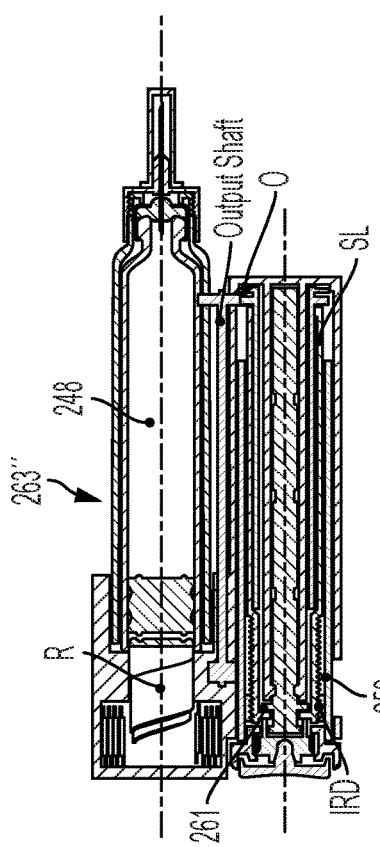
*Fig. 91*
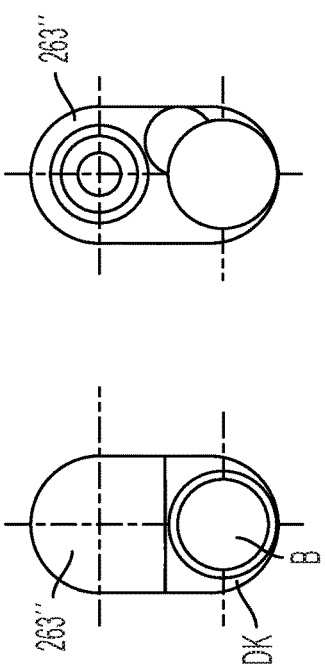
*Fig. 94*
*Fig. 93*

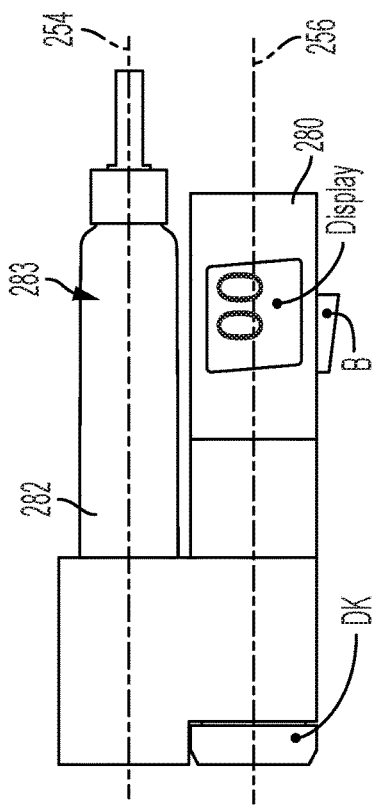
*Fig. 97*
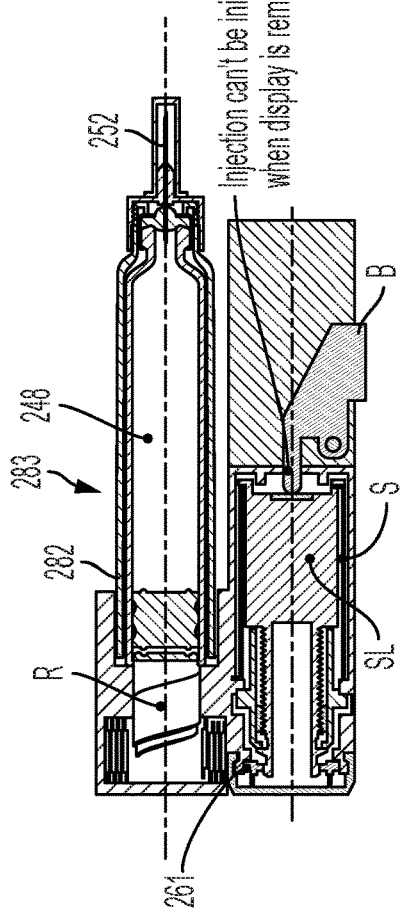
*Fig. 98*
*Fig. 99*
*Fig. 100*
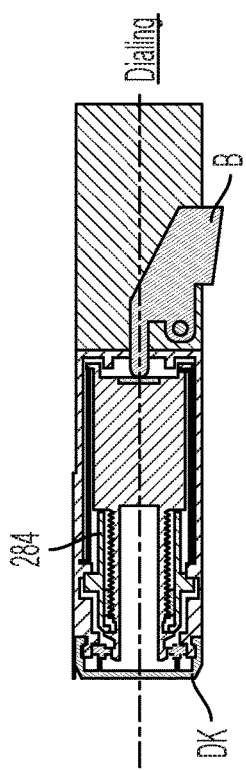
*Fig. 101*
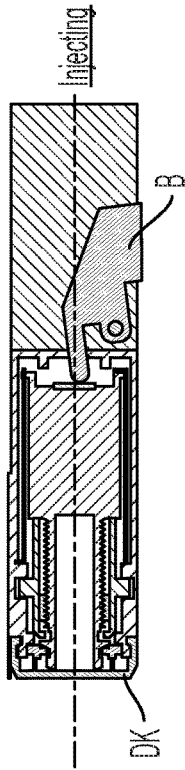
*Fig. 102*

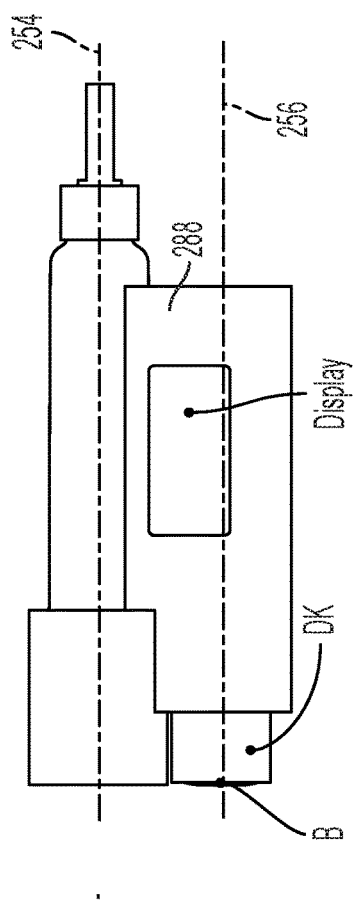
*Fig. 104*
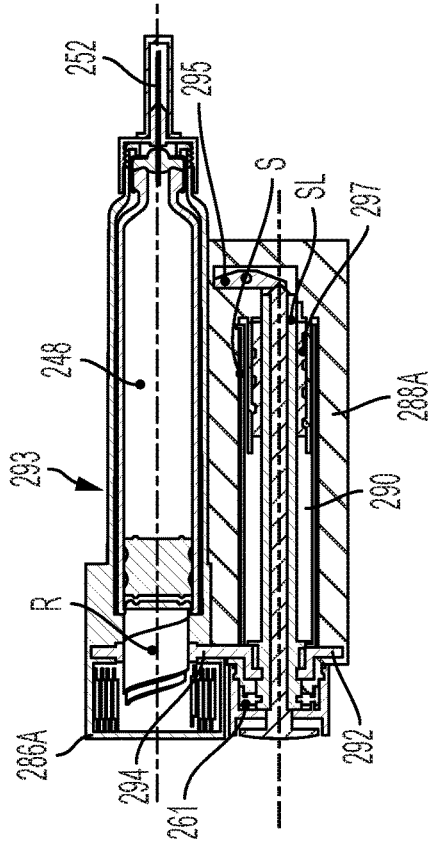
*Fig. 103*
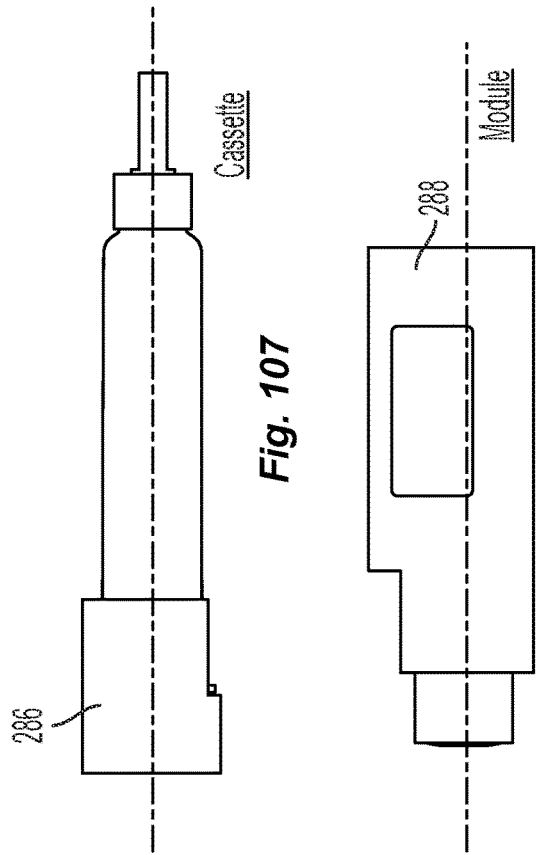
*Fig. 107*
*Fig. 108*
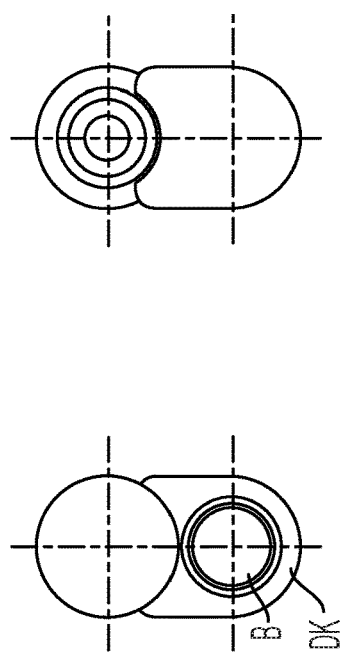
*Fig. 106*
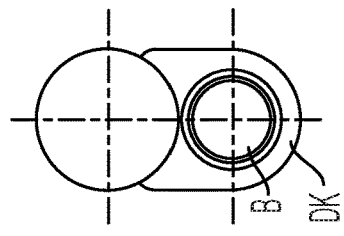
*Fig. 105*

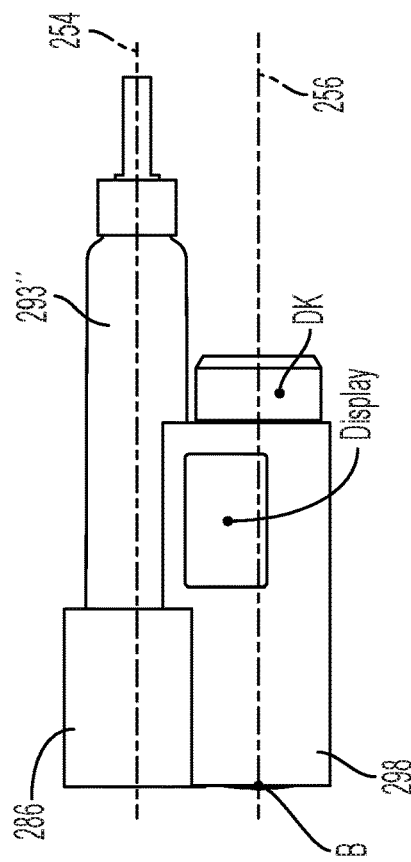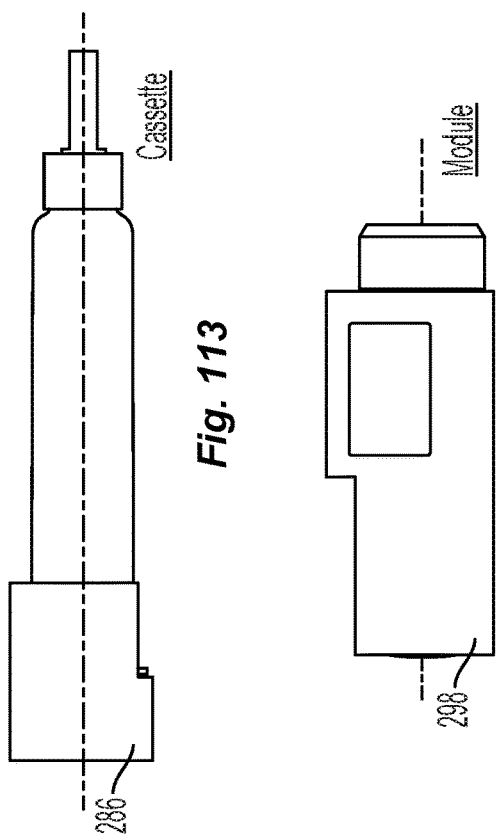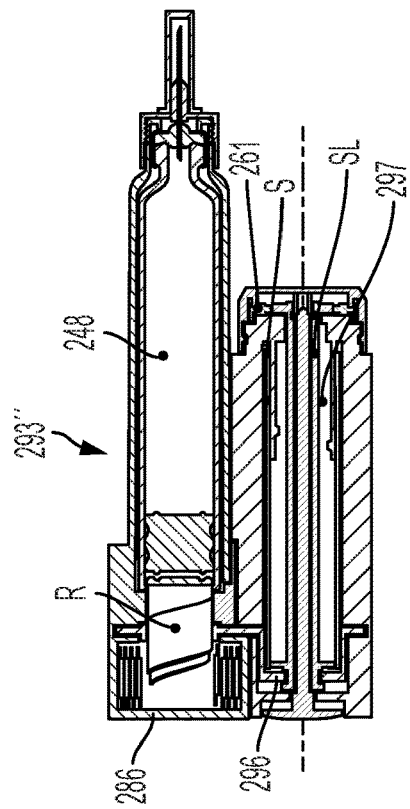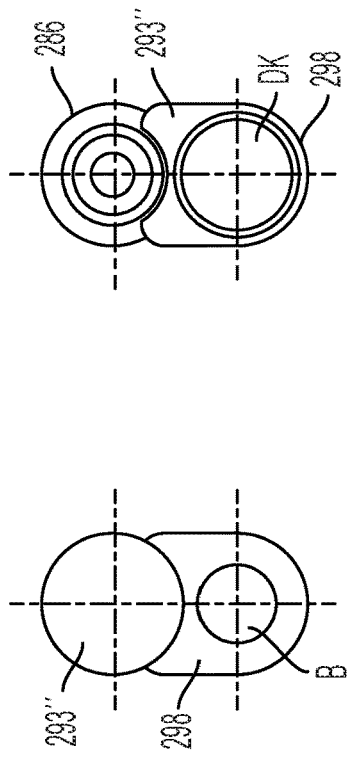
Fig. 109
Fig. 110
Fig. 111
Fig. 112
Fig. 113
Fig. 114

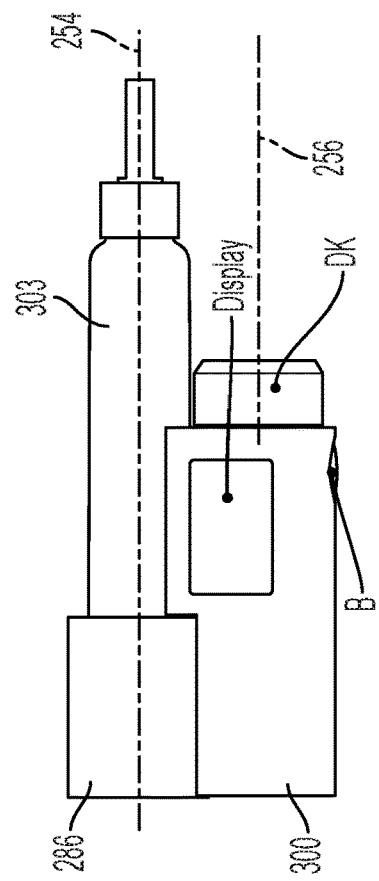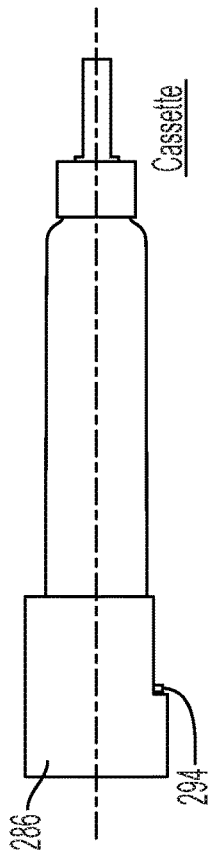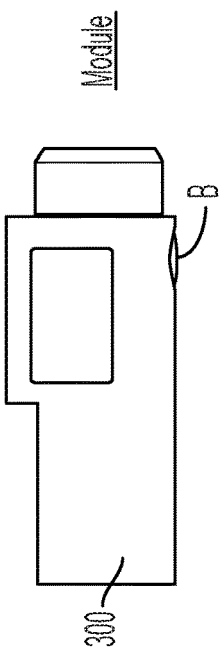
*Fig. 116* *Fig. 119* *Fig. 120*
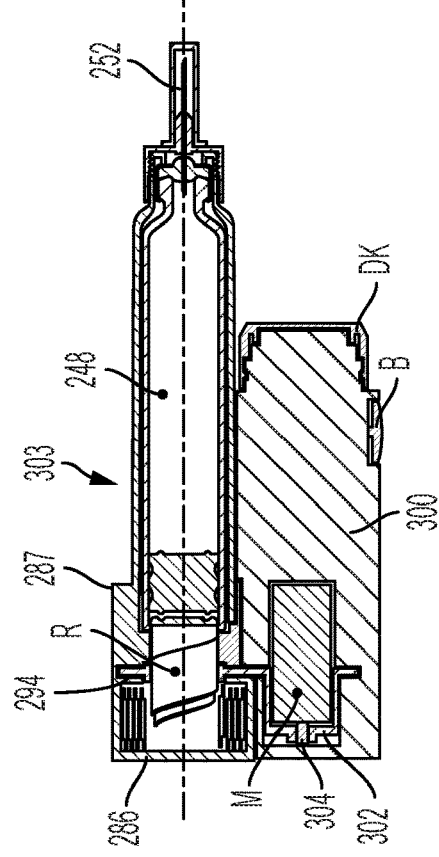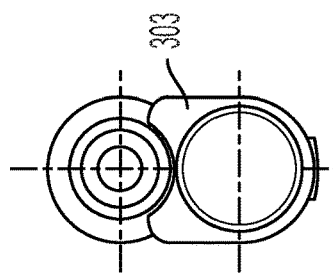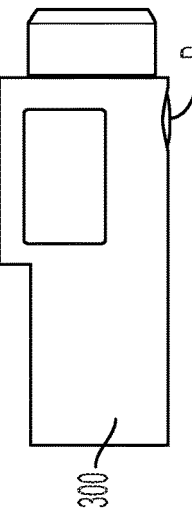
*Fig. 115* *Fig. 118* *Fig. 117*

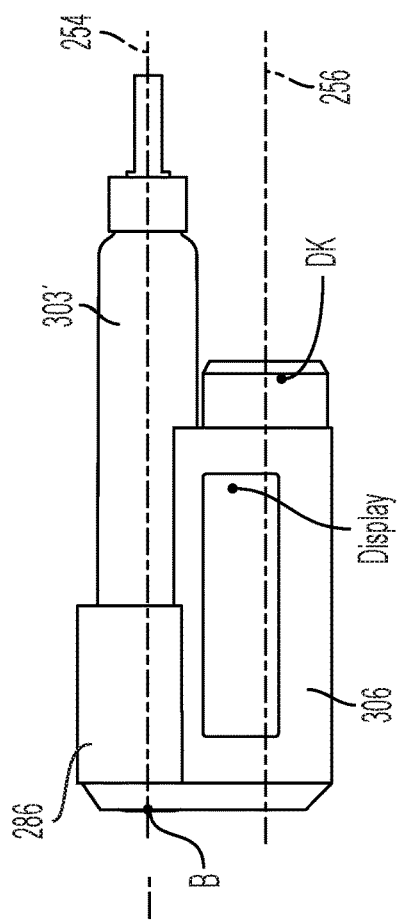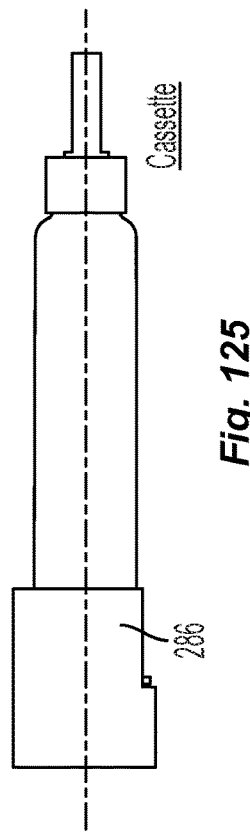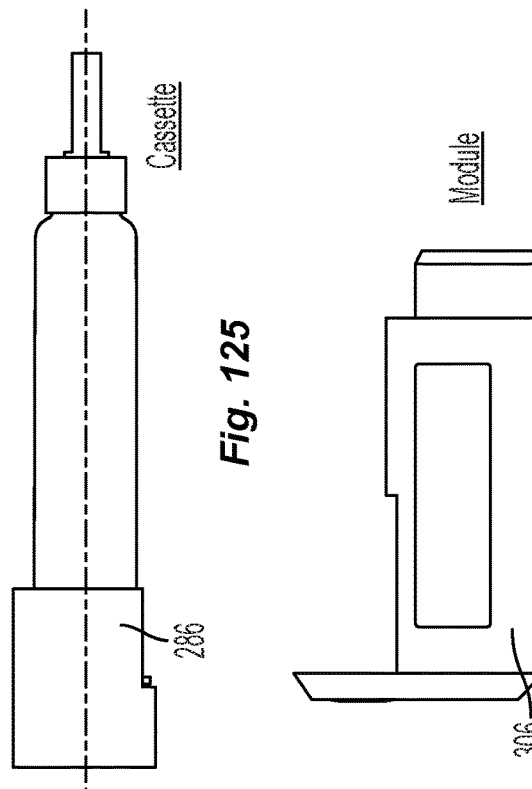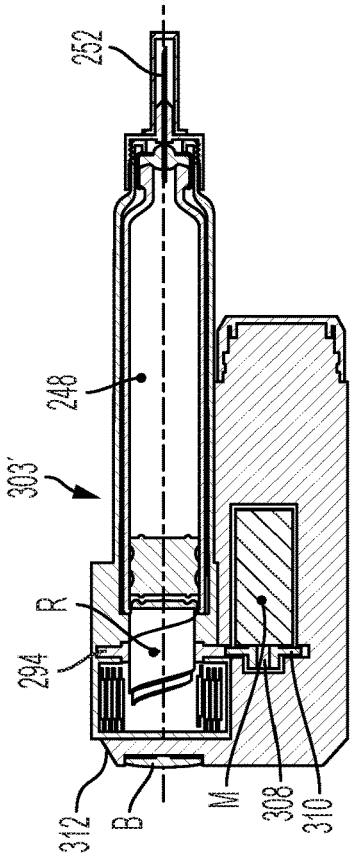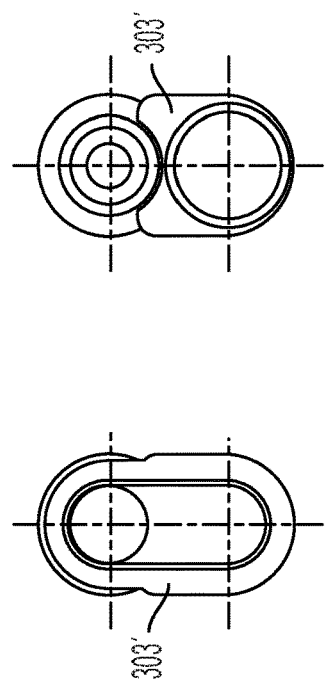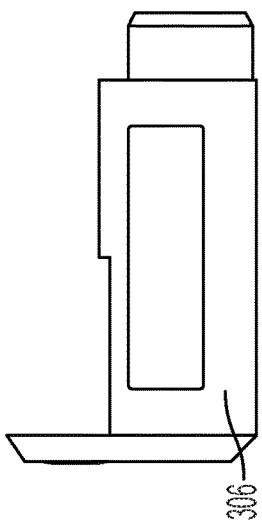
*Fig. 121*
*Fig. 122*
*Fig. 125*
*Fig. 126*
*Fig. 123*
*Fig. 124*

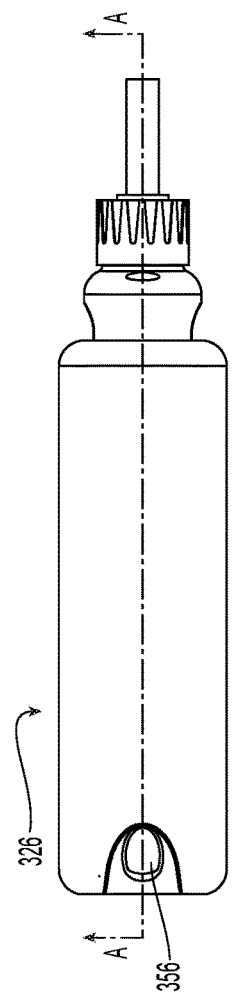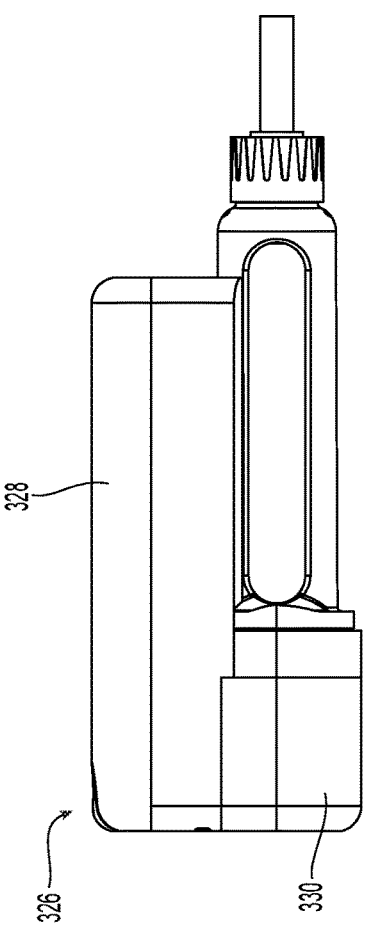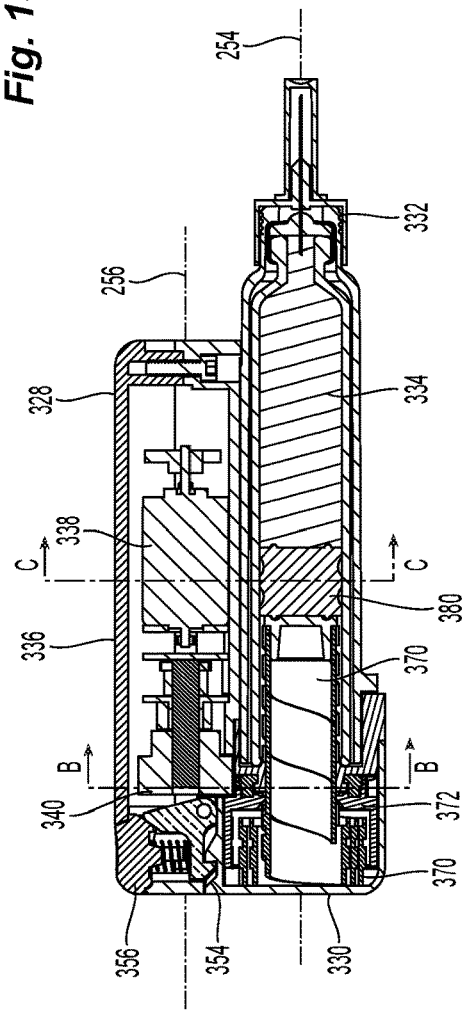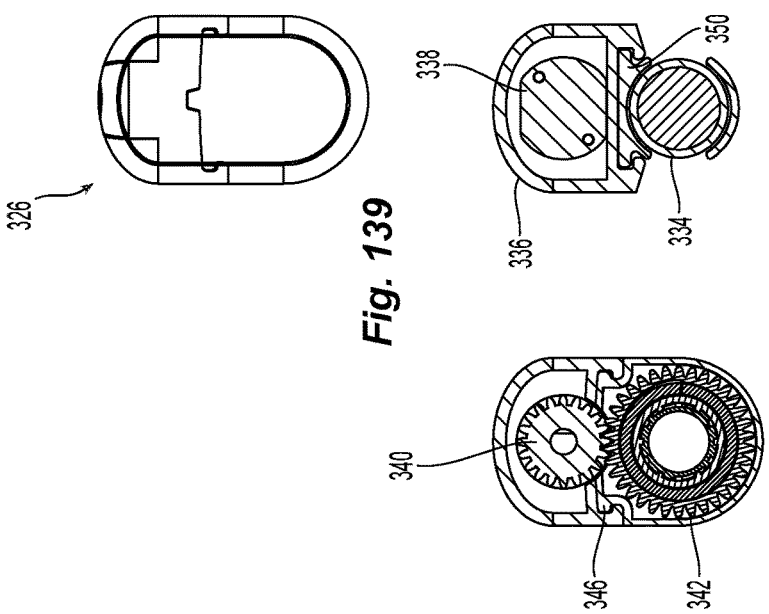

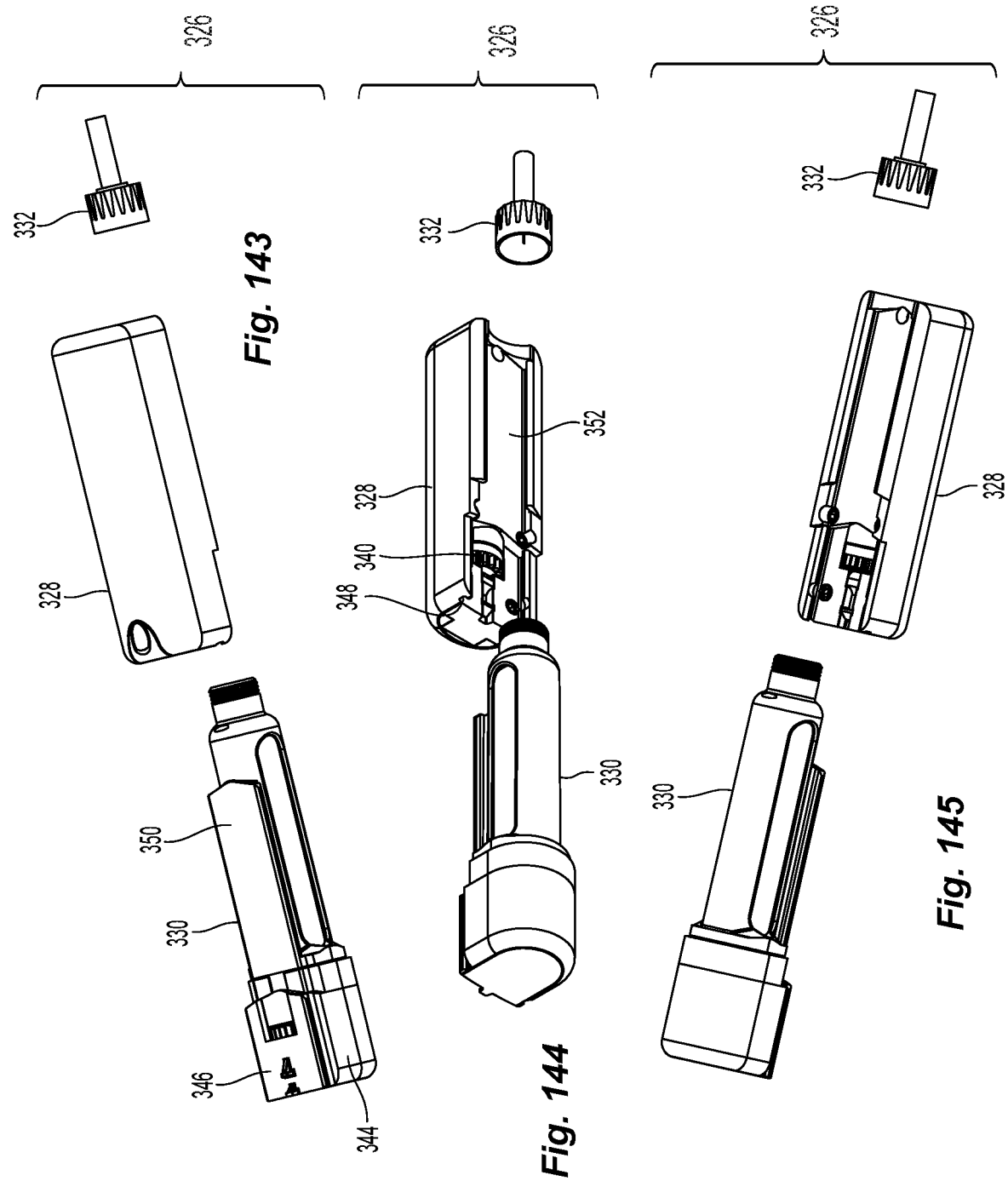

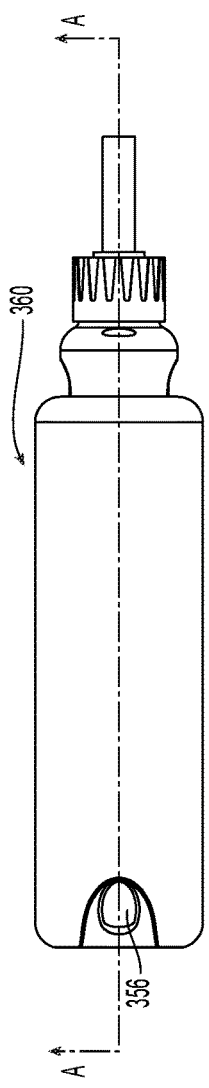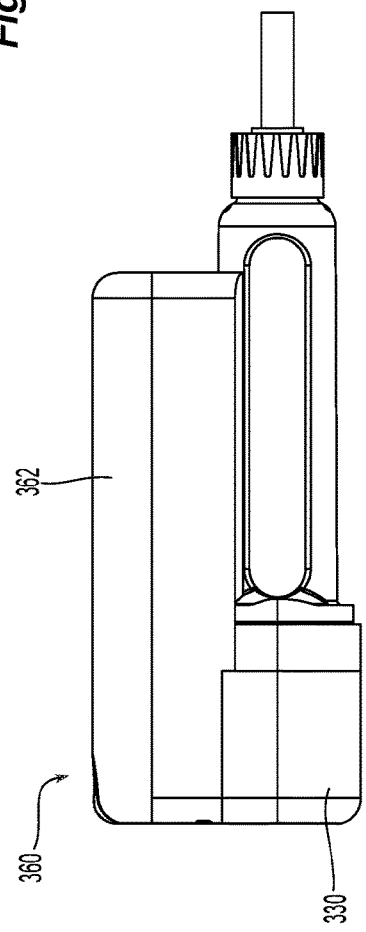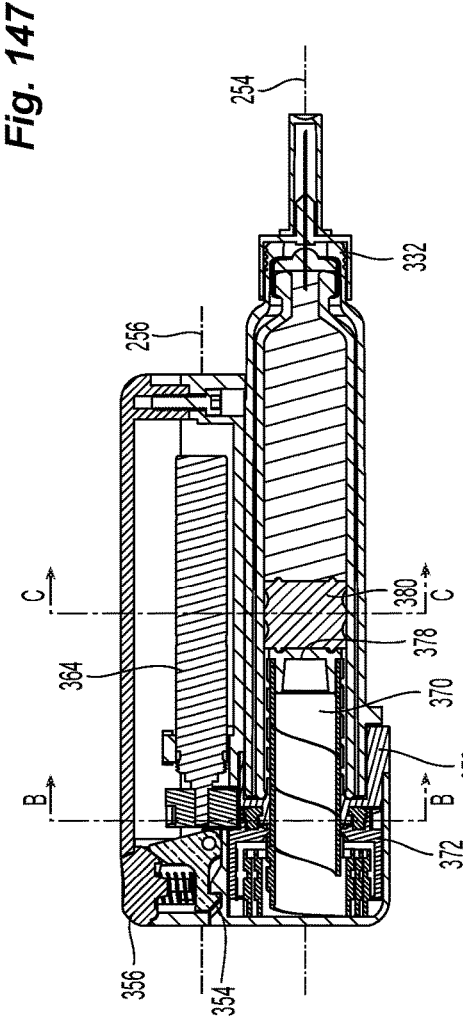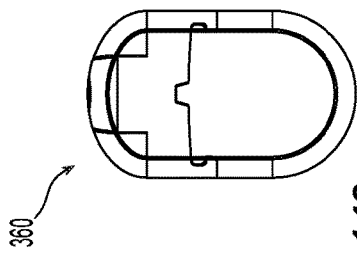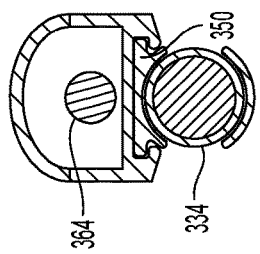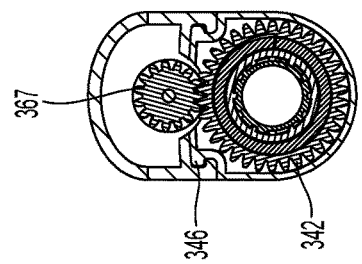
Fig. 146
Fig. 147
Fig. 149
Fig. 148
Fig. 151
Fig. 150

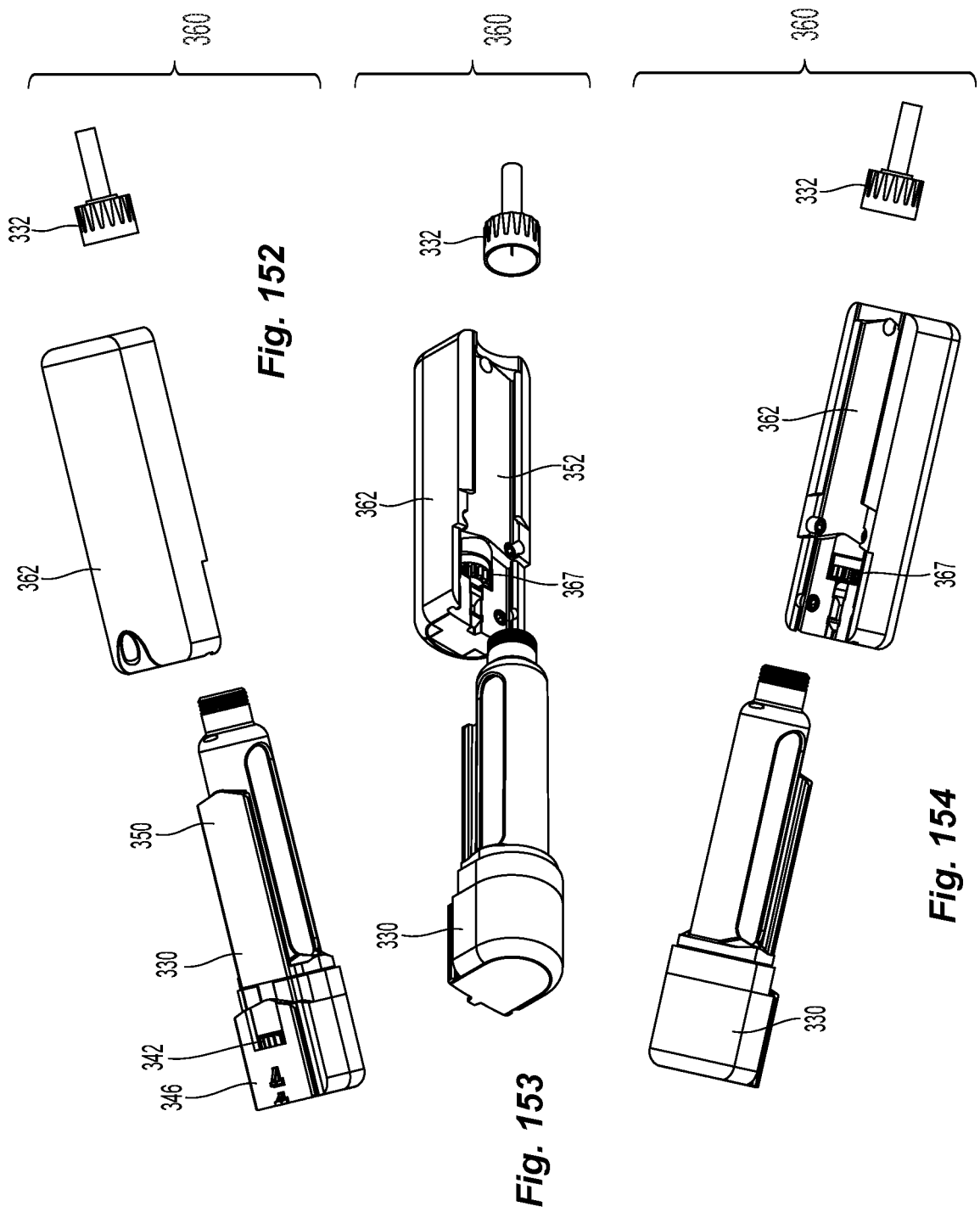

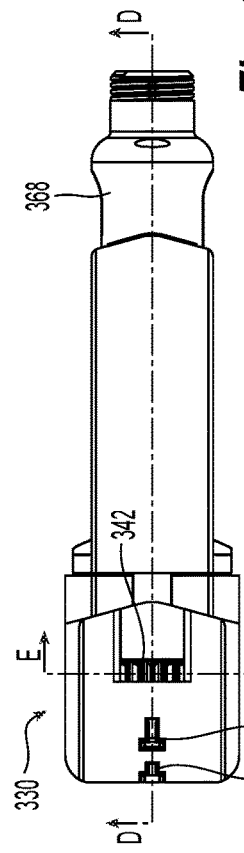
*Fig. 156*
*Fig. 160*
*Fig. 158*
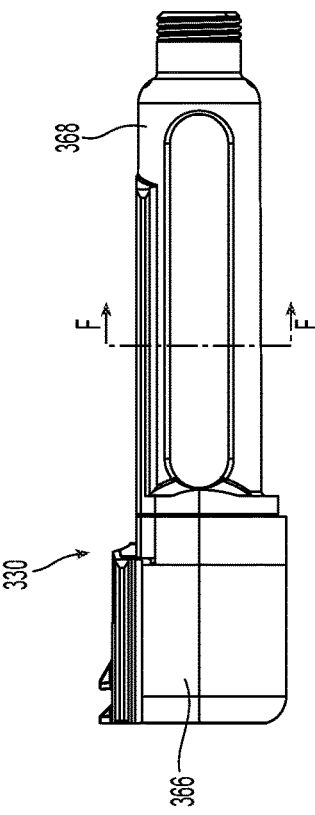
*Fig. 157*
*Fig. 161*
*Fig. 162*
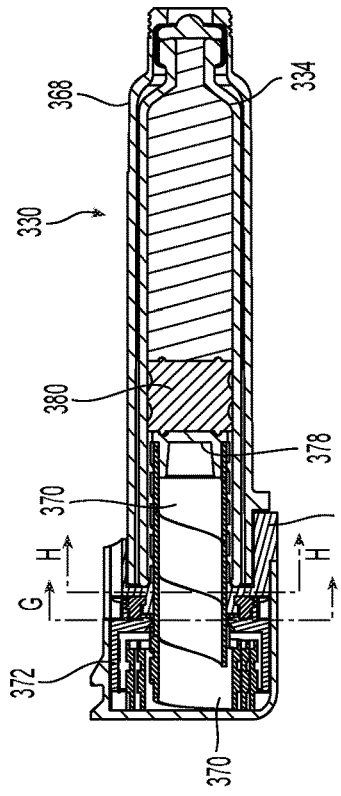
*Fig. 159*
*Fig. 163*

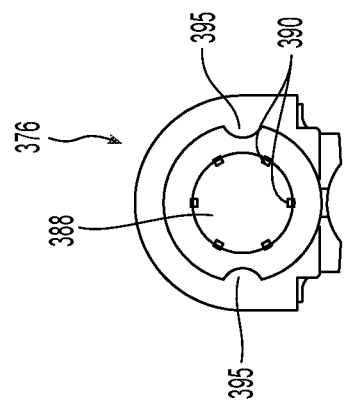
Fig. 175
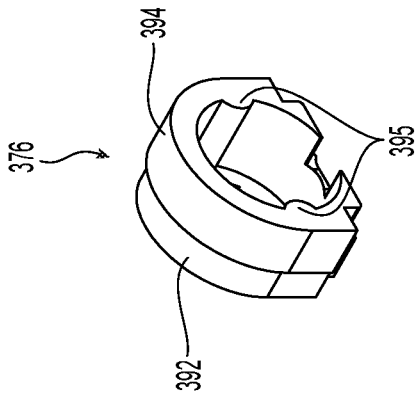
Fig. 172
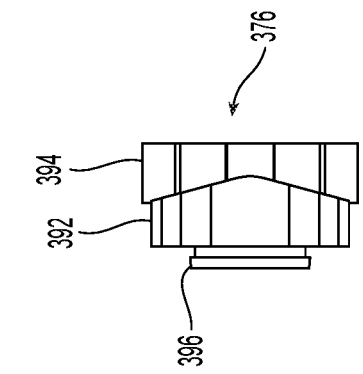
Fig. 174
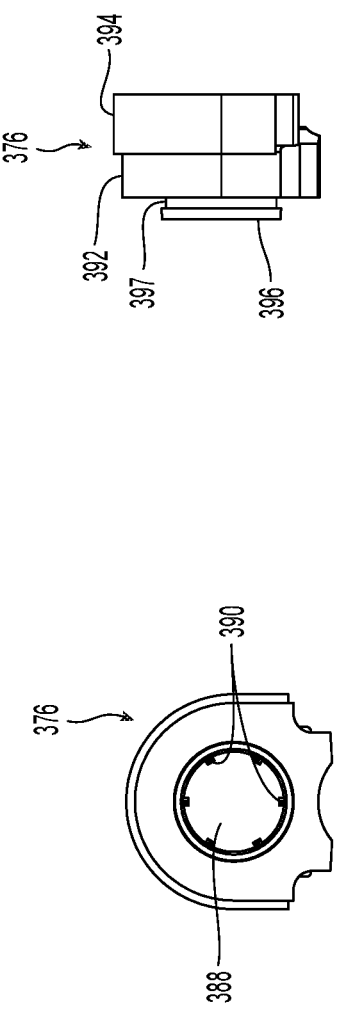
Fig. 173
Fig. 176
Fig. 171

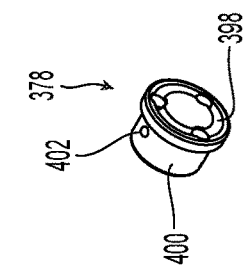
Fig. 183
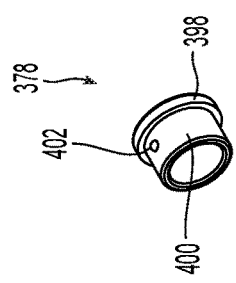
Fig. 182
Fig. 178
Fig. 177
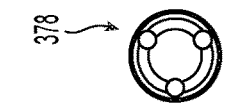
Fig. 186
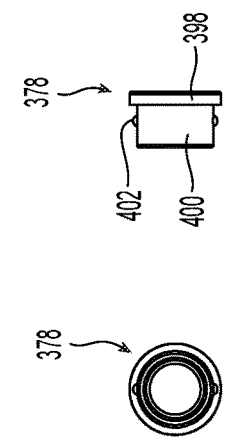
Fig. 185
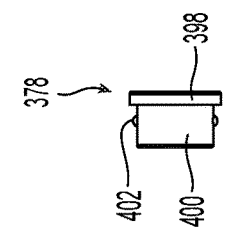
Fig. 184
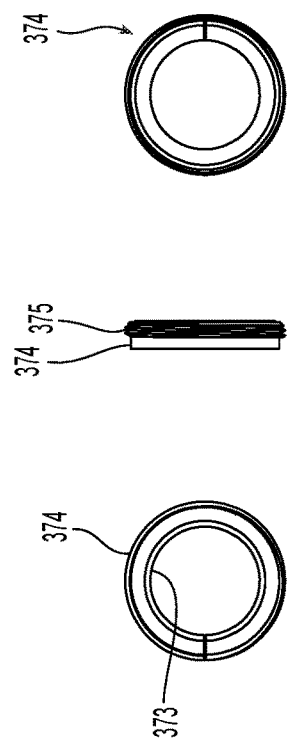
Fig. 181
Fig. 180
Fig. 179

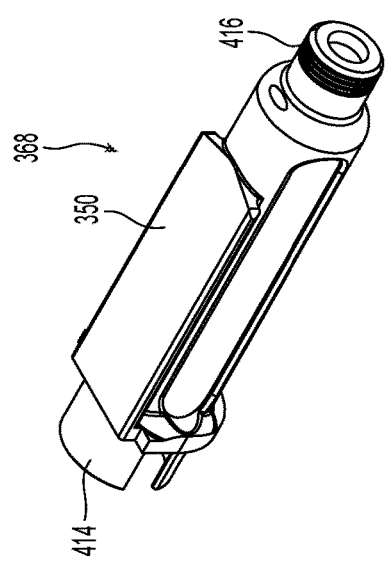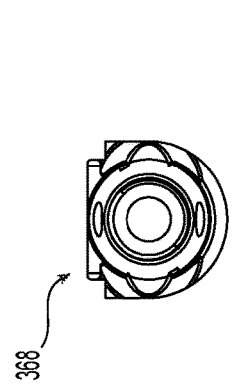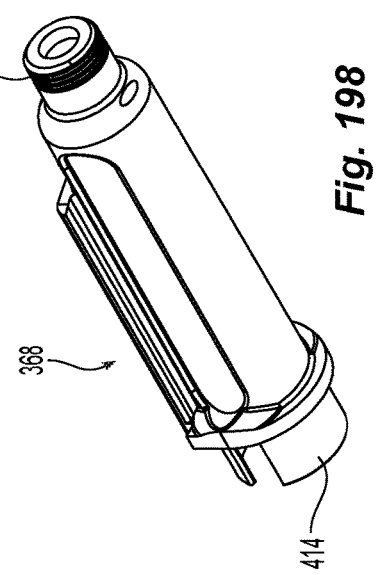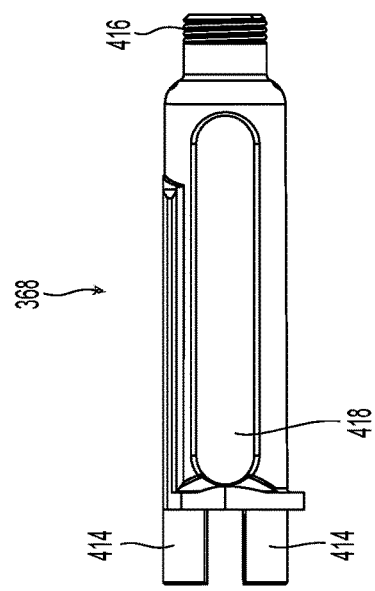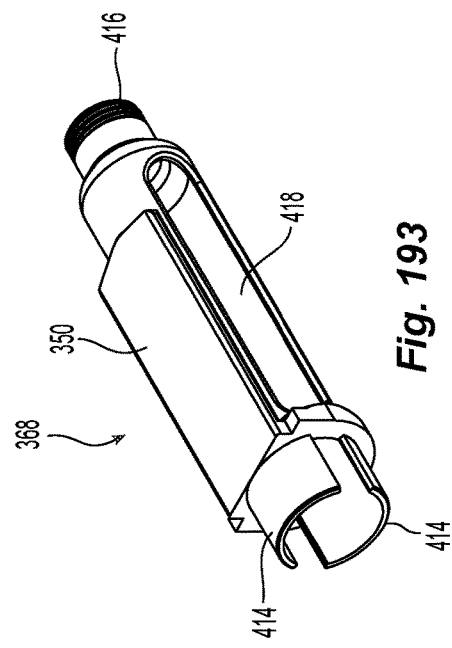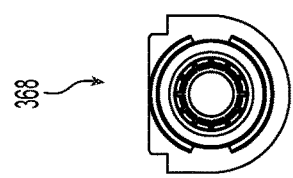

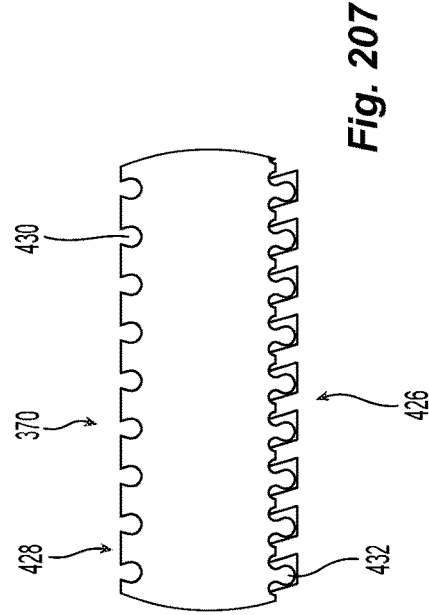
Fig. 207
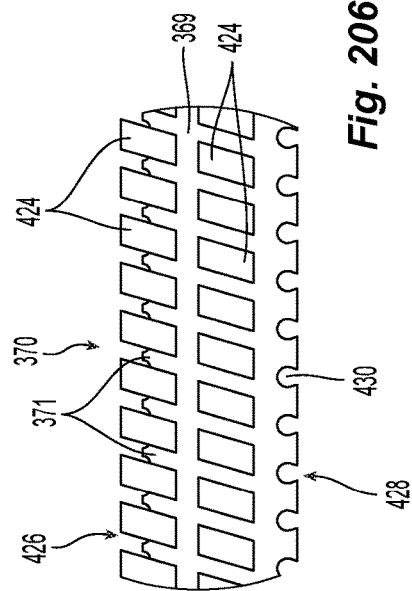
Fig. 206
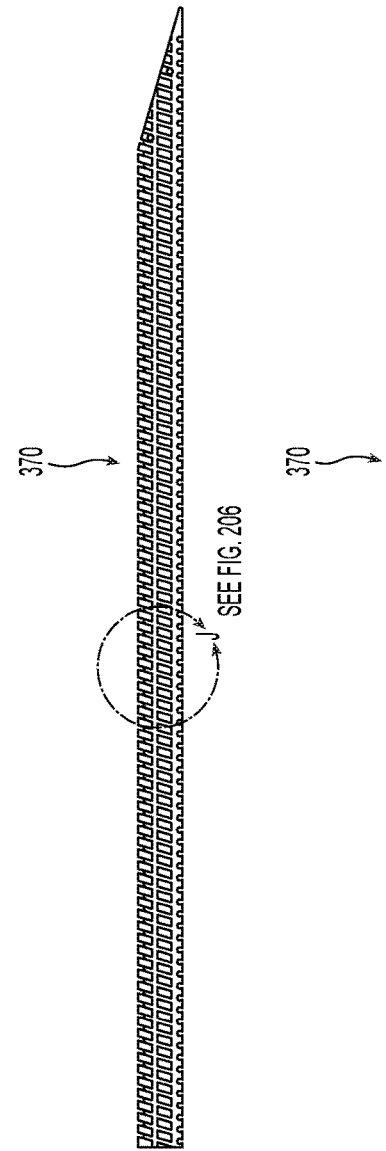
Fig. 203
Fig. 204
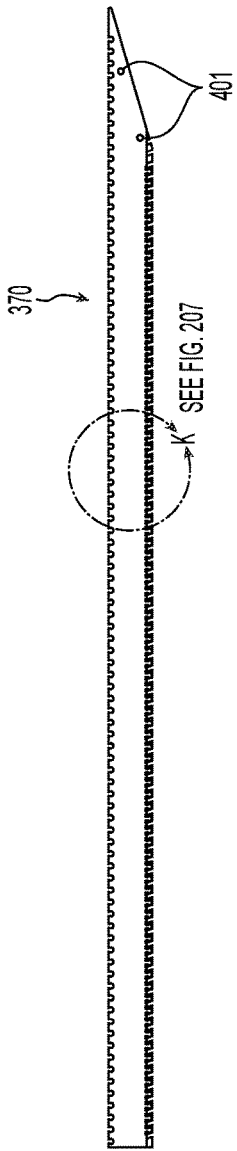
Fig. 205

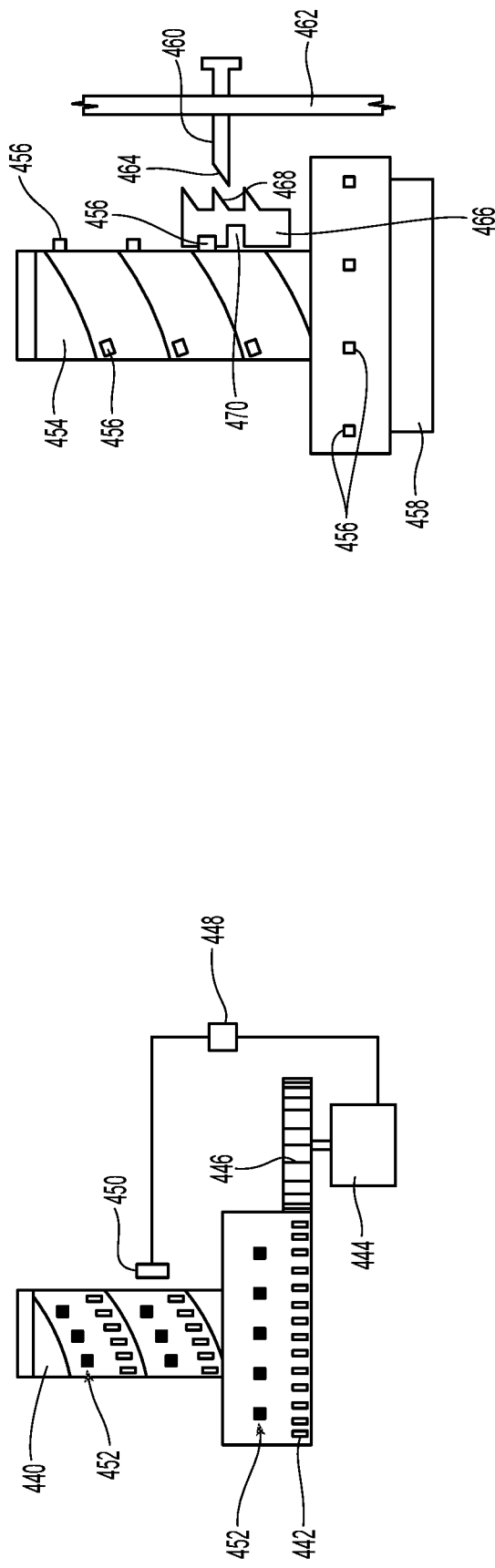
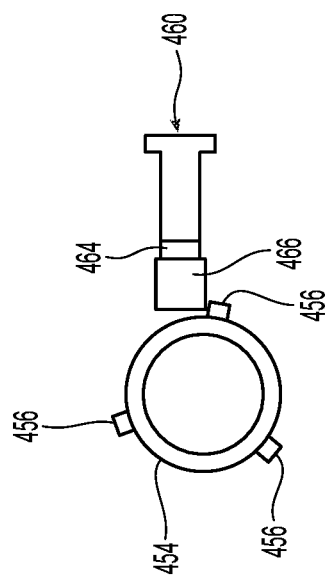
*Fig. 213*
*Fig. 214*
*Fig. 212*

MEDICAL DELIVERY DEVICE WITH AXIALLY EXPANDABLE DRIVE RIBBON

BACKGROUND

The present disclosure relates to medical delivery devices such as injection devices.

Conventional injection devices are often used to inject a medication into a patient. For example, injection pens that utilize disposable cartridges containing insulin are often used by diabetes patients. Such pens generally include an elongate rod that acts on a piston within the cartridge. As the rod advances the piston, the medication is dispensed through a needle into the patient.

The rod must project outwardly from the cartridge to engage a driving mechanism within the pen throughout the injection process including when the rod has reached the limit of forward advancement into the cartridge. The rod must also be accommodated within the pen when it is has been fully retracted so that the rod may be inserted into a fresh cartridge that is filled with medicament. As a result, conventional injection pens are generally elongate and thin with the length of the injection pen being more than twice the length of the cartridge barrel in which the medicament is contained. Similarly, for non-pen-shaped refillable injection devices, the length of the device is generally more than twice the length of the cartridge barrel in which the medicament is contained.

When such injection devices are used to self-administer the medicament at different times throughout the day, it is desirable for the injection device to be readily carried by the user. For example, diabetes patients often self-administer insulin using injection devices and carry the devices with them throughout the day. While conventional injection pens and similar devices are sufficiently small to be portable, the length of such devices often makes transport of the devices awkward.

SUMMARY

According to an embodiment of the present disclosure, a medication delivery device is provided for use with a container having a container body holding a medication and defining an outlet. The container includes a piston disposed within the container body, and advancement of the piston within the container body permits expelling of the medication through the outlet. The delivery device includes a housing adapted to couple with the container, and a drive assembly coupled with the housing and adapted to advance the piston within the container. The drive assembly includes a drive ribbon having a distal edge section and a proximal edge section. The drive ribbon is incrementally movable between a retracted configuration and an extended configuration about a drive axis. A retracted portion of the drive ribbon in the retracted configuration defines a spiral, and an extended portion of the drive ribbon in the extended configuration defines a helix. A thrust member is engaged with the drive ribbon and rotatably relative to the drive ribbon and the housing. In response to a rotation of the thrust member, the drive ribbon is movable between the retracted configuration and the extended configuration without any rotation relative to the housing or the container. Other embodiments of exemplary devices are provided.

In another embodiment, a medication delivery device includes a delivery device including a housing adapted to couple with the container, and a drive assembly coupled with the housing and adapted to advance the piston within the container. The drive assembly includes a drive ribbon having a distal edge section and a proximal edge section. The drive ribbon has a retracted configuration and an extended configuration. A retracted portion of the drive ribbon in the retracted configuration defines a spiral and an extended portion of the drive ribbon in the extended configuration defines a helix. The drive ribbon is incrementally movable from the retracted configuration to the extended configuration. Movement of the drive ribbon from the retracted configuration to the extended configuration defines a drive axis. A drive mechanism is operably coupled with the drive ribbon, and defining a secondary axis parallel with the drive axis. The drive mechanism generates a force that is transferred to the drive ribbon to move the drive ribbon from the retracted configuration to the extended configuration.

In yet another embodiment, a medication delivery device includes a delivery device including a housing adapted to couple with the container, and a drive assembly coupled with the housing and adapted to advance the piston within the container. The drive assembly includes a drive ribbon having a distal edge section and a proximal edge section. The drive ribbon has a retracted configuration and an extended configuration, where a retracted portion of the drive ribbon in the retracted configuration defines a spiral and an extended portion of the drive ribbon in the extended configuration defines a helix. The drive ribbon is incrementally movable from the retracted configuration to the extended configuration to advance said piston within the container body. Movement of the drive ribbon from the retracted configuration to the extended configuration defines a drive axis. One of the distal edge section and the proximal edge section defines a plurality of edge projections, and the other of the distal edge section and the proximal edge section defines a plurality of openings configured to receive corresponding edge projections in an interlocking manner when the drive ribbon is in the extended configuration.

In yet another embodiment, a medication delivery device includes a drive module and a cassette. The drive module includes a module housing, a motor disposed within the module housing, and a drive gear operably coupled to a shaft of the motor. The cassette includes a cassette housing configured to couple to the module housing. The cassette includes a container body holding a medication and defining an outlet, and a piston disposed within the container body. A drive ribbon is incrementally axially extendable to advance the piston within the container body to expel medication through the outlet. A thrust member includes a driven gear element operably coupled with the drive gear. The thrust member is engaged with the drive ribbon and movable to extend or retract the drive ribbon.

BRIEF DESCRIPTION OF THE DRAWINGS

The above mentioned and other features of the present disclosure, and the manner of attaining them, will become more apparent and the invention will be better understood by reference to the following description of embodiments of the present disclosure taken in conjunction with the accompanying drawings, wherein:

FIG. 52 is a schematic view of another device having a secondary axis.

FIG. 53 is a side view of the device of FIG. 52.

FIG. 54 is an end view of the device of FIG. 53.

FIG. 55 is a schematic view of an exemplary device having a secondary axis.

FIG. 56 is a side view of the device of FIG. 55.

FIG. 57 is an end view of the device of FIG. 56.

FIG. 58 is an end view of the device of FIG. 56.

FIG. 59 is a schematic view of the drive member mechanism of the device of FIG. 55 in a dialing dose setting configuration.

FIG. 60 is a schematic view of the drive member mechanism of the device of FIG. 55 in an injecting dose delivery configuration.

FIG. 61 is a schematic view of an exemplary device having a secondary axis.

FIG. 62 is a side view of the device of FIG. 61.

FIG. 63 is an end view of the device of FIG. 62.

FIG. 64 is an end view of the device of FIG. 62.

FIG. 65 is a schematic view of the drive member mechanism of the device of FIG. 61 in a dialing dose setting configuration.

FIG. 66 is a schematic view of the drive member mechanism of the device of FIG. 61 in an injecting dose delivery configuration.

FIG. 67 is a schematic view of an exemplary device having a secondary axis.

FIG. 68 is a side view of the device of FIG. 67.

FIG. 69 is an end view of the device of FIG. 68.

FIG. 70 is an end view of the device of FIG. 68.

FIG. 71 is a schematic view of the drive member mechanism of the device of FIG. 67 in a dialing dose setting configuration.

FIG. 72 is a schematic view of the drive member mechanism of the device of FIG. 67 in an injecting dose delivery configuration.

FIG. 73 is a schematic view of an exemplary device having a secondary axis.

FIG. 74 is a side view of the device of FIG. 73.
FIG. 75 is an end view of the device of FIG. 74.
FIG. 76 is an end view of the device of FIG. 74.
FIG. 77 is a schematic view of the drive member mechanism of the device of FIG. 73 in a dialing dose setting configuration.
FIG. 78 is a schematic view of the drive member mechanism of the device of FIG. 73 in an injecting dose delivery configuration.
FIG. 85 is a schematic view of an exemplary device having a secondary axis.
FIG. 86 is a side view of the device of FIG. 85.
FIG. 87 is an end view of the device of FIG. 86.
FIG. 88 is an end view of the device of FIG. 86.
FIG. 89 is a schematic view of the drive member mechanism of the device of FIG. 85 in a dialing dose setting configuration.
FIG. 90 is a schematic view of the drive member mechanism of the device of FIG. 85 in an injecting dose delivery configuration.
FIG. 91 is a schematic view of an exemplary device having a secondary axis.
FIG. 92 is a side view of the device of FIG. 91.
FIG. 93 is an end view of the device of FIG. 92.
FIG. 94 is an end view of the device of FIG. 92.
FIG. 95 is a schematic view of the drive member mechanism of the device of FIG. 91.
FIG. 96 is a schematic view of the drive member mechanism of the device of FIG. 91.
FIG. 97 is a schematic view of an exemplary device having a secondary axis.
FIG. 98 is a side view of the device of FIG. 97.
FIG. 99 is an end view of the device of FIG. 98.
FIG. 100 is an end view of the device of FIG. 98.
FIG. 101 is a schematic view of the drive member mechanism of the device of FIG. 97.
FIG. 102 is a schematic view of the drive member mechanism of the device of FIG. 97.
FIG. 103 is a schematic view of a device having a separable cassette and drive module.
FIG. 104 is a side view of the device of FIG. 103.
FIG. 105 is an end view of the device of FIG. 104.
FIG. 106 is an end view of the device of FIG. 104.
FIG. 107 is a side view of the cassette of FIG. 104.
FIG. 108 is a side view of the drive member mechanism module of FIG. 104.
FIG. 109 is a schematic view of an exemplary device having a separable cassette and drive module.
FIG. 110 is a side view of the device of FIG. 109.
FIG. 111 is an end view of the device of FIG. 110.
FIG. 112 is an end view of the device of FIG. 110.
FIG. 113 is a side view of the cassette of FIG. 110.
FIG. 114 is a side view of the drive member mechanism module of FIG. 110.
FIG. 115 is a schematic view of an exemplary device having a separable cassette and drive module.
FIG. 116 is a side view of the device of FIG. 115.
FIG. 117 is an end view of the device of FIG. 116.
FIG. 118 is an end view of the device of FIG. 116.
FIG. 119 is a side view of the cassette of FIG. 116.
FIG. 120 is a side view of the drive member mechanism module of FIG. 116.
FIG. 121 is a schematic view of an exemplary device having a separable cassette and drive module.
FIG. 122 is a side view of the device of FIG. 121.
FIG. 123 is an end view of the device of FIG. 122.
FIG. 124 is an end view of the device of FIG. 122.
FIG. 125 is a side view of the cassette of FIG. 122.
FIG. 126 is a side view of the drive member mechanism module of FIG. 122.
FIG. 137 is a side view of an exemplary device having a cassette and a modular drive member mechanism.
FIG. 138 is another side view of the device of FIG. 137.
FIG. 139 is an end view of the device of FIG. 138.
FIG. 140 is a cross section taken along line A-A of FIG. 137.
FIG. 141 is a cross section taken along line B-B of FIG. 140.
FIG. 142 is a cross section taken along line C-C of FIG. 140.
FIG. 143 is an exploded view of the device of FIG. 137 showing the drive member mechanism and the cassette separated.
FIG. 144 is an exploded view of the device of FIG. 137 showing the drive member mechanism and the cassette separated.
FIG. 145 is an exploded view of the device of FIG. 137 showing the drive member mechanism and the cassette separated.
FIG. 146 is a side view of an exemplary device having a cassette and a modular drive member mechanism.
FIG. 147 is another side view of the device of FIG. 146.
FIG. 148 is an end view of the device of FIG. 147.
FIG. 149 is a cross section taken along line A-A of FIG. 146.
FIG. 150 is a cross section taken along line B-B of FIG. 149.
FIG. 151 is a cross section taken along line C-C of FIG. 149.
FIG. 152 is an exploded view of the device of FIG. 146 showing the drive member mechanism and the cassette separated.
FIG. 153 is an exploded view of the device of FIG. 146 showing the drive member mechanism and the cassette separated.

FIG. 154 is an exploded view of the device of FIG. 146 showing the drive member mechanism and the cassette separated.

FIG. 156 is a side view of the cassette of FIG. 155.

FIG. 157 is another side view of the cassette of FIG. 155.

FIG. 158 is an end view of the cassette of FIG. 155.

FIG. 159 is a cross section taken along line D-D of FIG. 156.

FIG. 160 is a cross section taken along line E-E of FIG. 156.

FIG. 161 is a cross section taken along line F-F of FIG. 157.

FIG. 162 is a cross section taken along line G-G of FIG. 159.

FIG. 163 is a cross section taken along line H-H of FIG. 159.

FIG. 171 is a perspective view of the cassette collar of FIG. 164.

FIG. 172 is a perspective view of the cassette collar of FIG. 164.

FIG. 173 is an end view of the cassette collar of FIG. 164.

FIG. 174 is a side view of the cassette collar of FIG. 164.

FIG. 175 is an end view of the cassette collar of FIG. 164.

FIG. 176 is a side view of the cassette collar of FIG. 164.

FIG. 177 is a perspective view of the cassette ring of FIG. 164.

FIG. 178 is a perspective view of the cassette ring of FIG. 164.

FIG. 179 is an end view of the cassette ring of FIG. 164.

FIG. 180 is a side view of the cassette ring of FIG. 164.

FIG. 181 is an end view of the cassette ring of FIG. 164.

FIG. 182 is a perspective view of the cassette foot of FIG. 164.

FIG. 183 is a perspective view of the cassette foot of FIG. 164.

FIG. 184 is an end view of the cassette foot of FIG. 164.

FIG. 185 is a side view of the cassette foot of FIG. 164.

FIG. 186 is an end view of the cassette foot of FIG. 164.

FIG. 193 is a perspective view of the cassette holder of FIG. 164.

FIG. 194 is a perspective view of the cassette holder of FIG. 164.

FIG. 195 is an end view of the cassette holder of FIG. 164.

FIG. 196 is a side view of the cassette holder of FIG. 164.

FIG. 197 is an end view of the cassette holder of FIG. 164.

FIG. 198 is a perspective view of the cassette holder of FIG. 164.

FIG. 199 is a perspective view of the drive ribbon of FIG. 164.

FIG. 200 is a perspective view of the drive ribbon of FIG. 164.

FIG. 201 is a side view of the drive ribbon of FIG. 164.

FIG. 202 is an end view of the drive ribbon of FIG. 164.

FIG. 203 is a view of the external surface of the drive ribbon of FIG. 164 when laying flat.

FIG. 204 is a view of the edge of the drive ribbon of FIG. 164 when laying flat.

FIG. 205 is a view of the internal surface of the drive ribbon of FIG. 164 when laying flat.

FIG. 206 is an enlarged view of a section of the drive ribbon shown in Detail J of FIG. 203.

FIG. 207 is an enlarged view of a section of the drive ribbon shown in Detail K of FIG. 205.

FIG. 208 is a view of the external surface of two drive ribbons of FIG. 164 joined together and laying flat for explanatory purposes.

FIG. 209 is a view of the internal surface of two drive ribbons of FIG. 164 joined together and laying flat for explanatory purposes.

Figure 208:
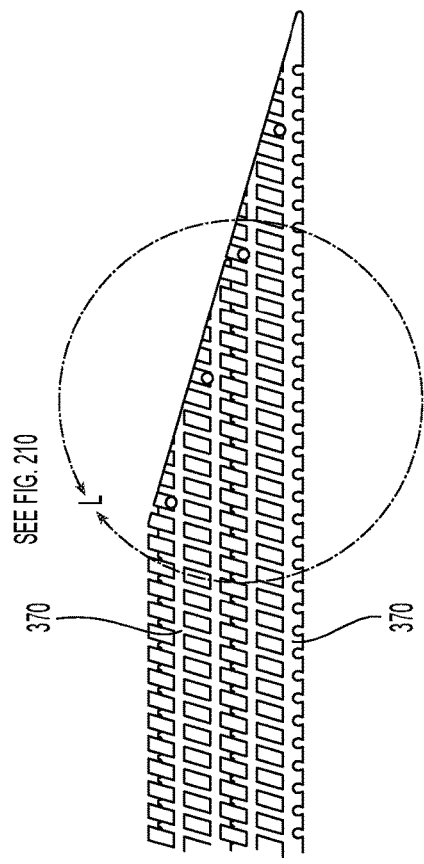
Figure 210:
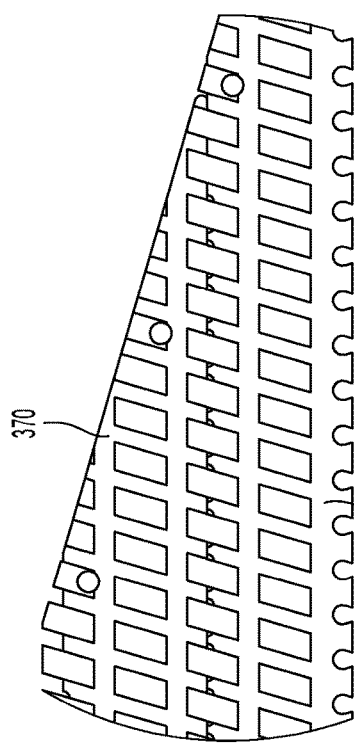

FIG. 210 is an enlarged view of a section of the drive ribbon shown in Detail L of FIG. 208.

Figure 209:
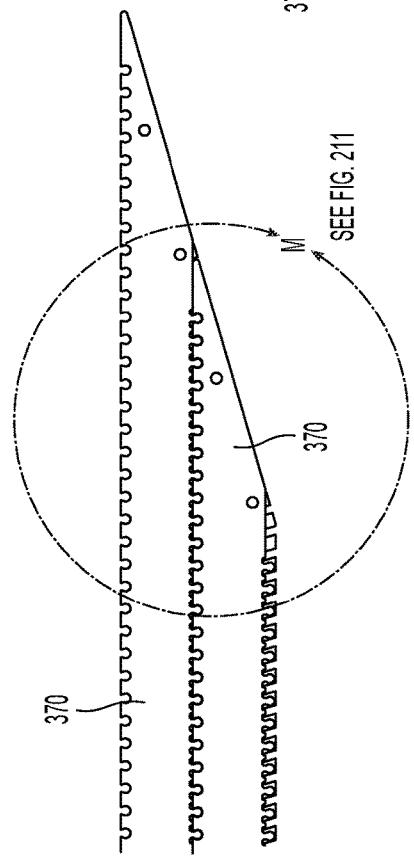
Figure 211:
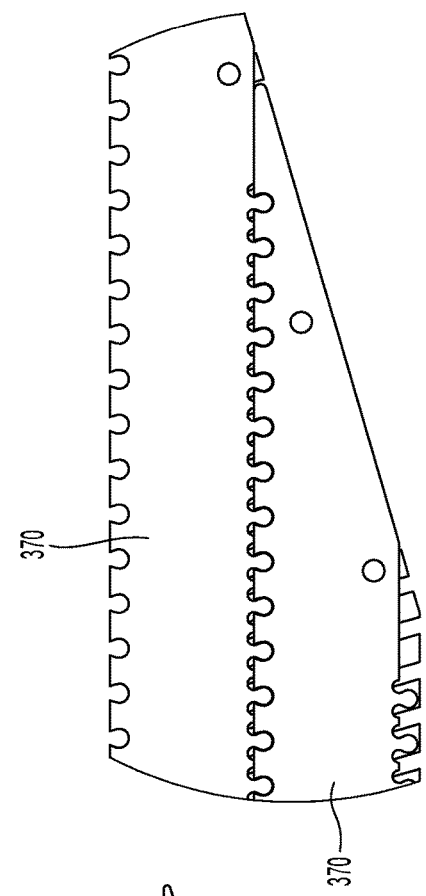

FIG. 211 is an enlarged view of a section of the drive ribbon shown in Detail M of FIG. 209.

FIG. 212 is a schematic view of a control system for controlling the dosage amount delivered by a device.

FIG. 213 is a schematic view of another control system for controlling the dosage amount delivered by a device.

FIG. 214 is a schematic top view of the control system of FIG. 213.

Figure 215:
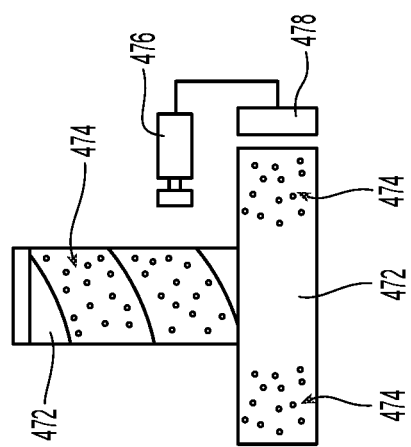

FIG. 215 is a schematic view of another control system for controlling the dosage amount delivered by a device.

Figure 216:
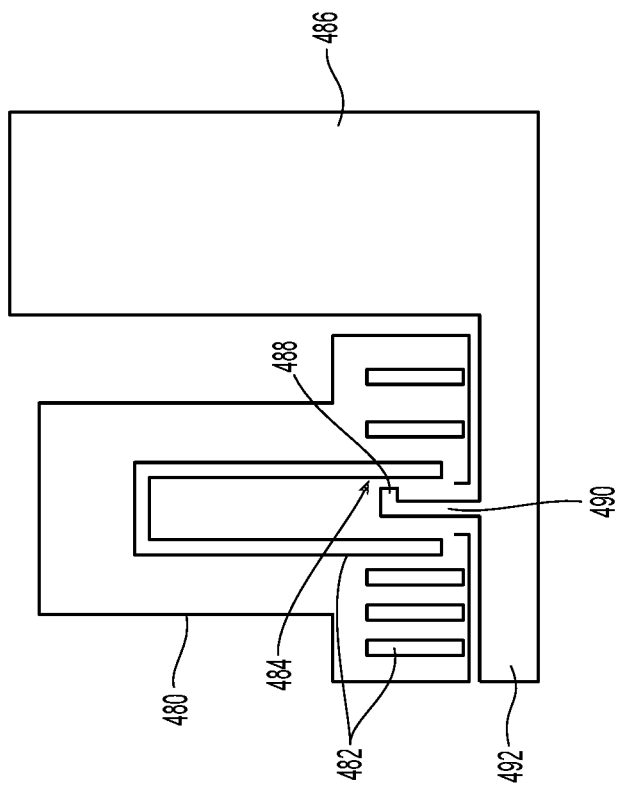

FIG. 216 is a schematic view of an alternative physical layout for a control system.

Corresponding reference characters indicate corresponding parts throughout the several views. Although the exemplification set out herein illustrates embodiment of the present disclosure, in several forms, the embodiments disclosed below are not intended to be exhaustive or to be construed as limiting the scope of the invention to the precise forms disclosed.

DETAILED DESCRIPTION

Examples of a medication delivery device are provided. One of the advantages may be that such delivery device may provide a configuration having a relatively short length and compact configuration. In some embodiments, the device is a disposable device, such as an autoinjector, with a syringe prefilled with a medication, such as, for example, insulin or other type drug for treatment of diabetes. In some embodiments, the device includes a disposable syringe cartridge that is removably coupled to a drive housing such that a patient may replace the used cartridge with another cartridge having a new and/or different medication. The drive housing may include electronics for sensing, indicating, displaying and/or communicating onboard and/or off board steps in drug delivery.

The illustrated devices utilize an axially expandable drive ribbon as part of the drive assembly for dispensing a medication. As can be seen with reference to FIGS. 1-3, the drive ribbons of the exemplary embodiments have a retracted configuration in which a retracted portion of the drive ribbon 22 defines a spiral and an extended configuration wherein an extended portion of the drive ribbon 24 defines a helix.

As used herein, the retracted portion 22 of the drive ribbon defines the proximal end and the opposite end of the extended portion 24 of the drive ribbon defines the distal end. The drive ribbon can be incrementally shifted between the retracted configuration and extended configuration to alter the length of the extended portion 24. As the drive ribbon is shifted to the extended configuration, the ribbon is formed into a helix and the ribbon is secured to itself as a proximal edge region of the ribbon is engaged with a distal edge region of ribbon.

Figure 1:
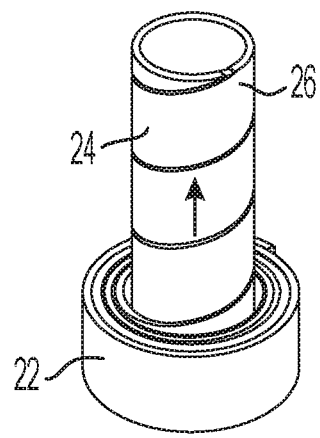
FIG. 1 is a schematic perspective view of an exemplary drive ribbon that is axially extendable without rotation of the drive ribbon.
Figure 2:
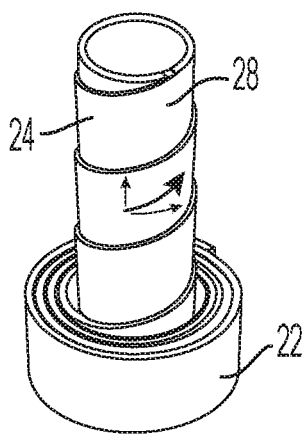
FIG. 2 is a schematic perspective view of another exemplary drive ribbon that rotates as it is axially extended.
Figure 3:
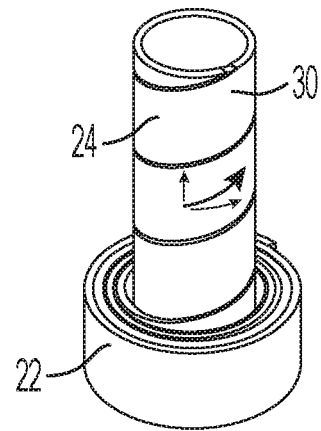
FIG. 3 is a schematic perspective view of another drive ribbon that rotates as it is axially extended.

FIGS. 1-3 illustrate several different manners in which the drive ribbon may function. FIG. 1 schematically depicts a drive ribbon 26 in which the extended portion 24 of the drive ribbon advances without rotation of the extended portion 24. In such an embodiment, as the extended portion of the drive ribbon is advanced axially, the nearest retracted portion of the ribbon is drawn radially inward and upward such that distal edge of the ribbon being drawn in is engaged to the proximal edge of the ribbon at the bottom of the extended portion of the ribbon. The ribbon can be guided in this movement by the use of a camming ramp engaged with the proximal edge of the ribbon being drawn radially inward and upward.

One advantage of such a non-rotating drive ribbon is that a bearing member attached to the distal end of the ribbon will not rotate and, thus, can bear directly on the piston of a medication container without any relative rotational movement between the bearing member and the piston.

FIGS. 2 and 3 schematically depict drive ribbons 28, 30 which rotate as they are axially extended. The distinction between drive ribbon 28 shown in FIG. 2 and drive ribbon 30 shown in FIG. 3 is the manner in which the distal and proximal edges of the ribbons are engaged. Ribbon 28 shown in FIG. 2 has edges that project inwardly and outwardly to form projecting lips. Similar ribbons are shown in FIGS. 7-9 and FIG. 33 which are discussed below.

Drive ribbon 30, similar to ribbon 26, forms a more cylindrical shape and the proximal and distal edges of the ribbon do not project or form a significant discontinuity in the inner and outer surfaces of the extended portion 24 of the ribbon. The drive ribbons shown in FIGS. 4-6 and 11 have this type of engagement and are further discussed below.

The use of a rotating drive ribbon allows for a greater variety of drive ribbon configurations than that of a non-rotating drive ribbon. The rotation of the drive ribbon, however, will generally require that the bearing member be mounted to a secondary component on the drive ribbon to allow a bearing member engaged with the piston of the medication container to rotate relative to the drive ribbon. This will allow the bearing member to engage the piston of the medication container without any relative movement between the bearing member and piston. This arrangement may also increase the overall length of the drive ribbon assembly.

Because of the short axial length of the retracted portion of the drive ribbon, the use of such a drive ribbon allows an injection device or similar medication delivery device to have a relatively short and compact size. Various different drive assemblies for moving the drive ribbon and device architectures are disclosed herein and discussed below.

Exemplary Drive Ribbons

Figure 4:
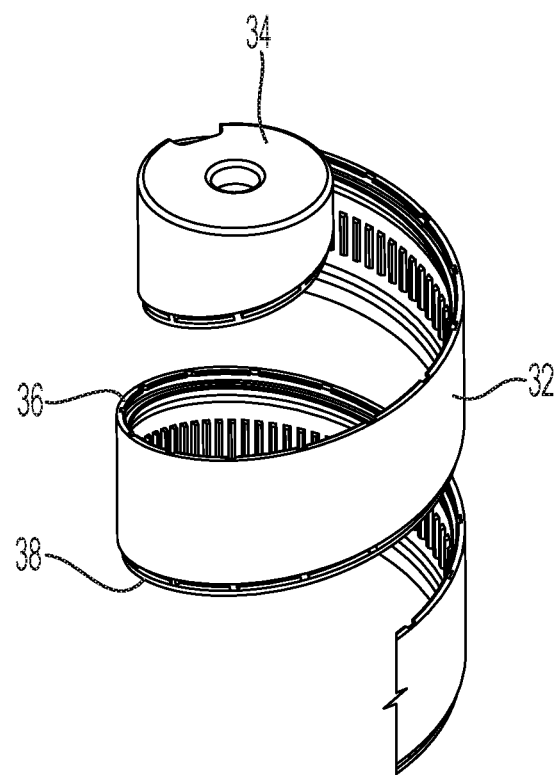
FIG. 4 is a partial exploded view of an exemplary drive ribbon.
Figure 5:
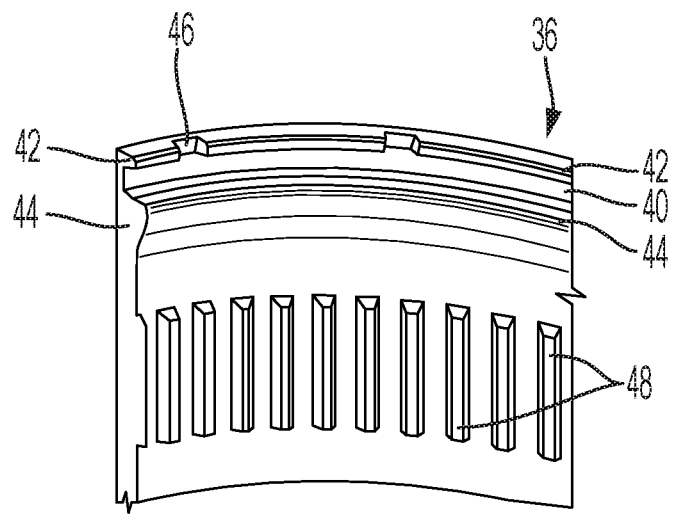
FIG. 5 is a detail view of the drive ribbon of FIG. 4.
Figure 6:
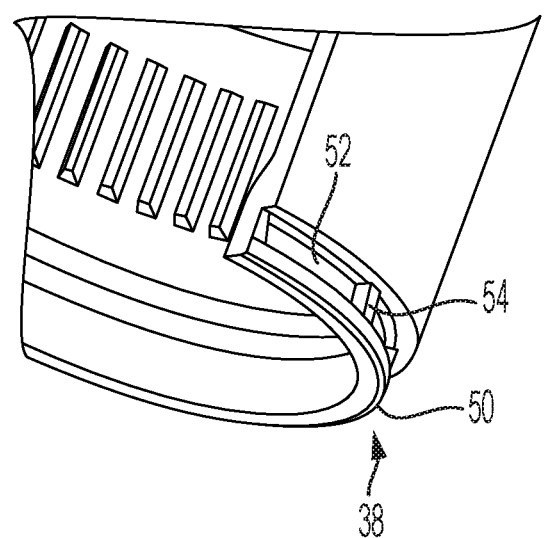
FIG. 6 is another detail view of the drive ribbon of FIG. 4.

One example of a drive ribbon 32 that forms a generally cylindrical extended portion (similar to the ribbons of FIGS. 1 and 3) is shown in FIGS. 4-6. Ribbon 32 would not take the shape shown in FIG. 4 during use and is shown in this configuration merely to aid in understanding the structure of ribbon 32. A foot member 34 is secured to the distal end of ribbon 32. If ribbon 32 is used in a non-rotating application, foot 34 can bear directly against the piston of a medication container. Foot 34 also includes a central bore which may function as a rotatable bearing. For example, a bearing member having a projection that fits into the central bore of foot 34 could be rotatably mounted on foot 34 and bear directly on the piston instead of foot 34. This arrangement would facilitate the use of ribbon 32 in an application where the drive ribbon rotates as it is axially advanced.

Ribbon 32 has a distal edge section 36 and a proximal edge section 38 which are engageable with each other and are shown in greater detail in FIGS. 5 and 6. Distal edge section 36 faces inwardly and includes a recess 40 disposed between an inwardly projecting lip 42 and inwardly projecting ledge 44. Lip 42 also includes a series of notches 46. The inwardly facing surface of ribbon 32 also includes a series of raised ribs 48. Ribs 48 may be engaged by a gear or similar drive member mechanism to rotatably drive the movement of ribbon 32.

Proximal edge section 38 can be seen in FIG. 6 and the outwardly facing surface of ribbon 32 includes a lip 50 and a recess 52 along the proximal edge of ribbon 32. Axially extending ribs 54 are located within recess 52. When the proximal and distal sections of ribbon 32 are engaged together, lip 50 fits within recess 40 with lip 42 and ledge 44 restraining its axial movement. Similarly, lip 42 fits within recess 52 and is axially restrained as a result. This axial engagement allows the extended portion of the ribbon 32 to exert axial compressive forces, such as when biasing a piston forward to expel medication, and resist axial tensile forces to thereby prevent the extended portion of the ribbon from becoming disengaged from itself due to being pulled apart axially. Ribs 54 fit within notches 46 to provide shear resistance and allow the extended portion of the ribbon to withstand torque that it may be subjected to when being rotated.

Figure 7:
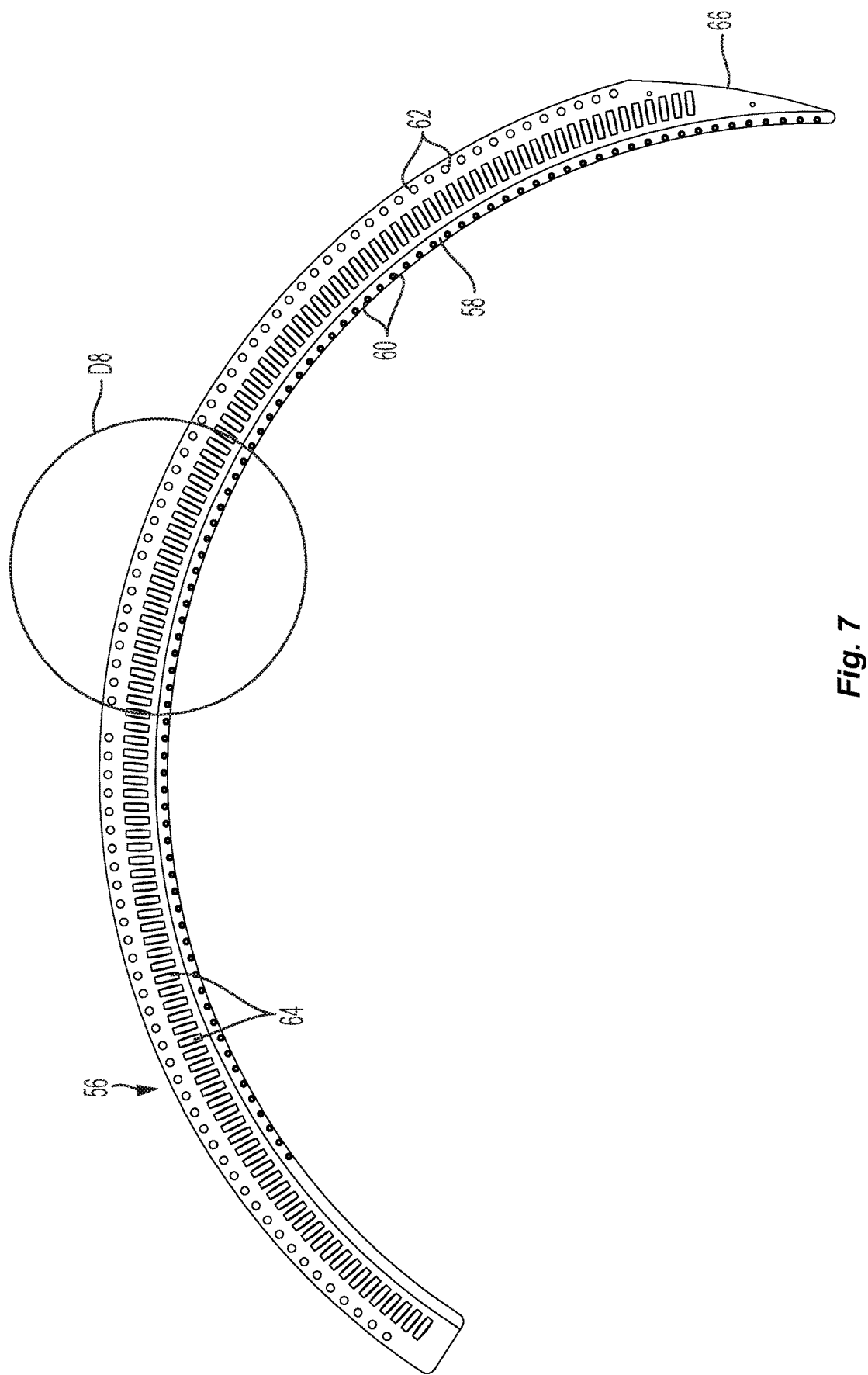
FIG. 7 is a view of another drive ribbon with the ribbon unrolled.
Figure 8:
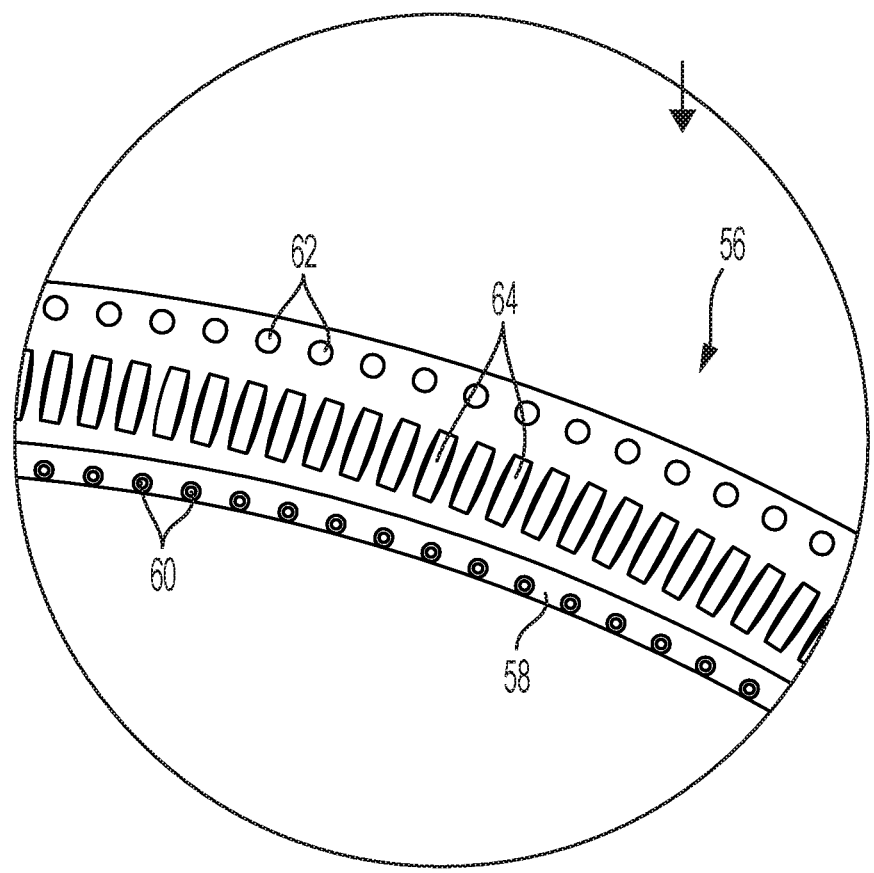
FIG. 8 is a detail view of the drive ribbon of FIG. 7.
Figure 9:
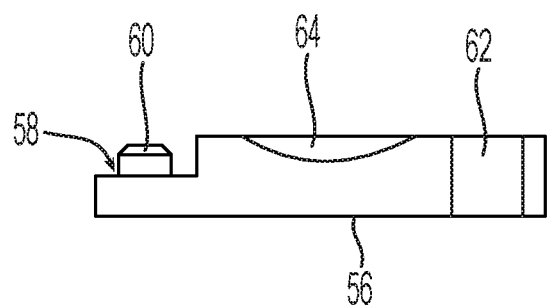
FIG. 9 is an edge view of the drive ribbon of FIG. 7.

An example of a drive ribbon that has proximal and distal edges that form projecting lips when engaged (similar to the ribbon of FIG. 2) and has sidewalls taking a slightly conical shape when in an extended position, is shown in FIGS. 7-9. Ribbon 56 is shown laying on a flat surface in FIG. 7. FIGS. 8 and 9 provide more detailed views of ribbon 56.

Drive ribbon 56 includes a recessed area 58 along the proximal edge section of ribbon 56 that receives an adjacent portion of the distal edge section of ribbon 56 when ribbon 56 is extended and forms a helix. Recessed portion 58 does not, however, receive the full thickness of the distal edge section and a portion of both the distal and proximal edge sections project radially in opposite directions as a result.

A plurality of pegs 60 are located in recess 58 and engage a corresponding plurality of holes 62. In the illustrated embodiment, pegs 60 are located on the proximal edge section with holes 62 being located on the distal edge section. These positions, however, in other examples, can be reversed. As drive ribbon 56 is extended and formed into a helix, the engagement of the proximal edge section with an adjacent portion of the distal edge section includes the engagement of pegs 60 with holes 62. In the illustrated embodiment, pegs 60 have a chamfered tip surface that facilitates the entry and removal of pegs 60 from holes 62.

The engagement of pegs 60 with holes 62 secures the adjacent portions of drive ribbon 56 together axially. The engagement of pegs 60 and holes 62 also provides for the transfer of torque between adjacent portions of the extended ribbon and maintains the stability of the column formed by the extended ribbon.

In the illustrated embodiment, drive ribbon 56 has a plurality of recesses 64 that provide a geared surface. Recesses 64 are engaged by a gear member or other suitable drive member whereby a drive assembly can rotate drive ribbon 56 by transmitting a rotational force to drive ribbon 56. As can be seen in FIG. 7, drive ribbon 56 includes a tapered section 66 that, when formed into a helix, defines the distal end of the drive ribbon and has a bearing member, such as foot 34, mounted thereto.

The illustrated drive ribbons utilize a flexible polymeric ribbon that has been machined to define the various features of the ribbon. Nylon, polypropylene, acetal (polyoxymethylene or POM), and high density polyethylene are examples of suitable polymeric materials that may be used to form a drive ribbon. While the illustrated embodiments are machined, alternative embodiments could use a molding process to form a polymeric ribbon with all of its features. It is envisioned that molding the ribbon in a flat arrangement and then rolling the ribbon into a spiral configuration will be the most efficient manufacturing method of forming a ribbon.

Other materials may also be used to form a drive ribbon. For example, thin metal strip could be used to form the ribbon. Photo etching, laser etching or other suitable micro machining methods could be used to form the individual features of the ribbon. Alternatively, a metal ribbon could be formed by diffusion bonding two half-thickness layers instead of using a single metal strip.

Still other ribbon embodiments might take the form of an overmolded metal strip. The metal strip would be provided with the distal edge features and the overmolded plastic portion of the ribbon would form the various features of the ribbon. This approach combines the desirable stiffness, elasticity and creep resistance of metal with the low friction and manufacturing ease of forming small features in molded plastic. It will generally be desirable for the ribbon to be flexible so that the ribbon can be extended and retracted, and undergo concomitant elastic strains, without permanent deformation.

In this regard, it is noted that the various embodiments disclosed herein may be either single-use devices or multiple use devices with some of the devices being best suited for one or the other. A multiple-use device will have a drive ribbon that can be extended and retracted multiple times so that it may be re-used with a new medication container after depleting a medication container. A single use drive ribbon will be used with only a single medication container and, once extended, will be discarded. Such single use drive ribbons do not need to have the ability to be retracted after extension. The ability of drive ribbons to resist axial tension and thus resist axial separation in the extended portion of the drive ribbon is most important during the retraction of the drive ribbon and if the drive ribbon is exposed while extended. Such concerns are reduced, if not eliminated, for single-use drive ribbons and, for at least some applications, it may not be necessary for the extended portion of the drive ribbon to have the ability to resist axial separation forces.

Non-Rotating Drive Ribbon

FIGS. 10-21 relate to devices having a drive ribbon that does not rotate as it is axially advanced. Such medication delivery devices are suitable for use with a container having a container body holding a medication and defining an outlet wherein the container includes a piston disposed within the container body and advancement of the piston within the container body expels medication through the outlet (e.g., a hollow needle). The delivery device includes a housing adapted to couple with the container and a drive assembly coupled with the housing and adapted to advance the piston within the container. The drive assembly includes a drive ribbon having a distal edge section and a proximal edge section. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally movable from the retracted configuration to the extended configuration. Movement of the drive ribbon from the retracted configuration to the extended configuration defines a drive axis and advances the piston within the container body. The drive ribbon moves from the retracted configuration to the extended configuration without rotating relative to the housing or the container. A thrust member is engaged with the drive ribbon. The thrust member is rotatable relative to both the drive ribbon and the housing. Rotation of the thrust member moves the drive ribbon from the retracted configuration to the extended configuration.

Non-Rotating Drive Ribbon with Stationary Thrust Member

In some embodiments having such a non-rotating drive ribbon, the thrust member is axially stationary. Such an axially stationary thrust member may include a helical thread engageable with the drive ribbon and the device may further include a rotational restraint member wherein the rotational restraint member is rotationally fixed relative to the housing and engaged with the drive ribbon and the engagement of the drive ribbon and the rotational restraint member prevents relative rotation of the extended portion of the drive ribbon and the rotational restraint member.

In such devices having a rotational restraint member, one of the rotational restraint member and the extended portion of the drive ribbon may define an axially extending key with the other one of the rotational restraint member and extended portion of the drive ribbon defining an axially extending keyway.

The rotational restraint member may be disposed radially outside of the drive ribbon at an engagement location where the rotational restraint member engages the drive ribbon to prevent rotation. See, for example, the embodiment of FIGS. 10 and 11, the embodiment of FIGS. 12 and 13, and the embodiment of FIGS. 16 and 17.

Alternatively, the rotational restraint member may be disposed radially inside of the drive ribbon at the location where the rotational restraint member engages the drive ribbon to prevent rotation. See, for example, the embodiment of FIGS. 14 and 15.

For embodiments having an axially stationary thrust member with a helical thread, the helical thread may be disposed radially outside of the drive ribbon at the location where the helical thread engages the drive ribbon. See, for example, the embodiment of FIGS. 10 and 11, the embodiment of FIGS. 12 and 13, and the embodiment of FIGS. 14 and 15. Alternatively, the helical thread may be disposed radially inside of the drive ribbon at the location where the helical thread engages the drive ribbon. See, for example, the embodiment of FIGS. 16 and 17.

Figure 10:
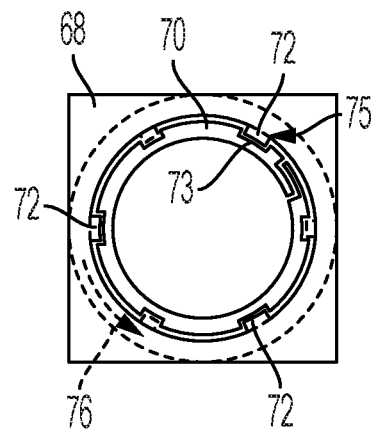
FIG. 10 is a schematic end view of an exemplary drive assembly having a drive ribbon that does not rotate as it extends.
Figure 11:
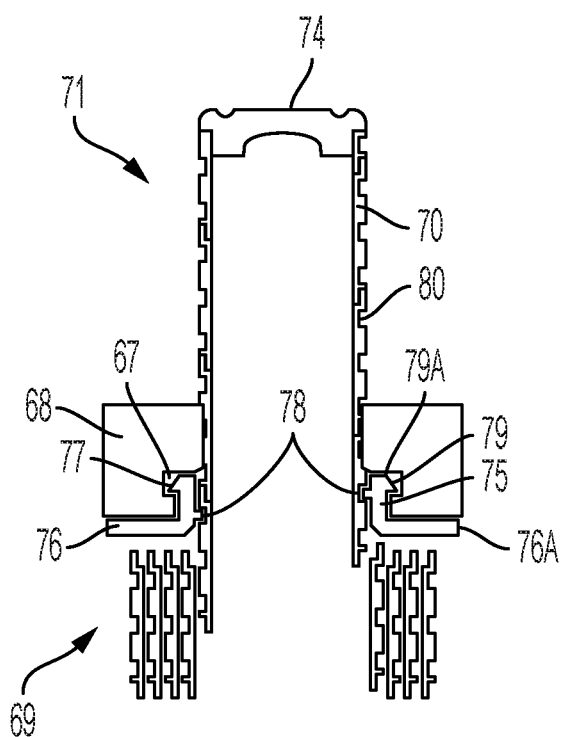
FIG. 11 is another schematic view of the drive assembly of FIG. 10.

Turning now to the embodiment of FIGS. 10 and 11, this embodiment includes a rotational restraint member 68 that is disposed radially outside drive ribbon 70. Tabs 72 on rotational restraint member 68 engage axially extending slots 73 defined within the extended portion of drive ribbon 70 to define an engagement location 75. Restraint member 68 is fixed relative to the housing and the housing can also support a medication container without relative movement between the housing and the container. Thus, tabs 72 prevent rotation of the extended portion of drive ribbon 70 relative to the housing and the medication container. As a result, bearing member or foot 74 can be fixed to drive ribbon 70.

Thrust member 76 includes at least one helical thread 78 that engages a groove 80 that forms a helical shape on the extended portion of drive ribbon 70. As thrust member 76 and thread 78 rotate, they pull and guide drive ribbon 70 from its retracted configuration 69 into its extended configuration 71. Thread 78 also exerts an axial force on ribbon 70 whereby ribbon 70 can exert a biasing force on a medication container piston via foot 74 to dispense medication.

Thrust member 76 is axially stationary and rotatably mounted to restraint member 68. More specifically, thrust member 76 is rotatable relative to rotational restraint member 68 and axially captured by, and cannot move axially relative to, rotational restraint member 68. This is best understood with reference to FIG. 11. Thrust member 76 includes an axially extending cylindrical section 77 on which helical thread 78 is located. A radially extending flange 79 is located at one end of section 77. Rotational restraint member 68 includes an annular groove 67 which receives flange 79 that, once inserted into groove 67 prevents thrust member 76 from being moved axially relative to restraint member 68. The engagement of thrust member 76 with rotational restraint member 68 is a snap-fit type engagement that is facilitated by the inclined outer radial surface 79A of flange 79. Surface 79 acts as a camming ramp biasing flange 79 radially inwardly during engagement of thrust member 76 with rotational restraint member 68.

A drive gear or other suitable drive member engages thrust member 76, such as on the outer radial surface 76A of thrust member 76, to drivingly rotate thrust member 76. For example, outer radial surface 76A could be a geared surface that engages a motor driven gear to thereby rotate thrust member 76.

Figure 12:
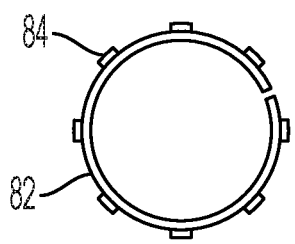
FIG. 12 is a schematic end view of an exemplary drive ribbon that does not rotate as it extends.
Figure 13:
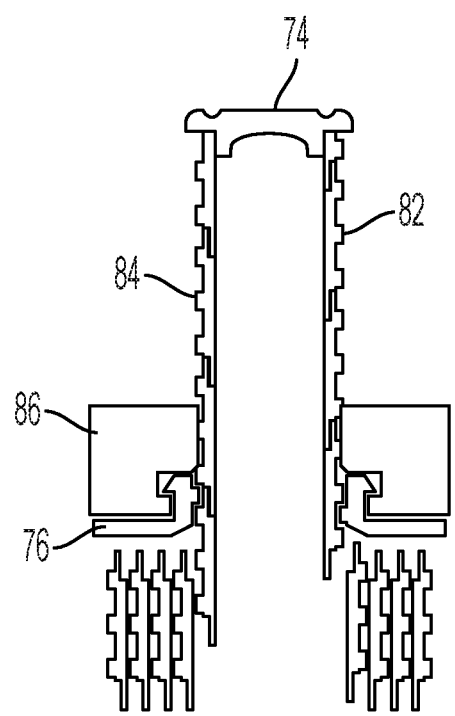
FIG. 13 is a schematic side view of a drive assembly with the drive ribbon of FIG. 12.

The embodiment of FIGS. 12 and 13 has the same general structure as the embodiment of FIGS. 10 and 11. The embodiment of FIGS. 12 and 13 differs, however, in that drive ribbon 82 has externally extending tabs or posts 84 which engage axially extending slots in rotational restraint member 86 to prevent rotation of drive ribbon 82. The use of tabs 84 avoids the use of axially aligned slots on the drive ribbon which may be difficult to form using a roll forming process.

Figure 14:
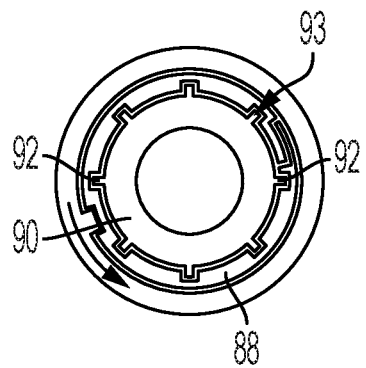
FIG. 14 is a schematic end view of another drive assembly with a non-rotating drive ribbon.
Figure 15:
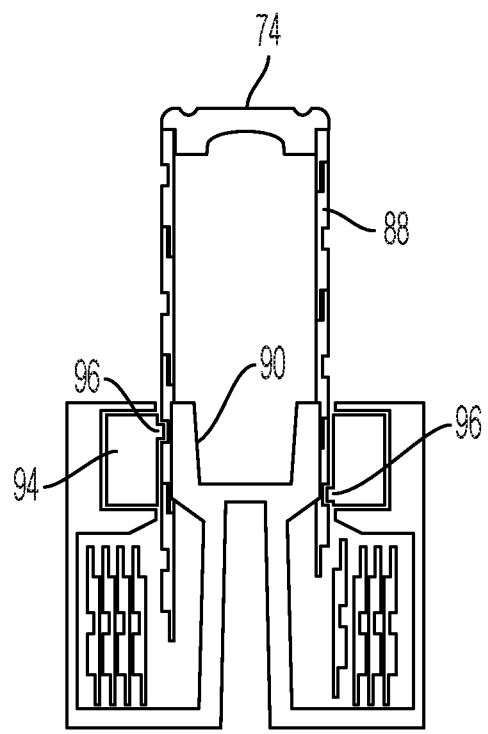
FIG. 15 is a schematic side view of an exemplary drive assembly with the drive ribbon of FIG. 14.

The embodiment of FIGS. 14 and 15 has a drive ribbon 88 with a groove on its external surface that takes a helical shape on the extended portion of the drive ribbon 88. Ribbon 88 also has grooves on its inner surface that extend axially in the extended portion of the ribbon.

Rotational restraint member 90 is disposed radially inside of drive ribbon 88 and includes axially extending ribs 92 that engage the grooves on the inner surface of ribbon 88 to define the engagement location 93 to prevent rotation of the extended portion of drive ribbon 88.

An axially stationary thrust member 94 is disposed radially outside of drive ribbon 88 and includes a helical thread 96 that engages the groove on the external surface of ribbon 88 that takes a helical shape on the extended portion of rib 88. As thrust member 94 rotates, it pulls ribbon 88 from its retracted configuration into its extended configuration and can exert an axial force on drive ribbon 88.

Figure 16:
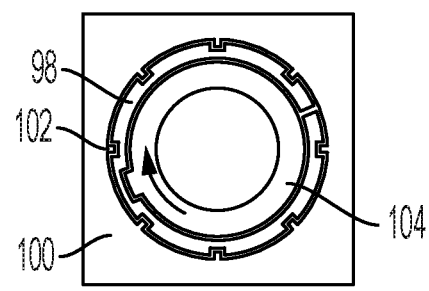
FIG. 16 is a schematic end view of another drive assembly with a non-rotating drive ribbon.
Figure 17:
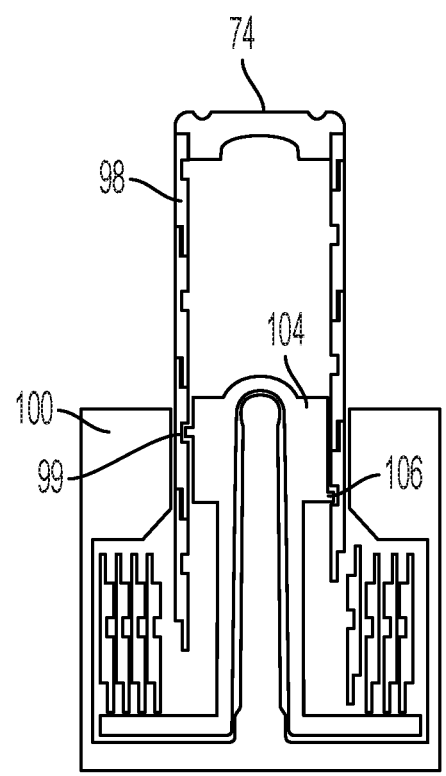
FIG. 17 is a schematic side view of the drive assembly of FIG. 16.

The embodiment of FIGS. 16 and 17 has a drive ribbon 98 having an internal groove 99 that defines a helical shape in the extended portion of the drive ribbon and external grooves that extend axially in the extended portion of the drive ribbon.

Rotational restraint member 100 is disposed radially outside ribbon 98 and includes ribs 102 that engage axially extending external slots on ribbon 98 to define the engagement location to prevent rotation of ribbon 98. An axially stationary thrust member 104 is rotatably mounted on a shaft and includes a helical thread 106. Thrust member 104 and thread 106 rotate and, as they rotate, pull ribbon 98 into the extended configuration. Thread 106 also exerts axial forces on ribbon 98.

Figure 18:
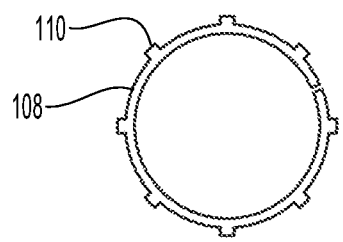
FIG. 18 is a schematic end view of a drive ribbon having elongate ribs.
Figure 19:
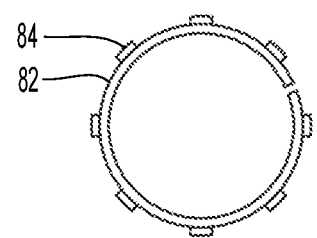
FIG. 19 is a schematic end view of a drive ribbon with isolated posts.

FIGS. 18 and 19 schematically depict two drive ribbons 108, 82 which include radially outward extending projections that engage slots in a rotational restraint member to prevent rotation of the ribbon. Drive ribbon 82 includes a plurality of outwardly extending tabs 84 that are separate both axially and circumferentially as can also be seen in FIGS. 12 and 13. Drive ribbon 108 of FIG. 18 has elongate ribs 110 that are separated circumferentially but which are substantially continuous in the axial direction for the extended portion of the drive ribbon.

Non-Rotating Drive Ribbon with Axially Movable Thrust Member

In some embodiments having a non-rotating drive ribbon, the thrust member moves axially in a proximal direction P as it is rotated and a distal end of the drive ribbon remains axially stationary as the thrust member rotates. To advance the piston within the container body, the thrust member and an extended portion of the drive ribbon are axially moved in a distal direction D, opposite to the proximal direction. Examples of such devices shown in FIGS. 20 and 21. Orientation using proximal and distal is consistent throughout this disclosure.

The device may further include a drive spring which is tensioned as the thrust member is rotated to extend the drive ribbon. As the ribbon is extended, the thrust member moves axially in the proximal direction and the distal end of drive ribbon remains stationary. To initiate a dispensing of medication, the thrust member and drive spring are released and the drive spring axially advances the thrust member together with the extended portion of the drive ribbon. The drive ribbon thereby advances the piston in the medication container to dispense the medication.

Figure 20:
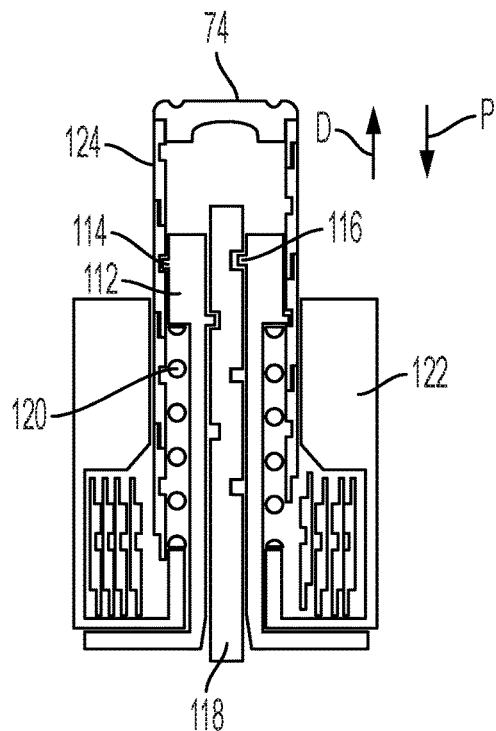
FIG. 20 is a schematic side view of an exemplary drive assembly with a non-rotating drive ribbon.

The embodiment of FIG. 20 has an axially movable thrust member 112, the thrust member 112 includes a helical thread 114 engageable with the drive ribbon 124 wherein the helical thread 114 is disposed radially inside of the drive ribbon 124 at the location where the helical thread engages the drive ribbon. Rotational restraint member 122 is rotationally fixed relative to the housing and engaged with the drive ribbon 124 such that the engagement of the drive ribbon and the rotational restraint member prevents relative rotation of the extended portion of the drive ribbon 124 and the rotational restraint member 122.

Thread 114 of thrust member 112 engages a helical groove on the inward facing surface of drive ribbon 124. Thrust member 112 has a hollow center which defines a central bore for receiving center shaft 118. Thrust member 112 has a helical thread 116 facing its central bore that engages a helical groove on shaft 118. As thrust member 112 is rotated to move proximally on shaft 118 it compresses drive spring 120. FIG. 20 shows thrust member in its most proximal position.

Shaft 118 can extend proximally of the drive assembly further than that shown in FIG. 20 and engage a locking mechanism that prevents the axial movement of shaft 118.

After rotating thrust member 112 to move in the proximal direction and compress spring 120, shaft 118 can be released thereby also releasing thrust member 112 and spring 120. Spring 120 will then bias thrust member 112 distally and thread 114 on thrust member 112 will cause drive spring 120 to advance distally with thrust member 112.

Figure 21:
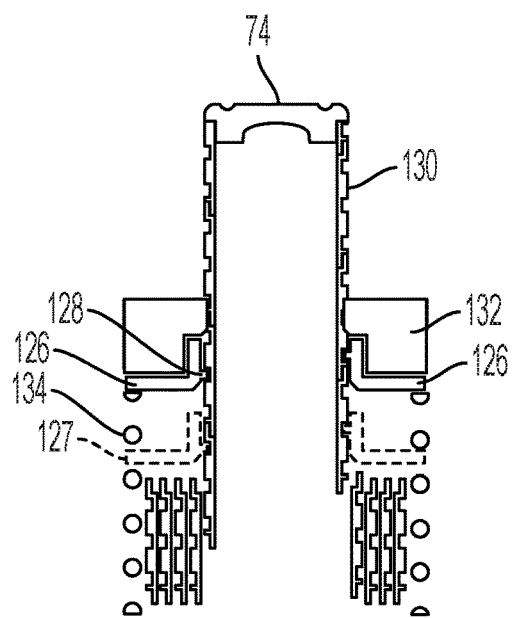
FIG. 21 is a schematic side view of another drive assembly with a non-rotating drive ribbon.

The embodiment of FIG. 21 includes an axially movable thrust member 126, the thrust member includes a helical thread 128 engageable with the drive ribbon 130 wherein the helical thread 128 is disposed radially outside of the drive ribbon 130 at the location where the helical thread engages the drive ribbon. Rotational restraint member 132 is rotationally fixed relative to the housing and engaged with the drive ribbon 130 such that the engagement of the drive ribbon 130 and the rotational restraint member 132 prevents relative rotation of the extended portion of the drive ribbon 130 and the rotational restraint member 132.

Thrust member 126 may extend radially outwardly to a greater extent than is shown in FIG. 21 such that it threadingly engages the housing in a releasable manner. As thrust member 126 is rotated relative to the housing, it will move in a proximal direction and compress drive spring 134. Reference numeral 127 is used in FIG. 21 to identify the location of thrust member 126 after it has been rotated to proximally retract the thrust member. After retracting the thrust member 126, it can be released, which will also release drive spring 134 whereby spring 134 will axially advance thrust member 126 in the distal direction. Thread 128 on thrust member 126 will cause drive ribbon 130 to axially advance in the distal direction with thrust member 126 and thereby advance a medication container piston to dispense medication.

Rotatable Drive Ribbon

FIGS. 22-45 relate to drive ribbons that rotate as they are axially advanced. Such ribbons may be employed in a medication delivery device for use with a container having a container body holding a medication and defining an outlet wherein the container includes a piston disposed within the container body and advancement of the piston within the container body expels medication through the outlet. The delivery device includes a housing adapted to couple with the container and a drive assembly coupled with the housing and adapted to advance the piston within the container. The drive assembly includes a drive ribbon having a distal edge section and a proximal edge section. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally movable from the retracted configuration to the extended configuration and movement of the drive ribbon from the retracted configuration to the extended configuration defines a drive axis. The drive ribbon rotates as it is moved from the retracted configuration to the extended configuration.

Figure 22:
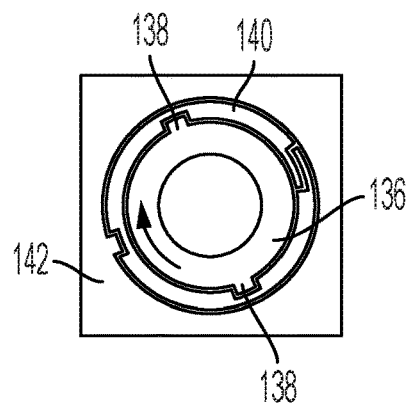
FIG. 22 is a schematic end view of an exemplary drive assembly that includes a drive ribbon that rotates as it extends axially.
Figure 23:
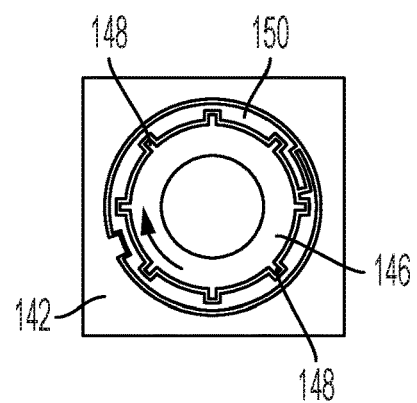
FIG. 23 is a schematic end view of another drive assembly that includes a drive ribbon that rotates as it extends axially.
Figure 24:
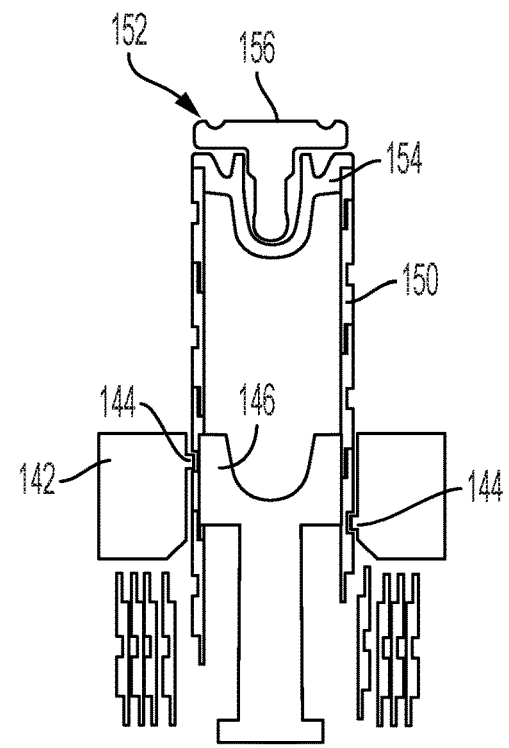
FIG. 24 is a schematic side view of the drive assembly of FIG. 23.

FIGS. 22-24 relate to devices wherein a drive member is disposed radially inside the drive ribbon to engage and rotate the drive ribbon and a fixed component having a helical thread is disposed radially outside the drive ribbon. The helical thread of the fixed component engages the drive ribbon and controls the movement of the drive ribbon between the retracted configuration and the extended configuration.

FIG. 22 illustrates an assembly wherein drive member 136 has a pair of keys 138 that engage grooves on the inner facing surface of drive ribbon 140 to drivingly rotate ribbon 140. Collar 142 is fixed relative to the housing and includes a helical thread 144 that engages a helical groove on the outer facing surface of drive ribbon 140.

FIGS. 23 and 24 illustrate an assembly very similar to that shown in FIG. 22 but wherein the drive member 146 has a larger number of keys 148 to engage a corresponding larger number of grooves on the inner surface of drive ribbon 150 to define the engagement locations.

Because drive ribbon 150 rotates as it is axially advanced, a rotatable bearing assembly 152 having a first member 154 fixed to the drive ribbon 150 and a second member 156 that can rotate relative to member 154 and ribbon 150 is employed. Second member 156 can bear directly against the piston of a medication container without rotating relative to the piston while first member 154 and ribbon 150 both rotate relative to member 156 and the piston as the ribbon is advanced and biases member 156 against the piston to advance the piston.

Figure 25:
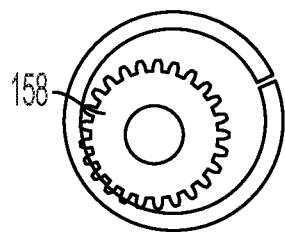
FIG. 25 is a schematic end view of a drive assembly having an internal gear drive for rotating a drive ribbon.
Figure 26:
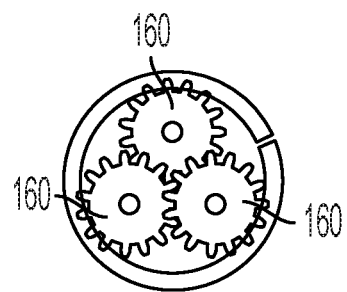
FIG. 26 is a schematic end view of another drive assembly having an internal gear drive for rotating a drive ribbon.

FIGS. 25 and 26 illustrate alternative drive arrangements that are disposed radially within the drive ribbon to engage and rotate the drive ribbon. FIG. 25 shows the use of a single gear member 158 while FIG. 26 shows the use of a plurality of gears 160. Gears 158, 160 would engage axially extending grooves or raised ribs (not shown) on the inner surface of the drive ribbon. Such grooves/ribs would be spaced apart by a distance corresponding to the distance between the gear teeth on the gears being used with the ribbon.

FIGS. 27-41 relate to embodiments having a rotatable drive ribbon wherein a drive member disposed radially outside the drive ribbon engages and drivingly rotates the drive member.

Figure 27:
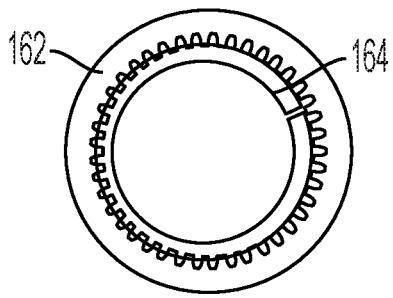
FIG. 27 is a schematic end view of a drive assembly having an external gear drive for rotating a drive ribbon.
Figure 28:
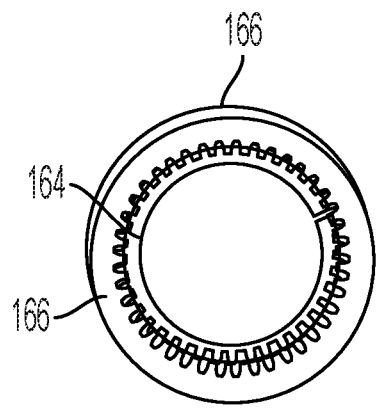
FIG. 28 is a schematic end view of another drive assembly having an external gear drive for rotating a drive ribbon.
Figure 29:
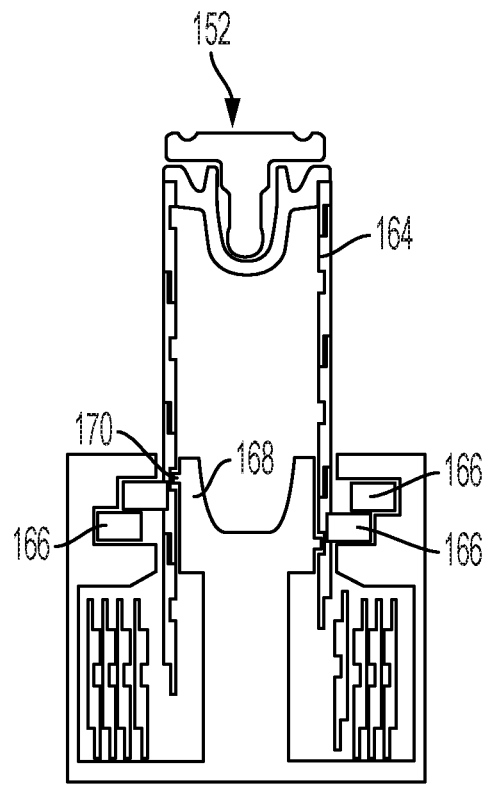
FIG. 29 is a schematic side view of the drive assembly of FIG. 28.

FIG. 27 schematically depicts the use of a single ring gear 162 with a drive ribbon 164. Ring gear 162 completely surrounds drive ribbon 164 and engages a portion of the outer surface of the drive ribbon 164. The central opening of ring gear 162 is larger than the outer diameter of drive ribbon 164 and, thus, a portion of the outer circumference of the drive ribbon is not engaged by ring gear 162. FIGS. 28 and 29 schematically depict the use of a plurality of ring gears. In the illustrated embodiment, two ring gears 166 engage a drive ribbon 164. The use of two ring gears 166 allows the full outer circumference of the drive ribbon 164 to be engaged by a ring gear. As can be seen in FIG. 29, the ring gears 166 are axially offset. The device of FIG. 29 also includes a spindle member 168 having a helical thread 170 which engages a groove on the inner surface of drive ribbon 164. Ring gears 166 are advantageously axially positioned such that the ring gears 166 engage the outer surface of the drive ribbon proximate to the location where thread 170 engages the inner surface of the drive ribbon.

Figure 30:
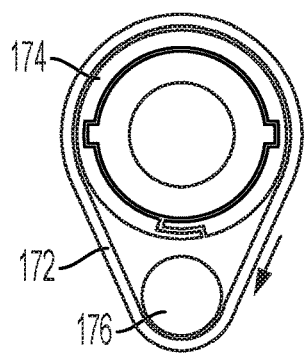
FIG. 30 is a schematic end view of a drive assembly having an external belt drive.

Various other types of drive members may alternatively be employed to drivingly rotate a drive ribbon. FIG. 30 schematically depicts the use of a belt drive arrangement wherein a belt 172 engages the outer surface of a drive ribbon 174 to rotate the drive ribbon. A driven shaft 176, or other suitable mechanism, drives belt 172.

Figure 31:
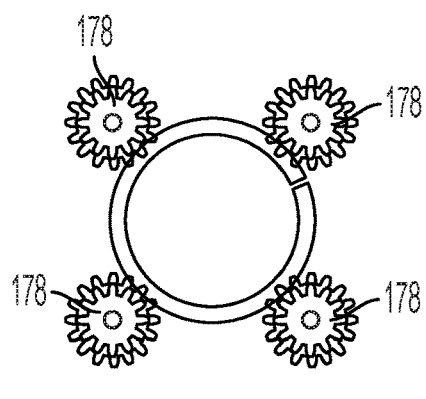
FIG. 31 is a schematic end view of a drive assembly having a plurality of external gears for rotating the drive ribbon.
Figure 32:
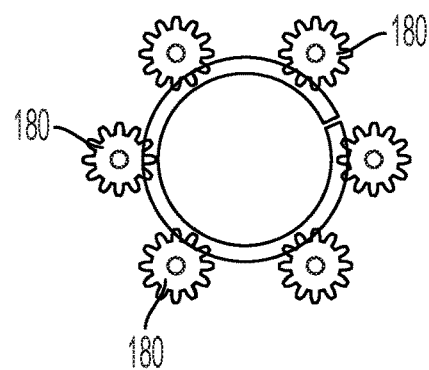
FIG. 32 is a schematic end view of another drive assembly having a plurality of external gears for rotating the drive ribbon.
Figure 33:
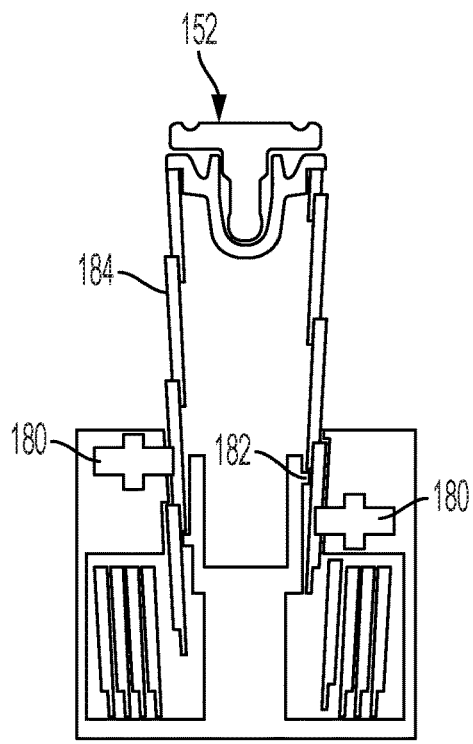
FIG. 33 is a schematic side view of the drive assembly of FIG. 32.

A plurality of planet gears may also be employed to rotate the drive ribbon. FIG. 31 depicts the use of planetary gears 178 that are also reducing gears while FIGS. 32 and 33 depict a slightly different embodiment with planetary gears 180 that are not reducing gears. As can be seen in FIG. 33, a helical thread 182 engages the inwardly projecting proximal edge of drive ribbon 184 while planetary gears 180 engage the outer surface of drive ribbon 184. Similar to the drive ribbon of FIGS. 7-9, drive ribbon 184 has outwardly projecting edges where the drive ribbon engages with itself.

Figure 34:
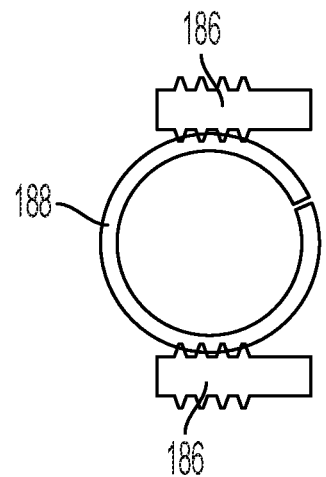
FIG. 34 is a schematic end view of an external worm gear drive.
Figure 35:
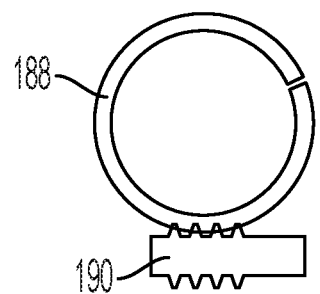
FIG. 35 is a schematic end view of another external worm gear drive.

FIGS. 34 and 35 depict alternative drive arrangements that employ worm gears to rotate the drive ribbon. In FIG.

34 a pair of worm gears 186 engage the outer surface of drive ribbon 188 to rotate ribbon 188. FIG. 35 depicts a drive arrangement where a single worm gear 190 is used to rotate drive ribbon 188. While the use of a single worm gear would reduce the complexity and number of parts compared to the use of two worm gears, the use of a pair of worm gears disposed on opposite sides of the drive ribbon provides a more balanced force distribution on the drive ribbon.

Figure 36:
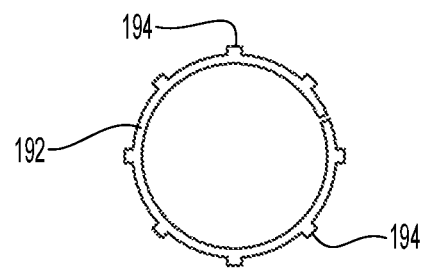
FIG. 36 is a schematic end view of a drive ribbon with external ribs.
Figure 37:
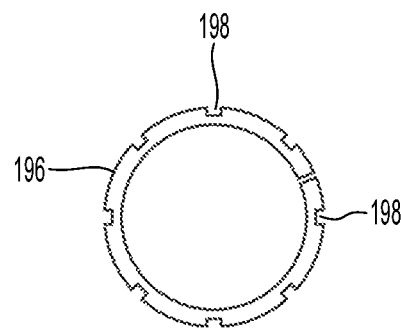
FIG. 37 is a schematic end view of a drive ribbon with external slots.

FIGS. 36-41 relate to the use of a key drive to drivingly rotate the drive ribbon. FIG. 36 depicts a drive ribbon 192 having a plurality of keys or ribs 194 that extend axially when the drive ribbon 192 is in an extended configuration. Ribs 194 can be engaged by keyways or slots on a drive member to drivingly rotate ribbon 192. FIG. 37 depicts a drive ribbon 196 having a plurality of keyways or slots 198 that extend axially when the drive ribbon 196 is in an extended configuration. Slots 198 can be engaged by keys or similar projections on a drive member to drivingly rotate ribbon 196.

Figure 38:
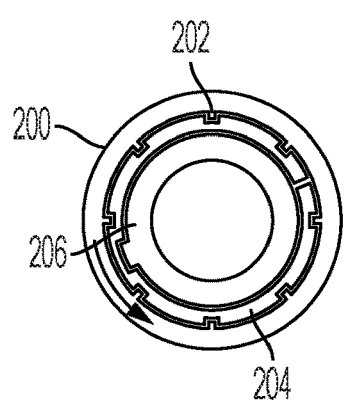
FIG. 38 is a schematic end view of a drive assembly having a drive ribbon with external slots and key drive.
Figure 39:
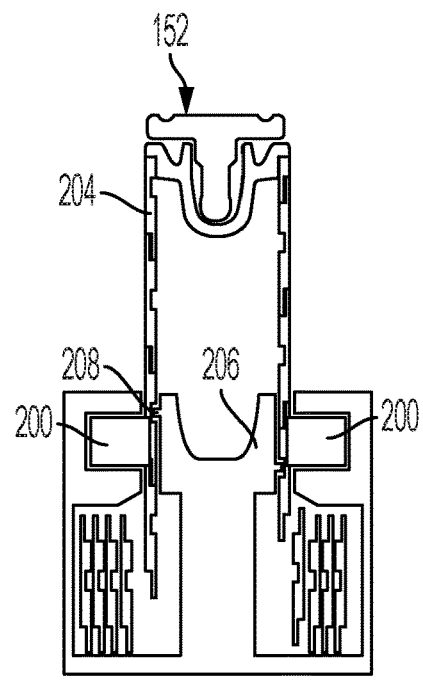
FIG. 39 is a schematic side view of the drive assembly of FIG. 38.

FIGS. 38 and 39 depict an example of a key drive arrangement. In FIGS. 38 and 39, drive member 200 has a plurality of ribs or keys 202 that engage axially extending slots on the outer surface of drive ribbon 204. As drive member 200 is rotated, drive ribbon 204 is also rotated. A stationary spindle member 206 has a helical thread 208 which engages a groove on the inner surface of drive ribbon 204.

Figure 40:
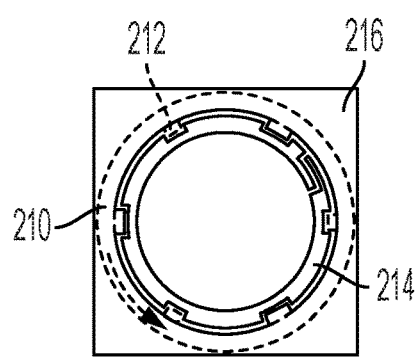
FIG. 40 is a schematic end view of another drive assembly having a drive ribbon with external slots and a key drive.
Figure 41:
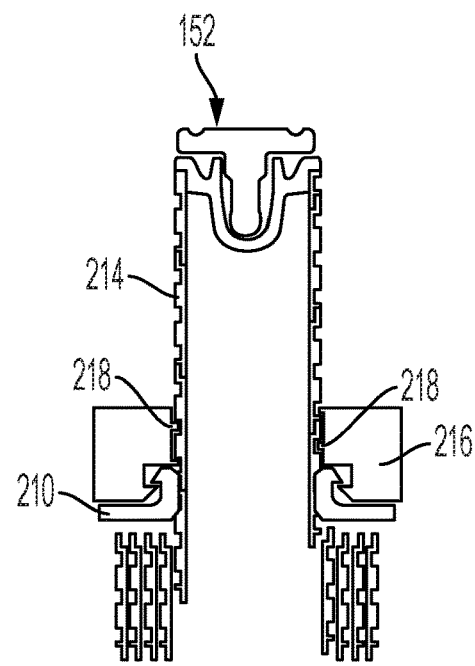
FIG. 41 is a schematic side view of the drive assembly of FIG. 40.

FIGS. 40 and 41 depict another example of a key drive arrangement. In this arrangement drive member 210 includes a plurality of ribs or keys 212 that engage axially extending slots on the outer surface of drive ribbon 214 to drivingly rotate ribbon 214. A stationary collar member 216 includes a helical thread 218 that engages a groove on the outer surface of drive ribbon 214.

Non-Engaged Portion of Drive Ribbon is Engaged by Drive Member

FIGS. 42-45 relate to a medication delivery device for use with a container having a container body holding a medication and defining an outlet. The container includes a piston disposed within the container body wherein advancement of the piston within the container body expels medication through the outlet. The delivery device includes a housing adapted to couple with the container and a drive assembly coupled with the housing and adapted to advance the piston within the container. The drive assembly includes a drive ribbon having a distal edge section and a proximal edge section. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally movable from the retracted configuration to the extended configuration. Movement of the drive ribbon from the retracted configuration to the extended configuration defines a drive axis and advances the piston within the container body. The drive ribbon rotates as it is moved from the retracted configuration to the extended configuration. The drive ribbon also defines a transition portion disposed between the retracted portion and the extended portion wherein the distal edge section and proximal edge section of the drive ribbon are not engaged together in the transition portion. A drive member engages the drive ribbon and drivingly rotates the drive ribbon and the drive member is engaged with the retracted portion or the transition portion of the drive ribbon.

Storage Bobbin Drive Member

Figure 42:
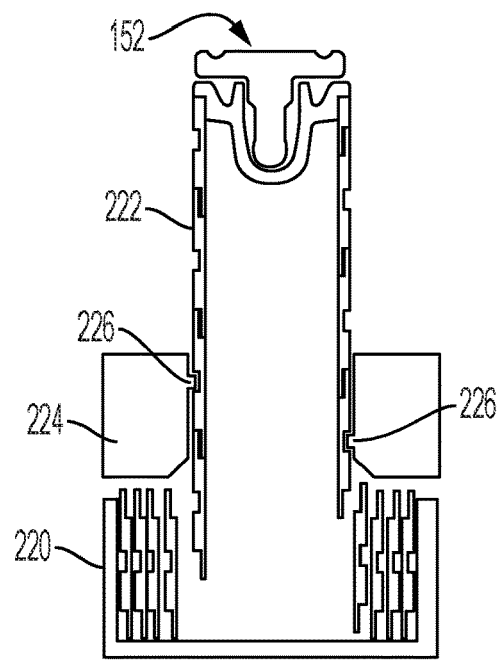
FIG. 42 is a schematic side view of a drive assembly wherein the retracted portion of the drive ribbon is driven by the bobbin.

FIG. 42 depicts a device which includes a storage bobbin 220 which holds the retracted portion of drive ribbon 222. That portion of the drive ribbon 222 disposed within storage bobbin 220 expands radially outward to engage storage bobbin 220. Thus, as storage bobbin 220 is rotated, drive ribbon 222 is also rotated. This can be used to force drive ribbon 222 into engagement with collar member 224. Collar member 224 includes a helical thread 226 which engages a groove on the outer surface of drive ribbon 222 to control and guide ribbon 222 into engagement with itself to thereby axially extend ribbon 222. It is noted that rotation of bobbin 220 in the opposite direction can be used to retract ribbon 222. Similarly, for nearly all of the drive member mechanisms disclosed herein, unless it is specifically stated otherwise, the drive member mechanisms can be operated in reverse to retract the drive ribbon as well as extend it.

Reciprocating Drive Member

Figure 43:
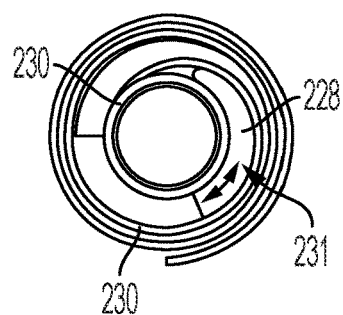
FIG. 43 is a schematic end view of a drive assembly with a reciprocating drive member.

FIG. 43 illustrates a reciprocating drive member 228 that engages drive ribbon 230 in a transition portion 231 of the drive ribbon between the retracted portion and the extended portion. As can be seen in FIG. 43, reciprocating drive member 228 engages a radially inward facing surface of drive ribbon 230. For some embodiments of drive member 228, the cyclic motion of member 228 and the nature of its engagement will result in member 228 being able to drive the ribbon 230 into its extended position but unable to drive ribbon 230 into its retracted position.

Worm Gear

Figure 44:
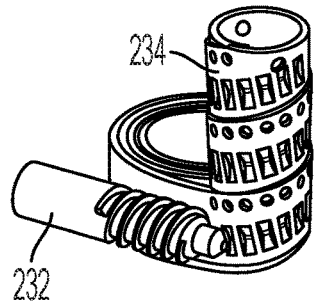
FIG. 44 is a schematic perspective view of a drive assembly with a worm gear.

FIG. 44 depicts an embodiment where a worm gear 232 engages a drive ribbon 234 in the retracted portion of the drive ribbon.

Reciprocating Ratchet Drive

Figure 45:
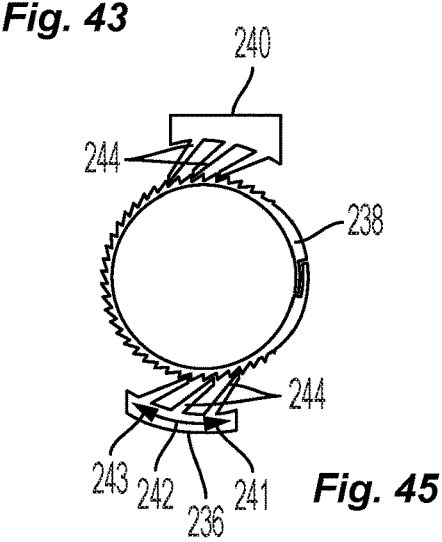
FIG. 45 is a schematic end view of a drive assembly with reciprocating drive members having a plurality of ratchet members.

Referring now to FIG. 45, for embodiments having a reciprocating drive member, the reciprocating drive member 236 may take the form of a drive member that moves in a first direction and an opposite second direction, as depicted by double headed arrow 242. The drive member 236 is shown including at least one flexible ratchet member 244 engageable with the drive ribbon 238 configured to allow relative movement between the drive member 236 and the drive ribbon 238 in the first direction 243 and not allow relative movement between the drive member 236 and the drive ribbon 238 in the second direction 241 (or allow unidirectional movement). When moving in the second direction 241, the drive member 236 will push the drive ribbon and thereby cause the drive ribbon 238 to move. When moving in the first direction 243, the ratchet member 236 will be repositioned on the drive ribbon 238 whereby it can push the ribbon forward when once again moving in the second direction 241. The illustrated embodiment also includes a stationary ratchet member 240 which does not move relative to the housing and which includes a plurality of ratchet members 244 engaging the radially outward facing surface of drive ribbon 238. When the reciprocating drive member 236 is being moved in the first direction 243, ratchet member 240 will ensure that drive ribbon 238 is not pulled rearwards with reciprocating ratchet member 236. The ratchet drive depicted in FIG. 45 is well suited for use in a single-use device where the ribbon is extended but is not later retracted. If it was desired to use such a ratcheting drive in a multi-use device, ratchet members 236 and 240 would have to be movable out of engagement with the drive ribbon and a second driving mechanism employed to rotate the drive ribbon in the opposite direction. For generating the reciprocating movement of drive member 236, as well as drive member 228 discussed above, an oscillating escapement drive can be employed.

Device Architecture

The various ribbons and drive member mechanisms disclosed herein can be combined in numerous ways to provide a medication delivery device. Two general categories of such devices include those having an inline architecture and those having a dual axis architecture. These two basic architectures are depicted in FIGS. 46-54.

Inline Architecture

Figure 46:
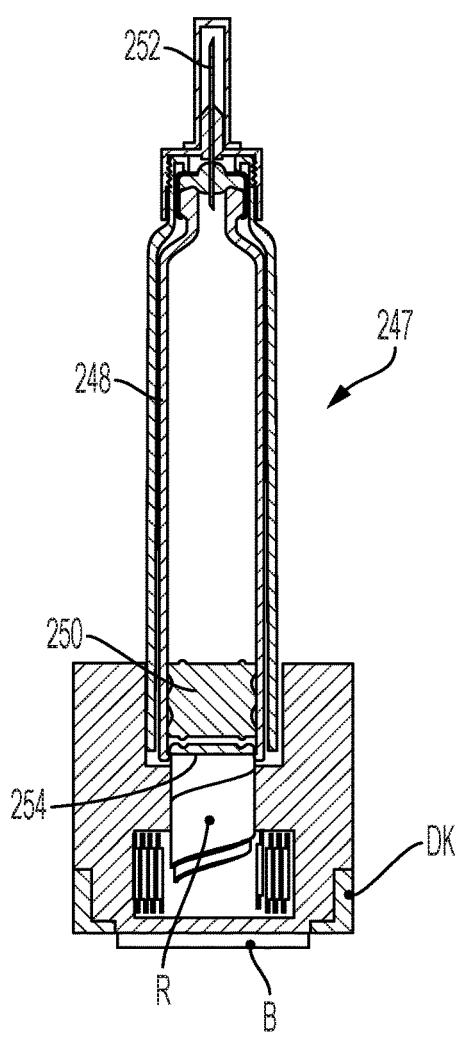
FIG. 46 is a schematic view of an exemplary device having an inline drive assembly.
Figure 47:
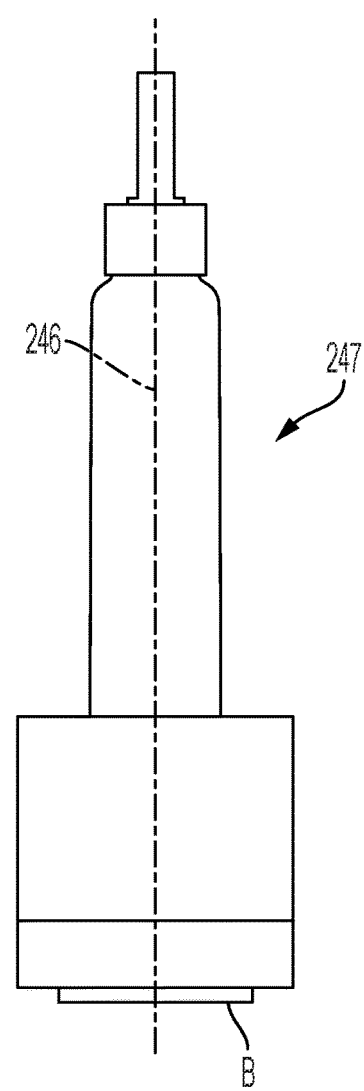
FIG. 47 is a side view of the device of FIG. 46.
Figure 48:
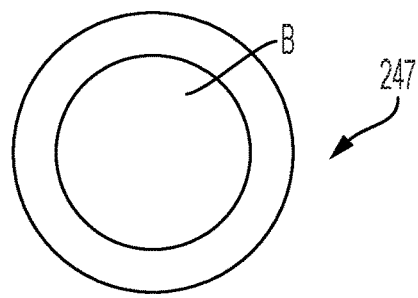
FIG. 48 is an end view of the device of FIG. 47.

A device having an inline architecture is depicted in FIGS. 46-48. In this arrangement, the drive ribbon R and the drive member mechanism used to drive the extension of the drive ribbon both share a common axis 246. As shown in FIG. 46, the device includes a dialing knob DK that is used to set the dosage and an inject button B that initiates the extension of the drive ribbon. The device also holds a medication container 248. The illustrated container 248 is a conventional syringe cartridge having a glass barrel that holds the medication, a piston 250 disposed within the barrel and an outlet defined by hollow injection needle 252. As the drive ribbon R extends, a bearing member 254 disposed on the distal end of the ribbon R bears against piston 250 to advance piston 250 within container 248 and thereby expel medication through needle 252.

Dual Axis Architecture

Figure 132:
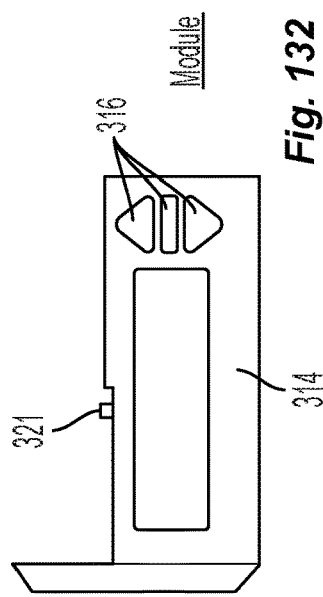
FIG. 132 is a side view of the drive member mechanism module of FIG. 128.
Figure 127:
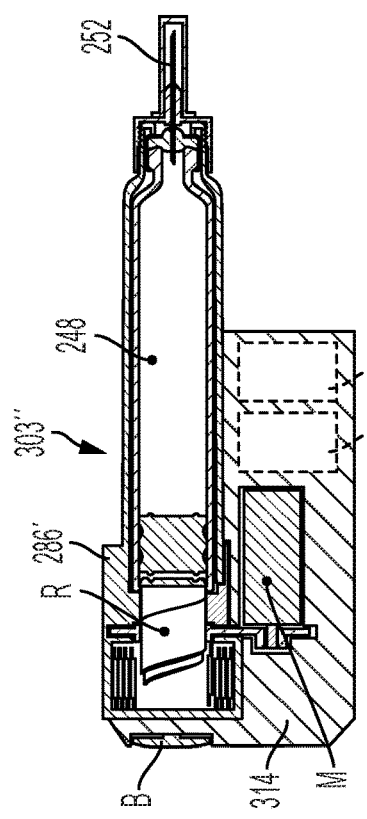
FIG. 127 is a schematic view of an exemplary device having a separable cassette and drive module.
Figure 130:
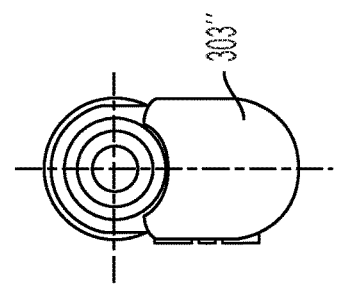
FIG. 130 is an end view of the device of FIG. 128.
Figure 129:
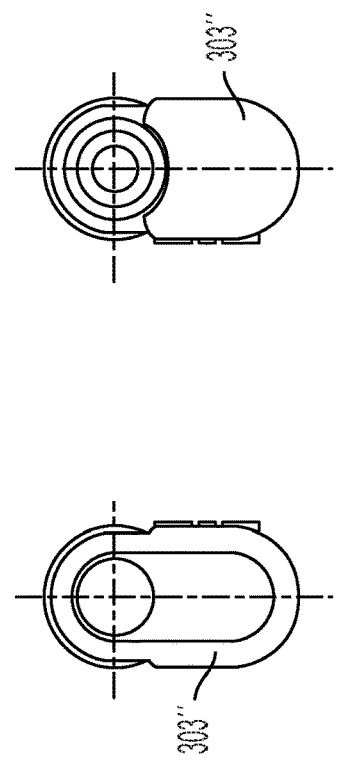
FIG. 129 is an end view of the device of FIG. 128.

FIGS. 49-54 provide simplified depictions of a dual axis device. FIGS. 55-132 provide more detailed schematic images of dual axis devices and the figures which follow FIG. 132 provide even further representations of dual axis devices. References to common components, such as the needle 252, container 248, the dialing knob DK, drive ribbon R and inject button B, will be used for different device configurations throughout the figures. As will become evident from the discussion which follows, dual axis devices include a primary drive axis defined by the drive ribbon and also include a drive member mechanism that defines a secondary axis that is parallel to and offset from the primary drive axis. One advantage of a dual axis device is that by offsetting part of the drive member mechanism from the primary axis, the drive member mechanism can be positioned to extend parallel to the primary axis in the distal direction. This allows such dual axis devices to have an overall shorter length than if the entirety of the drive member mechanism was located in alignment with the primary axis.

Figure 49:
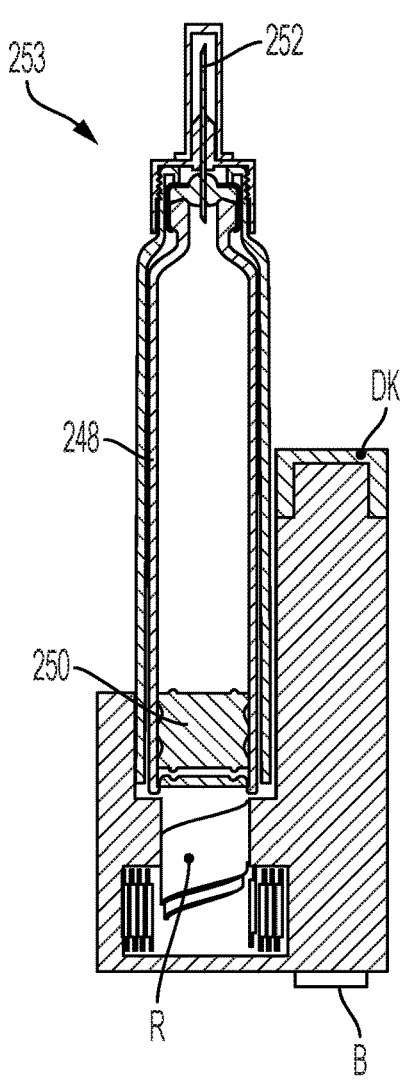
FIG. 49 is a schematic view of an exemplary device having a secondary axis.
Figure 50:
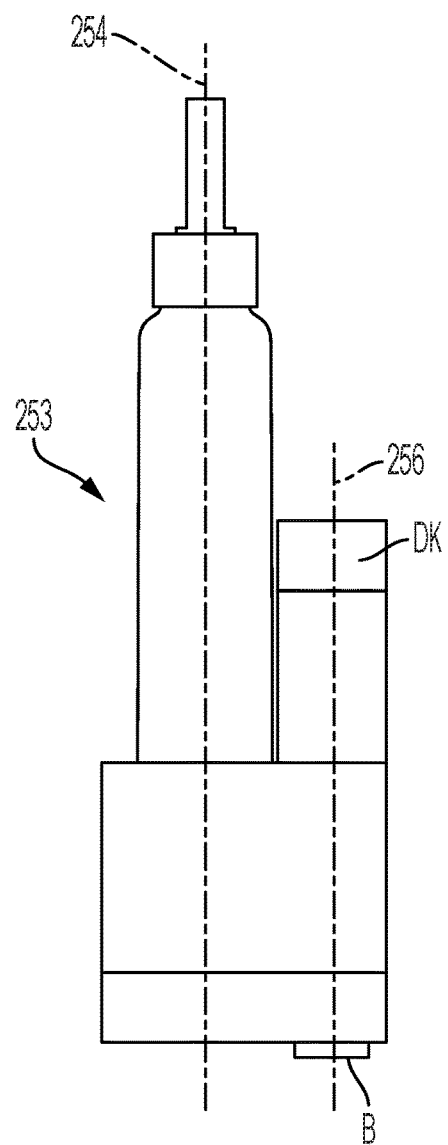
FIG. 50 is a side view of the device of FIG. 49.
Figure 51:
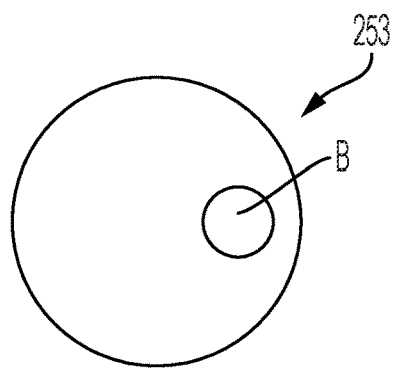
FIG. 51 is an end view of the device of FIG. 50.
Figure 79:
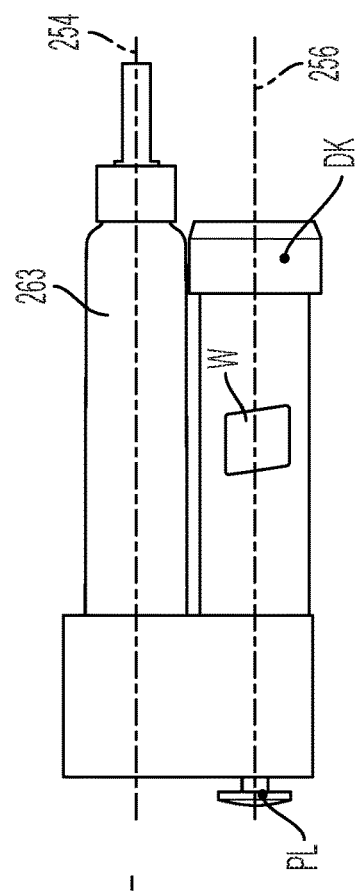
FIG. 79 is a schematic view of an exemplary device having a secondary axis.
Figure 81:
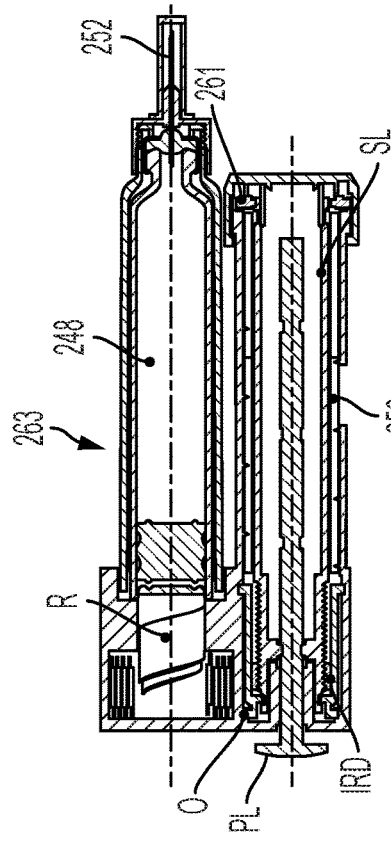
FIG. 81 is an end view of the device of FIG. 80.
Figure 80:
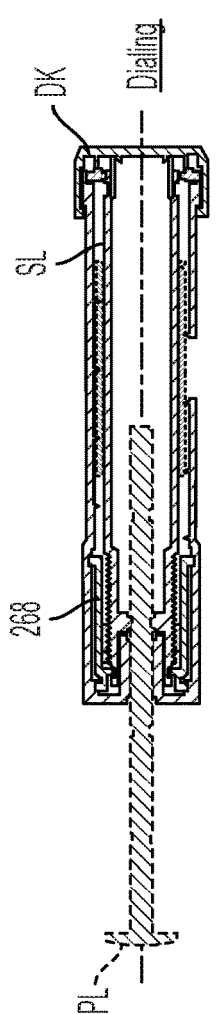
FIG. 80 is a side view of the device of FIG. 79.
Figure 82:
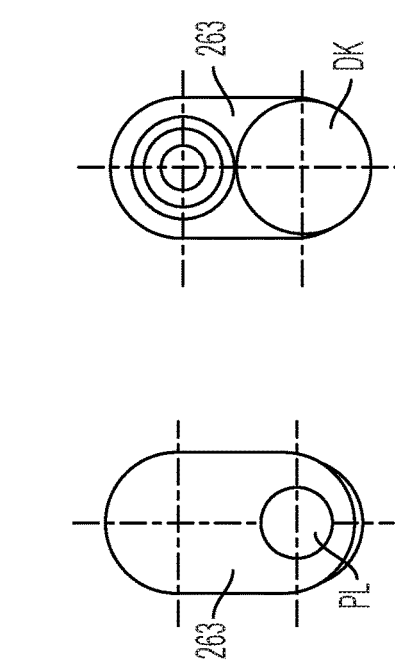
FIG. 82 is an end view of the device of FIG. 80.

As can be seen in FIGS. 49-54, the dual axis architecture can increase the bulk of the device, referred to here as 253, over part of the relatively shorter length of the device, which may be beneficial to patient users with dexterity or handling challenges due to a debilitating disease or condition. The device 253 depicted in FIGS. 49-51 is used to dispense medication from a conventional 3 ml syringe cartridge and has a drive ribbon defining a first primary axis 254 and a drive member mechanism that defines a secondary parallel axis 256. Similarly, the device, referred to here as 253', depicted in FIGS. 52-54 also dispenses medication from a conventional 3 ml syringe cartridge and has a drive ribbon defining the first primary axis 254 and a drive member mechanism that defines the secondary parallel axis 256. The housings of the two components (cartridge/drive ribbon portion and drive member mechanism component portion) may have different housing configurations.

Both of these devices, as wells as the devices which are depicted in FIGS. 55-132, are a medication delivery device for use with a container having a container body holding a medication and defining an outlet. The container includes a piston disposed within the container body wherein advancement of the piston within the container body expels medication through the outlet. The delivery device includes a housing adapted to couple with the container and a drive assembly coupled with the housing and adapted to advance the piston within the container. The drive assembly includes a drive ribbon having a distal edge section and a proximal edge section. The drive ribbon has a retracted configuration and an extended configuration wherein a retracted portion of the drive ribbon in the retracted configuration defines a spiral and an extended portion of the drive ribbon in the extended configuration defines a helix. The drive ribbon is incrementally movable from the retracted configuration to the extended configuration. Movement of the drive ribbon from the retracted configuration to the extended configuration defines a drive axis and advances the piston within the container body. A drive member mechanism is operably coupled with the drive ribbon and defines a secondary axis parallel with the drive axis. The drive member mechanism generates a force that is transferred to the drive ribbon to move the drive ribbon from the retracted configuration to the extended configuration.

Several embodiments of such dual axis devices will now be discussed. The various embodiments include several illustrated examples, such as those depicted in FIGS. 55-78 and 97-114, which have a drive member mechanism that includes a spring S aligned with the secondary axis wherein setting a dose includes tensioning the spring S and releasing the tension from the spring S generates the force that is transferred to the drive ribbon R to move the drive ribbon from the retracted configuration to the extended configuration.

Several of the illustrated dual axis embodiments, such as those depicted in FIGS. 79-96, have a drive member mechanism includes that a plunger disposed along the secondary axis wherein linear translation of the plunger generates the force that is transferred to the drive ribbon R to move the drive ribbon from the retracted configuration to the extended configuration.

Still other ones of the illustrated dual axis embodiments, such as those depicted in FIGS. 115-132, have a drive member mechanism that includes an electric motor M drivingly coupled with an element disposed along the secondary axis, the electric motor M generating the force that is transferred to the drive ribbon R to move the drive ribbon from the retracted configuration to the extended configuration. In such embodiments, the element disposed along the secondary axis may be a drive shaft of the electric motor.

In some of the illustrated embodiments, such as the embodiments of FIGS. 55-102 the drive ribbon R and the drive member mechanism are disposed within the housing and the container 248 is not removable from the housing whereby these devices form single-use or disposable prefilled devices. Modification of such devices, however, could adapt them for multiple use applications. Alternatively, the device may have a more modular architecture such as those depicted in FIGS. 103-136.

Turning now to the device, now referred to as device 253", depicted in FIGS. 55-60, this device includes the primary axis 254 and the secondary axis 256. A dialing knob DK on the secondary axis is used to set the dosage and tensions a torsion spring S by means of a ratcheting mechanism (dialing ratchet) DR which rotates a sleeve SL and the torsion spring S. The sleeve SL is coupled with the inject button B and when the inject button is pressed, the sleeve shifts, releasing the spring. When the spring S is released, it rotates an output sleeve 258 that has an output ratchet O disposed thereon. The output ratchet O, in turn, rotates the drive ribbon R. The output ratchet O engages a drive member that, in turn, engages and rotates either the ribbon or, if a non-rotating ribbon is used, a thrust member, such as described previously. Rotation of the drive ribbon, or thrust member, extends the ribbon axially and thereby advancing the piston and dispensing medication from the cartridge. A threaded member IRD is a "Turns-counting IRD" that functions as an insufficient remaining dosage indicator and prevents further rotation of the sleeve SL and, thus, the dialing knob DK after the member IRD has travelled the threaded length of the sleeve SL which is dimensioned to correspond to the quantity of medication in a 3 ml cartridge. FIG. 59 illustrates the device 253" when the dialing knob DK is being rotated to tension the torsion spring S, also referred to as a dialing configuration and set the dosage. Rotation of the dialing knob DK in turn rotates a dose indicator dial 259 which can be visible through a window W defined by the housing to provide indication of the amount dialed. FIG. 60 illustrates the device 253" during an injection procedure after the button is depressed by a user to release the spring S that rotates the sleeve 258.

The device 253A" depicted in FIGS. 61-66 is similar to that depicted in FIGS. 55-60 but the dialing knob DK of the embodiment of FIGS. 61-66 is located on the proximal end of the device with the inject button B instead of the distal end. Rotation of the dialing knob DK rotates the internal sleeves SL by means of a dialing ratchet 261. FIG. 65 illustrates the device 253A" being placed in the dialing configuration to set the dosage. FIG. 66 illustrates the device 253A" during the injection procedure after the button is depressed by a user.

The device 253''' depicted in FIGS. 67-72 has a drive ribbon R defining a primary axis 254 and a driving mechanism centered on a secondary axis 256. The drive member mechanism includes a dialing knob DK that is rotated by the user to set the dosage. Rotation of the dialing knob DK rotates an internal sleeves SL by means of a dialing ratchet 261. As the sleeve rotates SL, it tensions a torsion spring S. Depressing the inject button B moves a shift member 260 which shifts the sleeve and thereby releases the torsion spring. When the torsion spring is released, it rotates output sleeve 262. Output sleeve 262 has an output ratchet O disposed thereon which drives the ribbon assembly as output sleeve 262 is rotated. The input sleeve includes a threaded section on which a threaded member IRD (insufficient remaining dosage) is located.

The device 253"" depicted in FIGS. 73-78 also includes a shift member 264 to initiate the dispensing of medication in an injection procedure but it is configured differently than that of the embodiment of FIGS. 67-72. The embodiment of FIGS. 73-78 includes a dialing knob DK that is used to set the dosage. Rotation of the dialing knob DK rotates the sleeve SL by means of a dialing ratchet 261. As the sleeve SL rotates, it tensions a torsion spring S. Shift member 264 also defines the inject button B and when shift member 264 is moved from the dialing dose setting position shown in FIG. 77 to the injection dose delivery position shown in FIG. 78, it releases the torsion spring S. When released, the torsion spring S rotates output sleeve 266. An output ratchet member O on the output sleeve 266 then drives the ribbon assembly to extend the drive ribbon R, advance the piston and dispense medication. A threaded member IRD (insufficient remaining dosage) is disposed on a threaded section of the sleeve rotated by the dialing knob.

The embodiments depicted in FIGS. 55-78 do not experience a change in length when setting the dosage or when extending the drive ribbon with the limited exception that, when the inject button is disposed on one of the ends of the device and the button is depressed to actuate the injection procedure, the movement of the inject button alters the length an insignificant amount. In contrast, the devices depicted in FIGS. 79-96, and further described below, include plungers that are extended from the device and increase the length of the device when the dosage is being set and the subsequent manual depression of the plungers to return them to their original position provides the driving power to extend the drive ribbon, advance the piston within the medication container and dispense the medication.

Figure 83:
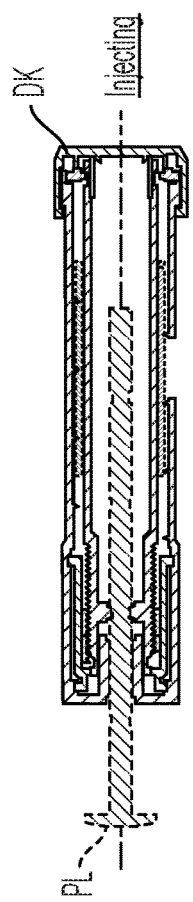
FIG. 83 is a schematic view of the drive member mechanism of the device of FIG. 79 in a dialing dose setting configuration.
Figure 84:
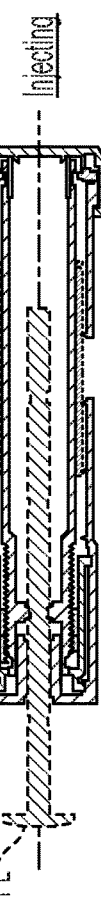
FIG. 84 is a schematic view of the drive member mechanism of the device of FIG. 79 in an injecting dose delivery configuration.
Figure 128:
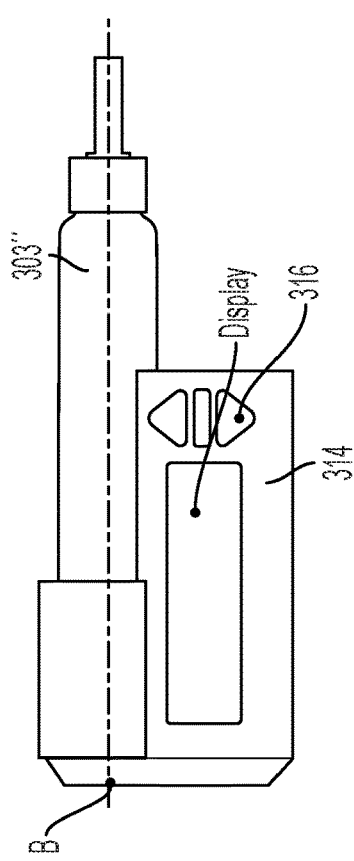
FIG. 128 is a side view of the device of FIG. 127.

The device 263 depicted in FIGS. 79-84 has dialing knob DK for setting the dosage. As the dialing knob DK is rotated, a dialing clicker in the form of a one-way ratchet mechanism 261 rotates the sleeve SL. As the sleeve SL is rotated, the plunger PL is extended out of the housing in the proximal direction due to the threaded engagement of the sleeve and plunger to place the device in the dialing dose setting configuration as shown in FIG. 83. When the plunger PL is manually depressed to force it back into the housing in the distal direction to place the device in the injecting dose delivery configuration shown in FIG. 84, the sleeve SL rotates in the opposite direction and causes output sleeve 268 to rotate along with it. The plunger PL does not rotate when being extended or depressed. To prevent the plunger PL from rotating, the stem of the plunger can have a non-circular cross section that passes through a corresponding opening in the housing. The output ratchet O on the output sleeve then transmits that rotational force to a drive member that rotates either the drive ribbon R or a thrust member to axially advance the piston and discharge medication.

The device 263' depicted in FIGS. 85-90 is generally similar to that depicted in FIGS. 79-84 but the dialing knob DK has been relocated to the proximal end of the housing. Each of these embodiments may also include a threaded member IRD (insufficient remaining dosage) that is disposed on the threaded section of the sleeve.

The device 263" depicted in FIGS. 91-96 has an extendable plunger wherein several components of the drive assembly centered on secondary axis 256 extend with the plunger when the dosage is being set and move with the plunger when it is being depressed. A dialing knob is used to set the dosage. When rotating the dialing knob DK, it rotates a dial sleeve 270 and plunger rod 274. Plunger rod 274 is threaded and engaged with a threaded opening 276 disposed on an internal portion of the housing. Rotation of plunger rod 274 relative to opening 276 causes the plunger rod 274 to be extended out of the housing in the proximal direction when setting the dosage, as shown in FIG. 95, while sleeve 270 is rotationally decoupled from plunger rod 274 but travels axially with dialing sleeve 278 and plunger rod 278. Depressing the inject button B rotationally engages plunger rod 274 with sleeve 270, which is rotationally engaged with output sleeve 272. As the dialing assembly is pressed distally back into the housing, it rotates causing output sleeve 272 to also rotate, as shown in FIG. 96. As output sleeve 272 rotates, the output ratchet O on output sleeve 272 rotates the output shaft. The output shaft, in turn, rotates a drive member or thrust member to extend the drive ribbon R, advance the piston and discharge medication.

Modular Architecture

The device 283 depicted in FIGS. 97-102 has a modular architecture with a detachable electronic module having an inject button that can be attached to a cartridge unit having a medication container, a drive ribbon and a drive assembly. The electronic module can be re-used multiple times with different cartridge units having the same basic structure. Such cartridge units may also be disposable units.

The device depicted in FIGS. 97-102 has a reusable electronic module 280 which can be detachably connected to a cartridge unit 282. Cartridge unit 282 includes a medication container 248 holding a medication and having a piston wherein advancement of the piston dispenses medication through an injection needle 252. A drive ribbon R is used to advance the piston and defines a primary drive axis 254. The illustrated cartridge unit 282 also includes a drive member mechanism centered on secondary axis 256. Illustrated cartridge unit 282 is a single use cartridge that is disposed of after depletion of the medication.

A dialing knob DK is used to set the dosage. Rotation of the dialing knob DK rotates the sleeve SL by means of a dialing ratchet 261. Rotation of the sleeve SL tensions the torsion spring S. Moving the inject button B from the position shown in FIG. 101 to that shown in FIG. 102 an arm 285 of the button B engages the sleeve SL and allows the sleeve SL to shift axially and thereby releases the torsion spring S. Injection cannot be initiated when display is removed. When released, the torsion spring S rotates output sleeve 284. Rotation of output sleeve 284 is communicated to the ribbon assembly and extends the drive ribbon R to thereby advance the piston and discharge medication. When the inject button B is in the position shown in FIG. 101, the sleeve SL is in an axial position that prevents the communication of torque from the torsion spring S to the output sleeve 284 and thereby prevents the torsion spring S from advancing the drive ribbon R. When the electronic module 280 is removed from the cartridge unit 282, the sleeve S remains in the position shown in FIG. 101 and, thus, the torsion spring S will not advance the drive ribbon R when the electronic module 280 is removed.

The embodiments of FIGS. 103-136 also have a modular architecture. The reusable module of these embodiments, however, includes a drive member mechanism centered on the secondary axis thereby allowing a greater percentage of the total assembly to be reused. The drive member mechanism is disposed within the housing and the device further includes a cartridge housing wherein the drive ribbon is disposed within the cartridge housing and the container is mounted on the cartridge housing with the cartridge housing being detachably securable to the housing.

In the embodiments depicted in FIGS. 103-108 and FIGS. 109-114, the devices have a drive member mechanism that includes a spring aligned with the secondary axis wherein setting a dose includes tensioning the spring and releasing the tension from the spring generates the force that is transferred to the drive ribbon to move the drive ribbon from the retracted configuration to the extended configuration.

More specifically, the device 293 depicted in FIGS. 103-108 includes cassette 286 having a cartridge housing 286A and a reusable module 288 having a main housing 288A. As can be seen in FIG. 103, the drive ribbon R is disposed within cartridge housing 286A and the cartridge 148 holding a medication is mounted on the cartridge housing 286A. As can also be seen in FIG. 103, the drive member mechanism 290 which drives the axial advancement of the drive ribbon R is disposed in main housing 288A and is centered on secondary axis 256.

The depicted device 293 includes a dialing knob DK that is used to set the dosage. Rotation of the dialing knob DK rotates the sleeve SL by means of the dialing ratchet 261. As the sleeve SL is rotated, the torsion spring S is tensioned. When the inject button B is depressed, the sleeve SL is shifted and the torsion spring S is released. When released, the torsion spring S rotates output member 292 that, in turn, rotates a drive member 294 engaged with the drive ribbon R to thereby extend the drive ribbon. Dial 297 is provided between the sleeve SL and spring S and is used with the interlock 295 for dose tracking.

The reusable module 288 includes an electronic module (not shown) coupled with the display. An interlock 295 provides an electrical signal which the electronic module uses to determine if the reusable module 288 is attached to the cassette 286. A sensor senses the rotational movement of the sleeve SL and provides the electronic module with data concerning the quantity of medication to be dispensed based upon the extent to which the sleeve has been rotated due to rotation of the dialing knob DK. The interlock may be configured to return device to zero when cassette is removed, by resetting the positon of the dial 297. The cassette 286 may include a RFID (radio frequency identification) chip to identify the contents of the medication container. Advantageously, the RFID chip is read/write whereby the electronic module on the reusable module 288 can record data related to the quantity of medication dispensed from the cassette 286 after each injection procedure whereby the module will be able to determine the remaining quantity of medication in the cassette. Alternatively, the cassette 286 may have a read only RFID tag with another form of digital memory to record such data. By recording data concerning the type and remaining amount of medication on the cassette, the cassette 286 can be removed from the reusable module 288 before it is completely depleted and then later re-attached with the electronic module being able to read the data concerning the identification of medication and remaining amount when the cassette is reattached. This will allow the electronic module to accurately track the amount of remaining medicine and generate an IRD (insufficient remaining dose) message even when a cassette has been detached when partially empty and then subsequently reattached.

The device 293" depicted in FIGS. 109-114 is similar to that shown in FIGS. 103-108 but has a different reusable module 298 wherein the dialing knob DK is located on the distal end instead of the proximal end of the reusable module 298. The dialing knob DK is used to set the dosage and rotation of the knob rotates the sleeve SL by means of a dialing ratchet 261. Rotation of the sleeve SL tensions a torsion spring S. Depression of the inject button B releases the spring S which then rotates output member 296. Rotation of output member 296 drives the extension of the drive ribbon R. Similar to module 288, module 298 includes an electronic module that is coupled with a display and which can communicate with the cassette to identify the contents of the cassette and remaining volume.

Instead of having a spring drive member mechanism, the reusable module may alternatively have an electric motor. For example, the embodiments depicted in FIGS. 115-120; FIGS. 121-126; and FIGS. 127-132 each have a drive member mechanism that includes an electric motor drivingly coupled with an element disposed along the secondary axis, the electric motor generating the force that is transferred to the drive ribbon to move the drive ribbon from the retracted configuration to the extended configuration. For example, the motor shaft may be the element disposed along and defining the secondary axis.

The device 303 depicted in FIGS. 115-120 includes a reusable module 300 having an electric motor M that can be coupled with a cassette 286. The motor M includes a motor shaft 304 that rotates a drive element 302 which, in turn, rotates drive member 294 of the cassette to extend the drive ribbon R. In the embodiment of FIGS. 115-120, the drive ribbon R extends axially without rotation. Cassette housing member 287 functions as the rotational restraint member and includes axially extending tabs (not shown here but described previously) to prevent rotation of the drive ribbon R. Drive member 294 functions as a thrust member and includes a helical thread that engages and axially drives the drive ribbon R. Drive member 294 is axially captured by housing member 287 within an annular groove that allows drive member 294 to rotate but prevents axial movement of drive member 294. The outer radial surface of drive member 294 projects outwardly from the cassette as can be seen in FIG. 119 and defines a geared surface. Drive element 302 defines a cooperating geared surface for engaging and rotatably driving the drive member 294.

An electronic module can be used to control the operation of the motor. A dialing knob DK can be used to generate signals to the electronic module to define the dosage and an inject button B communicates with the electronic module to initiate the operation of the motor. As can be seen in FIG. 116, the dialing knob DK is located on the distal end of module 300 while the inject button B is located on the side of the module 300 farthest from the cartridge 248 of cassette 286 and near the dialing knob DK. The electronic module may also communicate with the cassette 286 as described above to identify the contents of the cartridge 248 and determine the quantity of medication remaining in the cassette.

The device 303' depicted in FIGS. 121-126 has a reusable module 306 that can have a cassette 286 attached thereto. Module 306 has an electric motor M and the same general functionality of module 300. A motor shaft 308 extends from the motor M and a drive element 310 is mounted on shaft 308. Drive element 310 engages and rotates drive member 294 on the cassette 286 when the motor M is energized. Module 306 differs from module 300 in that it includes a proximal foot 312. Foot 312 is positioned adjacent the proximal end of cassette 286 and has an inject button B mounted thereon. Foot 312 helps to prevent accidental dislodgement of the cassette 286 and provides a more secure attachment for the cassette 286. It also allows the inject button B to be placed on the drive axis 254 defined by the drive ribbon. Some users may find this placement to be more intuitive and comfortable due to its similarity with a syringe having an inline manual plunger.

The device 303" depicted in FIGS. 127-132 has a reusable module 314 that is similar to module 306 with the only distinction being that module 314 uses input buttons 316 to set the dosage instead of a dialing knob. As shown, one of the input buttons 316 is for increasing the dosage and the other of the input buttons 316 is for reducing the dosage. The display may be used to indicate the change in dosage as a result the use of the input buttons.

In any of the reusable modules described herein having an electric motor M and/or electronic module, the reusable modules can include a single charge disposable battery or a rechargeable battery (shown in FIG. 127 as battery 313) for powering the electric motor and the electronic module and/or cassette 286'. Electronic modules described herein (shown representatively as electronic module 315 in FIG. 127) that is electrical communication with the module and the cassette is configured to control operation of the module and cassette and may include a processor or similar microcontroller and a transceiver or alternative communication hardware.

Figure 131:
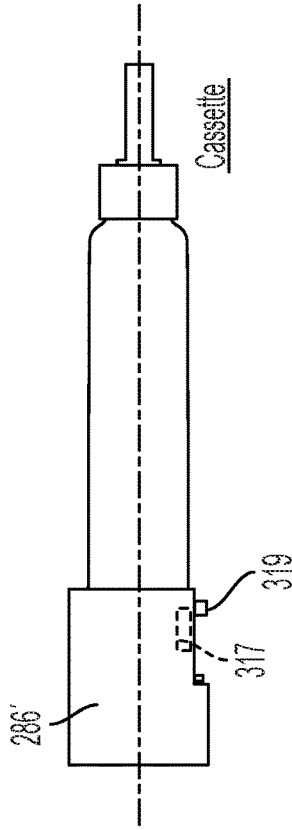
FIG. 131 is a side view of the cassette of FIG. 128.

Instead of a rechargeable battery, the reusable modules described herein may employ disposable batteries or, alternatively, a small disposable battery could be included in each cassette, rather than onboard on the module, which is sized to provide sufficient energy to the electric motor M to empty the contents of the cassette. In this regard, it is noted that FIG. 131 schematically depicts a cassette 286' having a battery 317 for powering the reusable module. When positioning a battery or other electrical power source in the cassette 286', electrical contacts 319 on the cassette and electrical contacts 321 on the module (FIG. 132) will engage when the cassette and module are connected to thereby transfer electrical power from the cassette to the module. Such cooperating electrical contacts on any of the cassettes and reusable modules described herein may also be used to provide communication or power conduit between electronic circuits on the cassette and reusable module.

As best understood with reference to FIGS. 133-136, for embodiments having a reusable module and a cassette with a cartridge housing, the device may further include a plurality of cartridges, each cartridge including a cartridge housing with a drive ribbon being disposed within the cartridge housing and a container being mounted on the cartridge housing, each of the cartridges being interchangeably and detachably securable to the housing of the reusable module.

Moreover, as discussed above with regard to a single cassette, in those embodiments having a plurality of cartridges, an electronic module may be disposed on the housing of the reusable module and each of the plurality of cartridges may further include a digital memory device such as a read/write RFID or other form of digital memory (e.g., internal flash memory or on-board EEPROM). The electronic module of the reusable module will establish communication with the digital memory device of the cartridge coupled with the housing and, after completing an injection procedure, the electronic module records data on the digital memory device related to the injection procedure. In such an embodiment, the data recorded on the digital memory device may include data related to the volume of medication remaining in the container. In such embodiments, the plurality of cartridges may all contain the same medication or they may contain a plurality of different medications.

Figure 133:
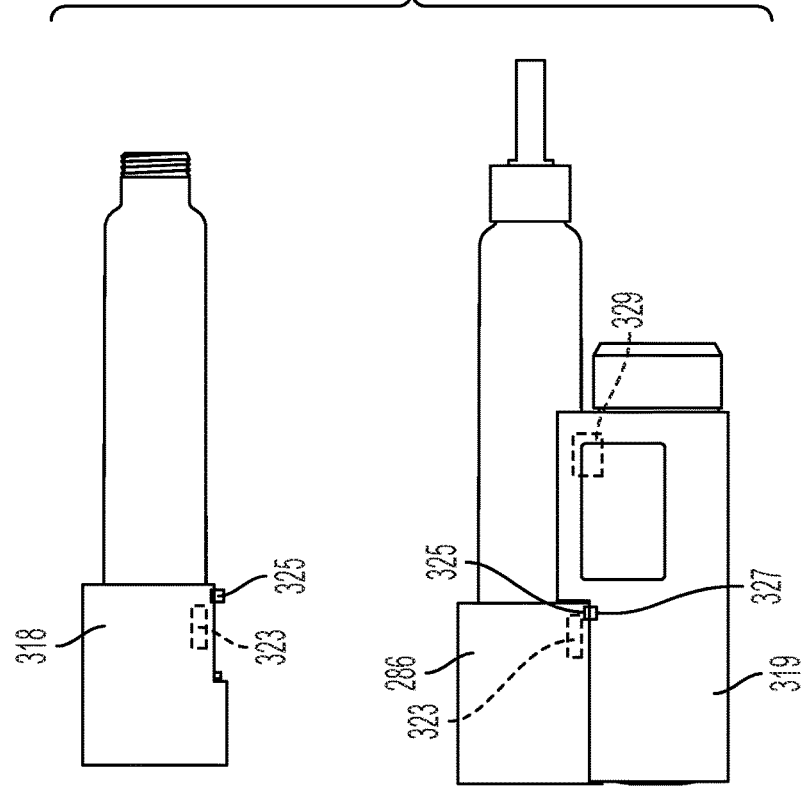
FIG. 133 is a schematic view of an exemplary drive member mechanism module with an attached cassette and an additional cassette.

FIG. 133 illustrates a medication delivery system 317 including the cassette 286, a second cassette 318, and the reusable module 319 which can be detachably secured to cassette 286 whereby the module 319 can drive the extension of the drive ribbon within cassette 286 to dispense a medication. Second cassette 318 may be identical to cassette 286 except that it does not yet have a needle assembly secured to the distal end of the medication container. The ability to interchange cassettes 286 and 318 with a single reusable module 316 has several advantages. For example, if a patient potentially needs to inject two different medicines over the course of the day, cassettes 286 and 318 can hold the two different medicines and the patient only needs to carry the single module 316 to use with the two different cassettes providing a compact system. Moreover, the cassettes 286 and 318 can be provided with read/write RFIDs or read only RFIDs and a digital memory whereby the patient can interchange the cassettes as needed and the module will still be able to identify the medicine contained in the cassette which is attached and the amount remaining in the cassette as discussed above. Alternatively, if the patient only requires a single medication, they may still find it convenient to carry the module 316 and two cassettes 286 and 318 which hold the same medication with the second cassette functioning as a back-up supply in case the first cassette is depleted or needs to be replaced for some other reason.

Figure 134:
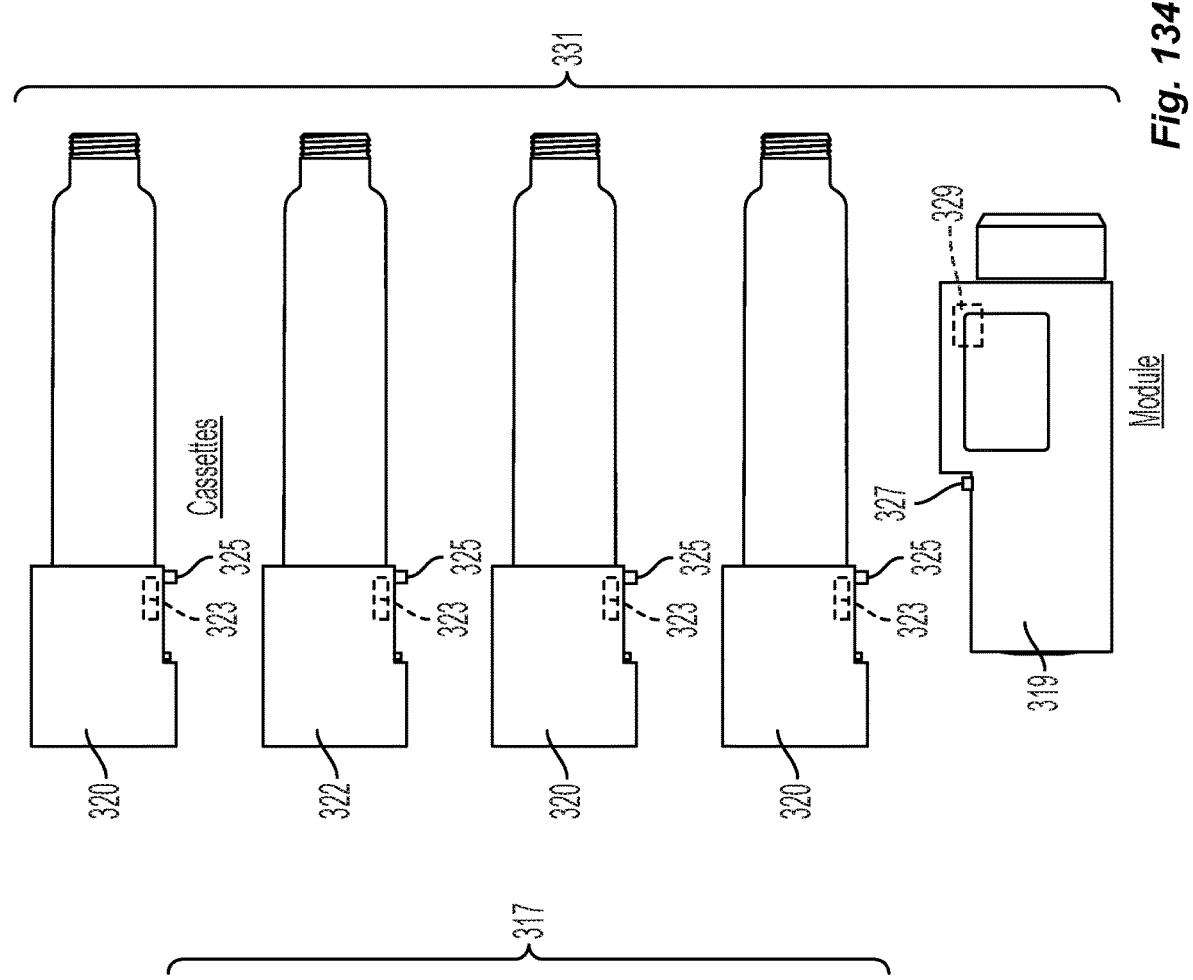
FIG. 134 is a schematic view of the drive member mechanism module of FIG. 133 and a plurality of cassettes.

FIG. 134 also illustrates how module 316 can be used with multiple cassettes of different medications in a medication delivery system 331. In the embodiment of FIG. 134, cassettes 320 and 322 all have the same structure as cassette 318. The only difference between cassettes 320 and 322 is that cassette 322 contains a different medication than cassettes 320. While the RFID of the cassettes will identify the medication contained within the cassette and such information can be displayed for the user to see it on the display of the reusable module 319, the cassettes holding different medicines are also advantageously identifiable by visual inspection. For example, cassettes 320 which all hold the same type of medication may advantageously have the same color cartridge housing while cassette 322, which holds a different medicine, has a cartridge housing of a different color. Printed labels identifying the contents of the cassettes may also be adhered to the cassettes.

In the embodiments of FIGS. 133-134, cassettes 286, 318, 320, 322 each may have a digital memory device 323 which includes data on the type of medication contained within the cartridge and remaining volume of the medication. Still other data, such as date of manufacture, serial numbers may also be recorded on digital memory device 323. Module 319 includes an electronic module 329 utilizing a controller which controls operation of the module and cassette. Electronic module 329 also communicates with the digital memory device 323 of the cassette engaged with the module 316 to acquire information about the type of medication and remaining amount of the medication in the cassette.

Also shown in FIGS. 133-134 are electrical contacts 325 on cassettes 286, 318, 320, 322 and cooperating electrical contacts 327 on module 316. When a cassette is mounted on module 316, the cooperating contacts 325, 327 are engaged to provide electrical communication therebetween for data signal transmission and/or power. The use of contacts 325, 327 allows the electronic module 329 of module 316 to communicate in a hard-wired manner with digital memory device 323. Alternatively, electronic module 329 can communicate wirelessly with digital memory device 323 and contacts 325, 327 can be used to confirm that a cassette has been successfully docked on module 316. For example, when contacts 325, 327 are not engaged, the circuit on module 316 with contacts 325 may be open. Then, when a cassette is mounted on module 316, contacts 327 will engage with contacts 325 and close the circuit in which contacts 325 are located. Electronic module 329 can monitor whether or not the circuit having contacts 325 is open or closed to thereby determine whether or not a cassette has been mounted to module 316.

Figure 136:
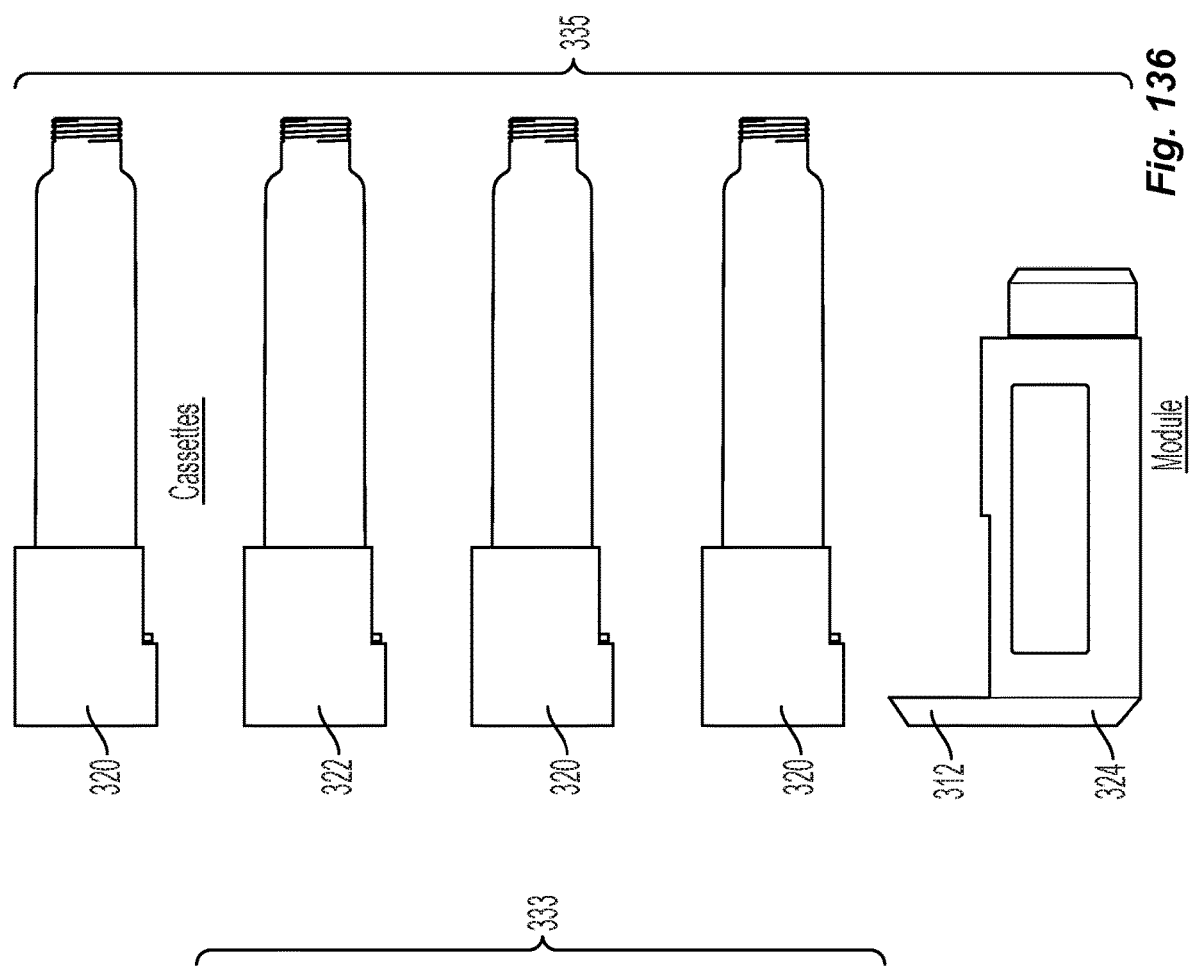
FIG. 136 is a schematic view of the drive member mechanism module of FIG. 135 and a plurality of cassettes.
Figure 135:
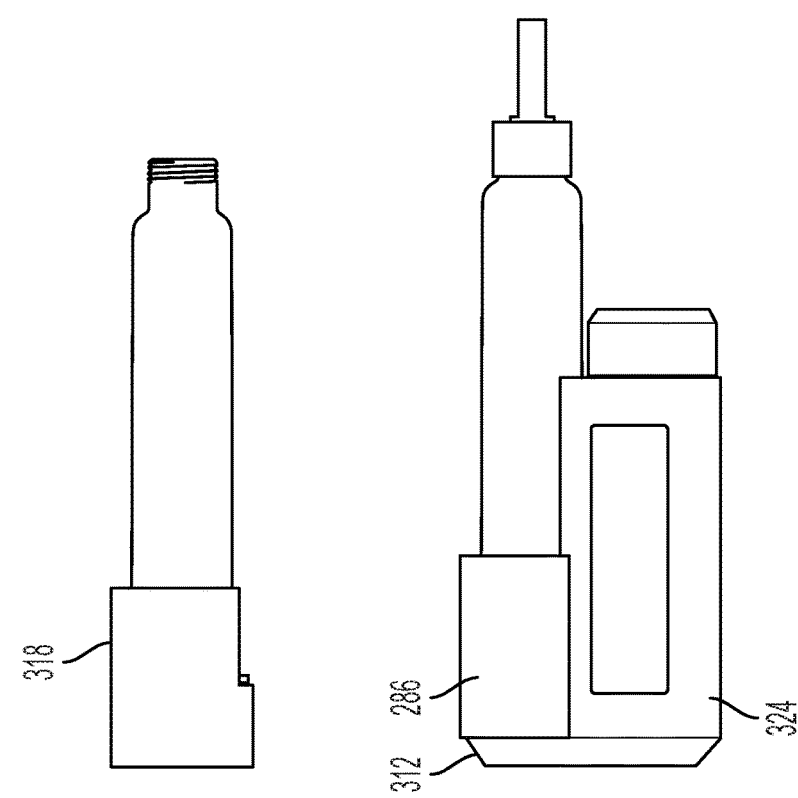
FIG. 135 is a schematic view of an exemplary drive member mechanism module with an attached cassette and an additional cassette.
Figure 155:
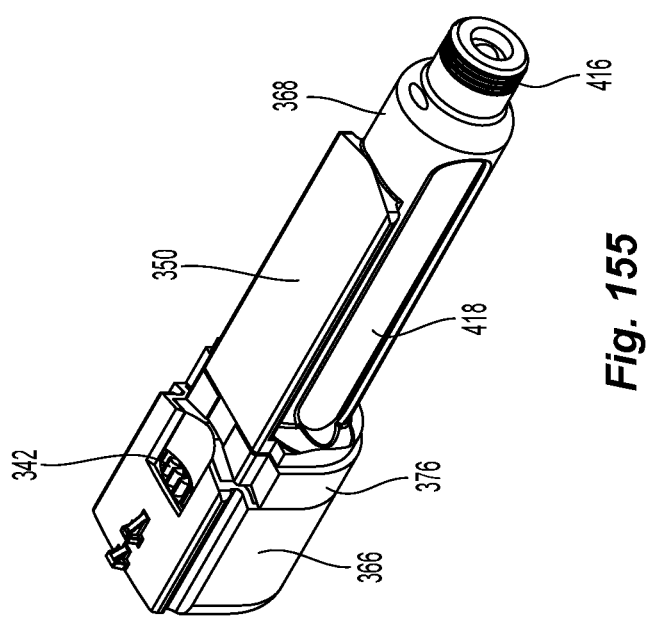
FIG. 155 is a perspective view of a cassette.

FIGS. 135 and 136 depict systems 333, 335, respectively, similar to systems 317, 331 in FIGS. 133 and 134 but have a reusable module 324 that differs from module 316 in that module 324 includes a foot 312 similar module 306. Otherwise, reusable module 324 functions the same as module 316 and can be used with cassettes 286, 318 and 320 and 322 in the same manner discussed above with regard to module 316.

It is noted that the reusable modules and cassettes may track the remaining quantity of medication in the cassette in various manners. As mentioned, above, the remaining quantity can be tracked by having the reusable module monitor the set dosages and/or the mechanical output delivered to the cassette to determine the amount of medication dispensed during each injection procedure. The original quantity of medication held in the medication container is known and, thus, by subtracting the dispensed amount, the remaining quantity can be tracked and monitored.

Alternatively, the extent to which the drive ribbon has been axially extended can be monitored to determine the remaining quantity. For example, the drive ribbon may be provided with markings that can be read by an optical sensor. The optical sensor is positioned to sense the markings on the extended portion of the drive ribbon and, for devices having a modular architecture, may be positioned on the cassette or on the reusable module with a window in the housings allowing the optical sensor to view the extended portion of the drive ribbon. The sensor could count the passage of identical markings or be able to recognize distinct markings to determine the extent to which the drive ribbon has been axially extended. By tracking the length to which the drive ribbon has been axially extended and knowing the dimensions of the medication container, the quantity of remaining medication can be determined. In this regard, it may be necessary to initially determine the length to which the drive ribbon is extended to initially engage the piston without dispensing medication. The extension of the drive ribbon after reaching its initial point of contact can be readily converted to an amount of medication dispensed for a conventional medication container having known dimensions.

FIGS. 137-145 illustrate an example of a reusable drive member mechanism module and a cassette having a cartridge housing and a drive ribbon disposed therein. FIGS. 146-211 also illustrate an example of a reusable drive member mechanism module and a cassette. One difference between the embodiment of FIGS. 137-145 and the embodiment of FIGS. 146-211 is that the size of the electric motor in the embodiment of FIGS. 137-145 and of the gear attached to the motor shaft are larger than those of the embodiment of FIGS. 137-145. Where the parts of the two embodiments are the same and function in the same manner, the same reference number will be used in each embodiment.

Device 326, which is shown in FIGS. 137-145, includes a reusable module 328 and a cassette 330. A needle assembly 332 is securable to the threaded distal end of a holding member for medication container 334. Module 328 includes a housing 336 within which an electric motor 338 is mounted. Gear 340 is coupled to and driven by the output shaft of motor 338. A portion of gear 340 projects outwardly from housing 336 whereby it can engage a gear member 342 within cassette 330 when cassette 330 is attached to module 328.

Cassette 330 includes a housing 344 that defines a projection 346 having a T-shaped cross section. Module housing 336 defines a corresponding T-shaped slot 348 which receives projection 346. Cassette 330 also defines a second T-shaped projection 350 which is received by a second T-shaped slot 352 on housing 336. When the T-shaped projections are slid into the T-shaped slots, a spring biased, pivoting latch member 354 on module 328 engages a projecting lip on the cassette to prevent the cassette from sliding out of engagement. Button 356 is depressed to disengage latch member 354.

Device 360 is shown in FIGS. 146-211 and includes a reusable module 362 and a cassette 330. Cassette 330 is detachably secured to module 362 in the same way that it is secured to module 328. Module 362 has a slimmer electric motor 364 and a smaller output gear 367 coupled to the motor shaft than module 328 but otherwise has the same construction.

Figure 164:
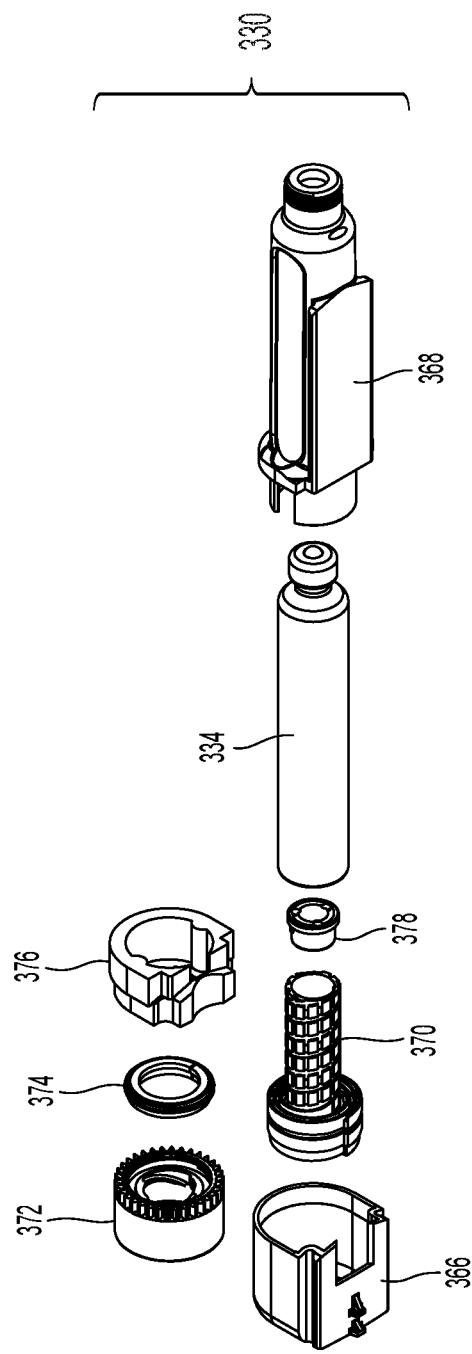
FIG. 164 is an exploded perspective view of a cassette.
Figure 165:
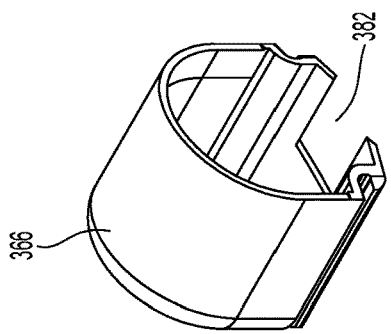
FIG. 165 is a perspective view of the cassette base of FIG. 164.
Figure 166:
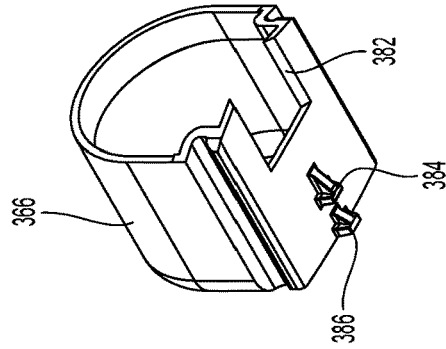
FIG. 166 is a perspective view of the cassette base of FIG. 164.
Figure 169:
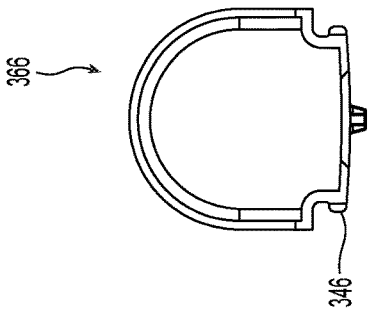
FIG. 169 is an end view of the cassette base of FIG. 164.
Figure 168:
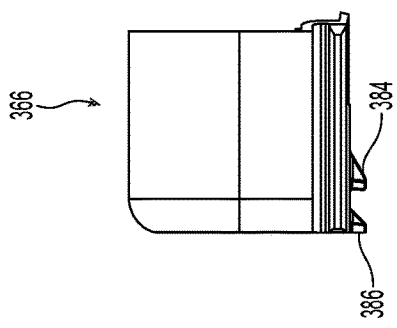
FIG. 168 is a side view of the cassette base of FIG. 164.
Figure 167:
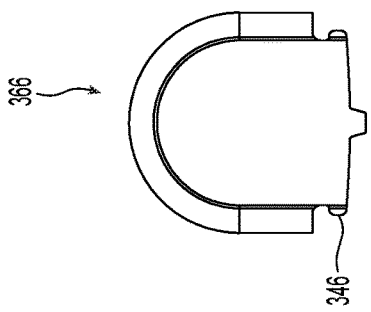
FIG. 167 is an end view of the cassette base of FIG. 164.
Figure 170:
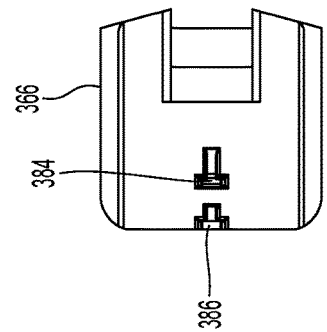
FIG. 170 is a side view of the cassette base of FIG. 164.
Figure 188:
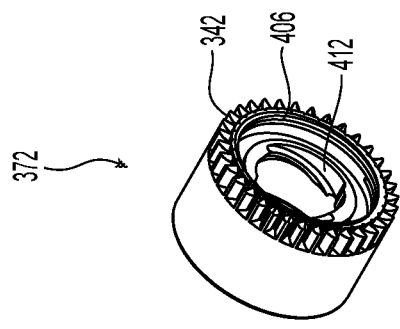
FIG. 188 is a perspective view of the cassette nut of FIG. 164.
Figure 192:
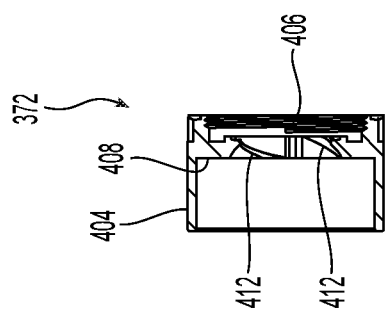
FIG. 192 is a cross section taken along line J-J of FIG. 190.
Figure 187:
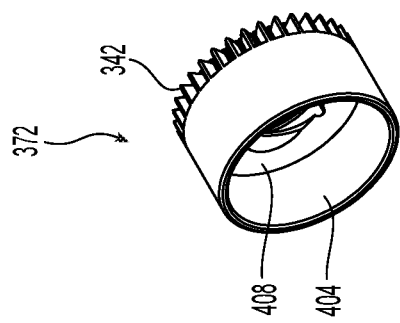
FIG. 187 is a perspective view of the cassette nut of FIG. 164.
Figure 191:
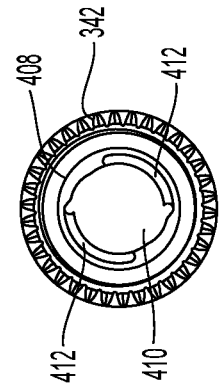
FIG. 191 is an end view of the cassette nut of FIG. 164.
Figure 190:
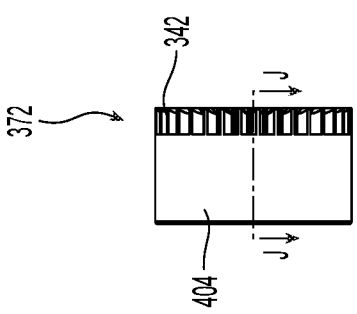
FIG. 190 is a side view of the cassette nut of FIG. 164.
Figure 189:
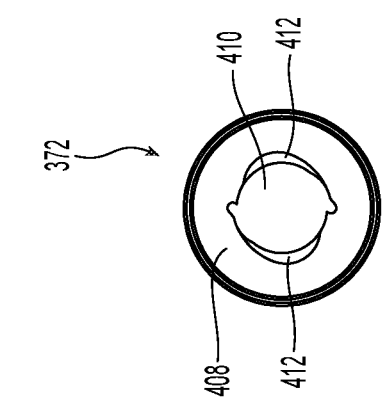
FIG. 189 is an end view of the cassette nut of FIG. 164.
Figure 200:
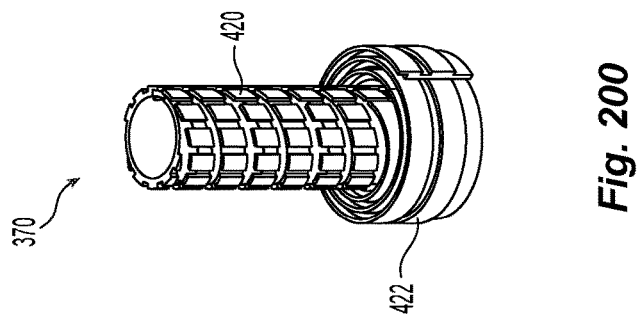
Figure 202:
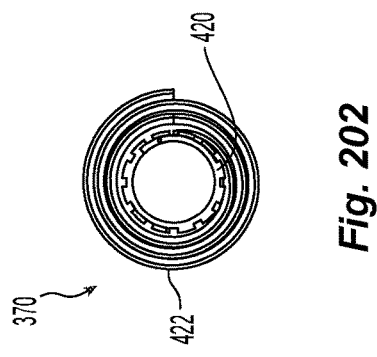

FIG. 164 provides an exploded view of cassette 330. Cassette 330 includes a base member 366 and a holding member 368 which together define the cartridge housing. A drive ribbon 370 is disposed within the cartridge housing and a thrust member 372, ring 374 and collar 376 control the axial extension of drive ribbon 370. A bearing member 378 is secured to the distal end of drive ribbon 370 and engages piston 380 within medication container 334. Ribbon 370 extends without rotation and bearing member 378 is fixed directly to ribbon 370. A conventional 3 ml medication container 334 is held within holding member 368. Holding member 368 has a bayonet type engagement for attaching member 368 to the cassette although other suitable means such as permanent adhesive may alternatively be used.

Cassette base 366 is shown in FIGS. 165-170. Base 366 houses the proximal components of the cassette and includes a window 382 that allows gear member 367 to mesh with gear 342 which is formed on thrust member 372. Base 366 also defines T-shaped projection 346 and a pair of smaller projections 384, 386. Projection 384 is engaged by latch 354 when cassette 330 is engaged with a reusable module and projection 386 prevents the inadvertent external disengagement of latch 354.

Cassette collar 376 is shown in FIGS. 171-176. Collar 376 defines a central cylindrical opening 388. Disposed within the central opening 388 are a plurality of axially extending ribs 390. As further discussed below, ribs 390 engage axially extending grooves 371 in drive ribbon 370 to prevent the rotation of the extended portion of drive ribbon 370. Collar 376 has a first section 392 with a non-circular cross section that fits within base member 366 and thereby prevents collar 376 from rotating relative to base 366. Ribs 390 thereby prevent the extended portion of drive ribbon 370 from rotating relative to base 366. A second section 394 is disposed distally of the end of base 366 and receives the bayonet projections of holder 368 to thereby attach holder 368 to cassette 330. Section 394 has a central opening which is cylindrical in shape with two projections 395 that fit between the bayonet fittings of holder 368. Collar 376 also includes a cylindrical projection 396 that extends proximally and defines a portion of the central bore 388. Cylindrical section 396 also defines an annular recess 397 on its outer surface.

Cassette ring 374 is shown in FIGS. 177-181. Ring 374 encircles cylindrical section 396 and properly positions collar 376 relative to thrust member 372. Ring 374 also functions as a bearing between the rotatable thrust member 372 and the rotationally fixed collar 376. An annular projection 373 on ring 374 fits within on annular recess 397 on projection 396 and a threaded section 375 on ring 374 secures ring 374 to thrust member 372. Ring 374 thereby prevents the axial separation of collar 376 from thrust member 372 while still permitting the rotation of thrust member 372 and attached ring 374 relative to collar 376.

Distal bearing member 378 is shown in FIGS. 182-186. Member 378 includes a distal bearing flange 398 that engages piston 380 and a mounting stem 400 that is disposed radially inwardly of the most distal portion of drive ribbon 370. Mounting posts 402 on stem 400 are engaged with holes on drive ribbon 370 to mount bearing member 378 to drive ribbon 370.

Thrust member 372 is shown in FIGS. 187-192. Thrust member 372 has gear 342 formed on its outer perimeter. In another embodiment, a gear component may be fixedly coupled to the thrust member. Gear 342 engages gear 367 and thrust member 372 is rotated when motor 364 is energized and rotating gear 367. Thrust member 372 has a generally cylindrical shape and rotates within and relative to base 366. The proximal end of thrust member 372 forms a cylindrical skirt 404 that functions as a storage bobbin for the retracted portion of drive ribbon 370. Threads 406 at the distal end of thrust member 372 engage threads 375 on ring 374 to secure ring 374 to thrust member 372. As discussed above, this also axially secures collar 376 to thrust member 372 while still permitting the rotation of thrust member 372 and ring 374 relative to collar 376.

An inner partition 408 extends inwardly and defines a central opening 410 within thrust member 372. Partition 408 also defines a pair of generally helical threads 412 that act as camming ramps. Threads 412 engage grooves 369 in drive ribbon 370 that extend helically on the extended portion of drive ribbon 370. When initially assembling cassette 330, a portion of the drive ribbon 370 is placed in the extended configuration and threads 412 are engaged with grooves 369. When thrust member 372 is subsequently rotated, threads 412 will force ribbon 470 from the retracted configuration to the extended configuration thereby extending the axial length of the extended configuration, or, depending on the direction of rotation, force ribbon from the extended configuration to the retracted configuration thereby reducing the axial length of the extended portion of the drive ribbon. If module 328 is designed to work with only disposable cassettes 330, it will not be necessary to retract drive ribbon 370 after emptying the contents of container 334 and module 328 may be configured such that motor 364 will rotate in only one direction when energized with that direction corresponding to the axial extension of drive ribbon 370. It is noted that as threads 412 engage helical grooves 369 and move drive ribbon 370 axially, ribs 390 located on collar 376 will engage the axially extending grooves 371 on drive ribbon 370 and prevent rotation of ribbon 370. The adjacent edges of ribbon 370 will also become engaged with each other as the ribbon moves into collar 372.

Holding member 368 is shown in FIGS. 193-198. Holding member 368 defines T-shaped projection 350 for engaging the reusable module. Holding member 368 also includes a pair of bayonet fittings 414 that are inserted into the bore defined by section 394 of collar 376 and tightly fit between projections 395 to thereby mount holding member 368 to cassette 330. Alternative attachment means such as permanent adhesive may be used to attach holding member 368 to cassette 330. A medication container 334 is placed within holder 368 before mounting the holding member 368 to cassette 330. A threaded distal end 416 on holding member 368 is used to attach needle assembly 332. When attaching needle assembly 332 to threaded distal end 416, the needle of assembly 332 will pierce a septum on medication container 334 whereby it will be possible to dispense medication through the needle. Cut outs in member 368 form windows 418 that allow a user to view medication container 334 whereby the quantity of medication remaining in the container can be determined by a visual inspection.

Figure 201:
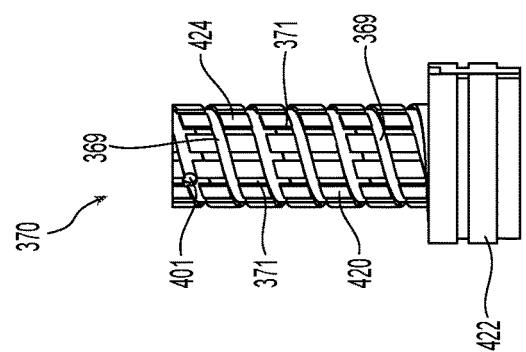
Figure 199:
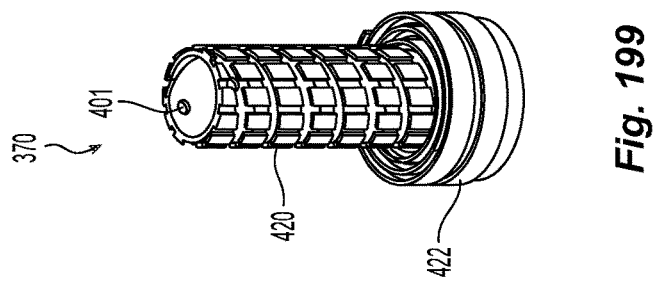

Drive ribbon 370 is shown in FIGS. 199-211. In FIGS. 199-202, drive ribbon 370 is shown in a configuration that it will take within cassette 330. In this arrangement, an extended portion 420 of ribbon 370 defines a helix while a retracted portion 422 of ribbon 370 defines a spiral. As can be seen in FIGS. 199 and 201, the distal section of ribbon 370 defines a pair of holes 401 that receive posts 402 to thereby mount bearing member 378 to ribbon 370. The outer surface of ribbon 370 includes a plurality of regularly spaced projections 424 that define grooves 369, 371 therebetween. It is noted projections 424 and grooves 369, 371 will face outwardly on the retracted portion 422 of ribbon 370 just like they do on the extended portion 420, however, FIGS. 199-201 do not show projections 424 or grooves 369, 371 for reasons of graphical simplification and clarity.

The individual features of drive ribbon 370 are best seen in FIGS. 203-207 which show a drive ribbon 370 unrolled and laying on a flat surface. FIG. 203 and detail view FIG. 206 show the outward facing surface of drive ribbon 370 while FIG. 205 and detail view FIG. 207 show the inward facing surface of drive ribbon 370. FIG. 204 shows an edge of ribbon 370.

As best seen in FIG. 206, projections 424 on the radially outward facing surface of ribbon 370 define two sets of parallel grooves, 369, 371 between the projections 424. Grooves 369 extend in a helical shape on the extended portion 420 of ribbon 370. Grooves 369 are engaged by threads 412 on thrust member 372 to form drive ribbon 370 into helical shape. The engagement of threads 412 with grooves 369 also allows axially directed forces to be transferred between ribbon 370 and thrust member 372. Grooves 371 extend in an axial direction on the extended portion 420 of ribbon 370 and, as explained above, engage ribs 390 on collar 376 to prevent rotation of extended portion 420.

As best seen in FIG. 207, one of the edges (shown as the distal edge 426) of ribbon 370 defines a plurality of projections 432 while the other edge (shown as the proximal edge 428) defines a corresponding plurality of openings 430. As can be seen in FIG. 207, projections 432 and projections 424 overlap along the distal edge 426. When the distal 426 and proximal 428 edges of ribbon 370 are being engaged, the proximal edge 428 will be positioned radially inward of the distal edge 426. As the distal edge 426 moves radially inward to engage the proximal edge 428, openings 430 and projections 432 will mesh to interlock the two edges and the overlapping projections 424 will prevent the projections 432 from being pushed completely through openings 430. The engagement of projections 432 and openings 430 provides shear resistance along the edges and the shape of projections 432 with openings 430 with projections 432 having an enlarged head on a narrower neck also resist axial separation of the two interlocked edges.

When using a drive ribbon 370, only a single ribbon 370 will be employed with each cassette 330 and the distal and proximal edges of the individual ribbon will be interlocked together in the extended portion of the ribbon. In FIGS. 208-211, two ribbons 370 are shown laying flat with their distal and proximal edges interlocked to provide a better understanding of the interlocking of the two edges and graphical clarity. In use, two separate drive ribbons 370 would not joined together as shown in FIGS. 208-211 (with the possible exception of doing so to create a single larger ribbon).

FIGS. 212-216 illustrate several additional embodiments which use various types of control to enhance the control and precision of the individual doses delivered by the device.

FIG. 212 schematically illustrates an embodiment which uses an encoder to enhance control and precision of the dosage amount delivered by the device, such as, for example, the device in FIG. 42. In the illustrated embodiment, a rotating drive ribbon 440 includes a set of gear teeth 442 along its proximal edge. An electric motor 444 drives a gear 446 that, in turn, engages gear teeth 442 and thereby drives rotation of drive ribbon 440. Drive ribbon 440 also includes a series of encoder targets 452 such as dark rectangles that are distinguishable from the drive ribbon 440 by optical sensor 450. Optical sensor 450 generates signals that are received by processor 448. By counting the number of encoder targets that pass by sensor 450, processor 448 can determine drive ribbon parameters (for example, angular position, length or extension position, speed of extension and/or retraction, stoppage) such as the length by which drive ribbon 440 has been axially extended. Processor 448 uses this information to control the operation of motor 444 and thereby also control the dosage amount delivered by the device.

FIGS. 213 and 214 schematically illustrate a device that uses a mechanical control to enhance the control and precision of the dosage amount. The embodiment of FIGS. 213-214 includes a rotating drive ribbon 454 which is driven by a pretensioned spring 458. Spring 458 is provided with sufficient pretensioning during manufacture to rotate drive ribbon 454 through its full extension. Drive ribbon 454 also includes a series of projections 456 that project radially outwardly from ribbon 454. The distance between each of the projections 456 corresponds to a predefined dosage of medication such as the amount of an individual dosage or a whole fraction thereof.

An actuator 460 is mounted on housing 462 and includes a camming surface 464. When actuator 460 is depressed radially inwardly, camming surface 464 interacts with control member 466. Control member 466 is disposed adjacent the extended portion of drive ribbon 454 and is biased by a spring (not shown) or other biasing member into the position shown in FIGS. 213 and 214. In this position, it blocks the passage of projections 456. Control member 466 also includes teeth that define camming surfaces 468 that are engageable with camming surface 464 on actuator 460.

When actuator 460 is depressed, camming surfaces 464 and 468 interact to bias control member 466 upwards whereby opening 470 is aligned with a projection 456 engaged with the side of control member 466. This allows projection 456 to pass through opening 470 and drive ribbon 454 to be extended under the influence of pretensioned spring 458. Actuator 460 also includes a spring (not shown) that biases it out of engagement with control member 466. Thus, when actuator 460 is depressed and then released, it will move control member 466 into a position where a projection 456 can pass through opening 470 and then return control member 466 to a position where it blocks the passage of a projection 456. This allows a user to easily dispense a predefined dosage amount simply by depressing and releasing actuator 460.

FIG. 215 illustrates a device that utilizes an image sensor 476 to read codes 474 on rotating drive ribbon 472. Codes 474 are located at predefined intervals on drive ribbon 472 and read by image sensor 476 to facilitate control of individual dosage deliveries. Signals generated by image sensor 476 are communicated to processer 478 and may be stored in a digital memory. Processor 478, in turn, controls an electric motor or other suitable mechanism for rotating drive ribbon 472 based upon the signals generated by image sensor 476. Codes 474 may take various forms, for example, they may be QR codes, bar codes, encoder strip codes. Codes 474 may also take the form of different colors whereby a particular color change corresponds to a predefined distance along ribbon 472. Codes 474 may formed by screen printing graphics on the drive ribbon and may also include other information readable by image sensor 476 such as the type of drug, original quantity of the drug, and other forms of information.

For the embodiments of FIGS. 212 and 215, the sensor may be a part of the cassette. Alternatively, it could be a part of the reusable module with cooperating windows on the cassette and reusable module allowing the sensor to view the drive ribbon. FIG. 216 illustrates a device having an alternative configuration that facilitates the use of a sensor on the reusable module and may otherwise use a control system similar to that of the embodiments of FIGS. 212 and 215.

In the embodiment of FIG. 216, cassette 480 holds a rotatable drive ribbon 482 having codes 484 located on the inward facing surface of drive ribbon 482. Reusable module 486 includes a proximal foot 492 similar to the embodiments of FIGS. 121-126, 127-132, 135 and 136. Extending from proximal foot 492 is a stem 490 having a sensor 488 mounted on its free end to read the codes 484 on the inward facing surface of drive ribbon 482.

Any of the devices described herein may includes a controller (also referred to herein as an electronic module) and/or an electronic display. The display may include any one of or any combination of two or more light emitting diodes, e-ink technology, or liquid crystal technology. The display is circuited to and controlled by the electronic controller or computing assembly mounted within the housing. The controller includes conventional components such as, for example, a processor, power supply, memory, etc. The controller is programmed to achieve the electronic features of any one of the devices described herein, including causing the display of set doses. The set dose displayed in the display may be determined by the interaction of the dose setting and/or dose delivery drive mechanism and any one or more of the sensing systems electrically circuited or wirelessly communicated with the controller. The controller includes control logic operative to perform the operations described herein, including detecting a dose delivered by the medication delivery device based on a detected rotation or linear extension of the drive ribbon member relative to the actuator. The controller is operable to determine the dose setting by the drive ribbon parameter(s), such as, position based on rotational and/or linear position of respective components, which is determined by associating the electrical characteristic (such as voltage or resistance) from the respective sensors and the number of rotations to an exact and/or absolute position from a database, look up table, or other data stored in memory. The controller is operable to determine the dose delivery by determining the drive ribbon position based on rotational and/or linear position of respective components, which is determined by associating the electrical characteristic (such as voltage or resistance) from the respective sensor bands and the number of rotations to an exact and/or absolute position from a database, look up table, or other data stored in memory. The controller is operative to store the detected dose in local memory (e.g., internal flash memory or on-board EEPROM). The controller is further operative to wirelessly transmit a signal representative of the detected dose to a paired remote electronic device, such as a user's smartphone, over a Bluetooth low energy (BLE) or other suitable short or long-range wireless communication protocol. Illustratively, the BLE control logic and controller are integrated on a same circuit.

While this invention has been described as having an exemplary design, the present disclosure may be further modified within the spirit and scope of this disclosure. This application is therefore intended to cover any variations, uses, or adaptations of the invention using its general principles.

Various aspects are described in this disclosure, which include, but are not limited to, the following aspects:

1. A medication delivery device for use with a container having a container body holding a medication and defining an outlet, the container includes a piston disposed within the container body wherein advancement of the piston within the container body expels medication through the outlet, the delivery device comprising: a housing adapted to couple with the container; and a drive assembly coupled with the housing and adapted to advance the piston within the container, wherein the drive assembly comprises: a drive ribbon having a distal edge section and a proximal edge section, the drive ribbon being incrementally movable between a retracted configuration and an extended configuration about a drive axis, wherein a retracted portion of the drive ribbon in the retracted configuration defines a spiral and an extended portion of the drive ribbon in the extended configuration defines a helix; and a thrust member engaged with the drive ribbon and rotatably relative to the drive ribbon and the housing, wherein, in response to a rotation of the thrust member, the drive ribbon is movable between the retracted configuration and the extended configuration without any rotation relative to the housing or the container.

2. The device of aspect 1 wherein the thrust member is axially stationary.

3. The device of any one of aspects 1-2 wherein the thrust member includes a helical thread engageable with the drive ribbon, the device further comprising a rotational restraint member rotationally fixed relative to the housing and engaged with the drive ribbon to prevent relative rotation between the extended portion of the drive ribbon and the rotational restraint member.

4. The device of aspect 3 wherein one of the rotational restraint member and extended portion of the drive ribbon defines an axially extending key and the other one of the rotational restraint member and extended portion of the drive ribbon defines an axially extending keyway to accommodate said key.

5. The device of any one of aspects 3-4 wherein the rotational restraint member is disposed radially outside of the drive ribbon at an engagement location where the rotational restraint member is engaged with the drive ribbon to prevent rotation.

6. The device of any one of aspects 3-4 wherein the rotational restraint member is disposed radially inside of the drive ribbon at an engagement location where the rotational restraint member is engaged with the drive ribbon to prevent rotation.

7. The device of any one of aspects 3-6 wherein the helical thread is disposed radially outside of the drive ribbon at an engagement location where the helical thread is engaged with the drive ribbon.

8. The device of any one of aspects 3-7 wherein the thrust member is axially captured by the rotational restraint member.

9. The device of any one of aspects 3-8 wherein the helical thread is disposed radially inside of the drive ribbon at an engagement location where the helical thread is engaged with the drive ribbon.

10. The device of any one of aspects 1-9 wherein, in response to a rotation of the thrust member, the thrust member is movable axially in a proximal direction and a distal end of the drive ribbon remains axially stationary, and wherein, to advance the piston within the container body, the thrust member and an extended portion of the drive ribbon are axially moved in a distal direction.

11. The device of aspect 10 wherein the thrust member includes a helical thread engageable with the drive ribbon, the helical thread disposed radially outside of the drive ribbon at an engagement location where the helical thread is engaged with the drive ribbon, the device further comprising a rotational restraint member rotationally fixed relative to the housing and engaged with the drive ribbon to prevent relative rotation between the extended portion of the drive ribbon and the rotational restraint member.

12. The device of aspect 10 wherein the thrust member includes a helical thread engageable with the drive ribbon, the helical thread disposed radially inside of the drive ribbon at an engagement location where the helical thread is engaged with the drive ribbon, the device further comprising a rotational restraint member rotationally fixed relative to the housing and engaged with the drive ribbon to prevent relative rotation between the extended portion of the drive ribbon and the rotational restraint member.

13. The device of any one of aspects 10-12 further comprising a drive spring, the drive spring being tensioned as the thrust member is rotated to extend the drive ribbon, wherein, in response to release of a tension of the drive spring, the drive spring is configured to axially advance the thrust member and extended portion of the drive ribbon.

14. A medication delivery device for use with a container having a container body holding a medication and defining an outlet, the container includes a piston disposed within the container body wherein advancement of the piston within the container body expels medication through the outlet, the delivery device comprising: a housing adapted to couple with the container; and a drive assembly coupled with the housing and adapted to advance the piston within the container, wherein the drive assembly comprises: a drive ribbon having a distal edge section and a proximal edge section, the drive ribbon having a retracted configuration and an extended configuration, wherein a retracted portion of the drive ribbon in the retracted configuration defines a spiral and an extended portion of the drive ribbon in the extended configuration defines a helix, the drive ribbon being incrementally movable from the retracted configuration to the extended configuration about a drive axis, wherein the drive ribbon is rotated during a movement from the retracted configuration to the extended configuration, wherein the drive assembly and the drive ribbon are in a coaxial relationship.

15. The device of aspect 14 further comprising a drive member disposed radially inside of the drive ribbon, the drive member configured to drivingly rotate the drive ribbon, and a collar including a helical thread engaged radially outside the drive ribbon to control a movement of the drive ribbon between the retracted configuration and the extended configuration.

16. The device of aspect 14 further comprising a drive member disposed radially inside of the drive ribbon, the drive member configured to drivingly rotate the drive member, and a helical thread engaged with the drive ribbon to control a movement of the drive ribbon between the retracted configuration and the extended configuration.

17. The device of aspect 14 further comprising a drive member disposed radially outside of the drive ribbon, the drive member configured to drivingly rotate the drive ribbon.

18. The device of aspect 17 wherein the drive member is a ring gear, a plurality of ring gears, a belt, a plurality of planet gears, a worm gear, or a key drive.

19. The device of aspect 18 wherein the drive ribbon defines a plurality of slots engageable by the drive member.

20. The device of aspect 18 wherein the drive ribbon defines a plurality of ribs engageable by the drive member.

21. A medication delivery device for use with a container having a container body holding a medication and defining an outlet, the container includes a piston disposed within the container body wherein advancement of the piston within the container body expels medication through the outlet, the delivery device comprising: a housing adapted to couple with the container; and a drive assembly coupled with the housing and adapted to advance the piston within the container, wherein the drive assembly comprises: a drive ribbon having a distal edge section and a proximal edge section, the drive ribbon having a retracted configuration and an extended configuration, wherein a retracted portion of the drive ribbon in the retracted configuration defines a spiral and an extended portion of the drive ribbon in the extended configuration defines a helix, the drive ribbon being incrementally movable from the retracted configuration to the extended configuration about a drive axis, wherein, in response to a movement of the drive ribbon from the retracted configuration to the extended configuration, the drive ribbon defines a transition portion disposed between the retracted portion and the extended portion, wherein along the transition portion the distal edge section and proximal edge section of the drive ribbon are not engaged together; and a drive member engaged with the drive ribbon to drivingly rotate the drive ribbon, the drive member being engaged with the retracted portion or the transition portion of the drive ribbon.

22. The device of aspect 21 wherein the drive member is a reciprocating drive member.

23. The device of aspect 22 wherein the reciprocating drive member engages a radially inward facing surface of the drive ribbon.

24. The device of aspect 22 wherein the reciprocating drive member is movable in a first direction and an opposite second direction, the reciprocating drive member including at least one flexible ratchet member engageable with the drive ribbon to allow a relative movement between the drive member and the drive ribbon in the first direction and to inhibit the relative movement between the drive member and the drive ribbon in the second direction.

25. The device of aspect 24 further including at least one stationary ratchet member fixed to the housing, including a plurality of ratchet members engaging a radially outward facing surface of the drive ribbon.

26. The device of aspect 21 wherein the drive member includes a worm gear engageable with the drive ribbon.

27. The device of aspect 21 wherein a storage bobbin for the retracted portion of the drive ribbon includes the drive member.

28. The device of any one of aspects 1-27 wherein the drive ribbon includes a plurality of sensor targets disposed at a predefined spacing along the drive ribbon, the device further comprising a sensor adapted to sense the sensor targets, wherein a sensed movement of the sensor targets past the sensor during operation of the drive ribbon toward the extended configuration is used to control the movement of the drive ribbon.

29. The device of aspect 28 wherein the sensor targets are disposed on the radially outward facing surface of the extended portion of the drive ribbon.

30. The device of aspect 28 wherein the sensor targets are disposed on the radially inward facing surface of the extended portion of the drive ribbon.

31. The device of any one of aspects 1-27 wherein the drive ribbon includes a plurality of projections disposed at a predefined spacing along the drive ribbon, the device further comprising a control member positioned adjacent the extended portion, the control member being selectively movable between a position that allows rotational passage of the projections past the control member and another position wherein the control member blocks passage of the projections and thereby stops the rotation and extension of the drive ribbon.

32. A medication delivery device for use with a container having a container body holding a medication and defining an outlet, the container includes a piston disposed within the container body wherein advancement of the piston within the container body expels medication through the outlet, the delivery device comprising: a housing adapted to couple with the container; and a drive assembly coupled with the housing and adapted to advance the piston within the container, wherein the drive assembly comprises: a drive ribbon having a distal edge section and a proximal edge section, the drive ribbon having a retracted configuration and an extended configuration, wherein a retracted portion of the drive ribbon in the retracted configuration defines a spiral and an extended portion of the drive ribbon in the extended configuration defines a helix, the drive ribbon being incrementally movable from the retracted configuration to the extended configuration, wherein movement of the drive ribbon from the retracted configuration to the extended configuration defines a drive axis; and a drive mechanism operably coupled with the drive ribbon, the drive mechanism defining a secondary axis parallel with the drive axis, the drive mechanism generating a force that is transferred to the drive ribbon to move the drive ribbon from the retracted configuration to the extended configuration.

33. The device of aspect 32 wherein the drive mechanism includes a spring aligned with the secondary axis, wherein in response to setting a dose the spring is in a tensioning configuration, wherein in response to a release of the spring from the tensioning configuration, the spring is operable to generate a force transferable to move the drive ribbon from the retracted configuration to the extended configuration.

34. The device of aspect 32 wherein the drive mechanism includes a plunger disposed along the secondary axis, wherein a linear translation of the plunger is configured to generate a force that is transferred to the drive ribbon to move the drive ribbon from the retracted configuration to the extended configuration.

35. The device of aspect 32 wherein the drive mechanism includes an electric motor drivingly coupled with an element disposed along the secondary axis, the electric motor configured to generate a force that is transferred to the drive ribbon to move the drive ribbon from the retracted configuration to the extended configuration.

36. The device of aspect 35 wherein the element disposed along the secondary axis is a drive shaft of the electric motor.

37. The device of any one of aspects 32-36 wherein the drive ribbon and the drive mechanism are disposed within the housing and the container is removably attachable to the housing.

38. The device of any one of aspects 32-37 wherein the drive mechanism is disposed within the housing, the device further comprising a cartridge housing, wherein the drive ribbon is disposed within the cartridge housing and the container is mounted on the cartridge housing, the cartridge housing being detachably securable to the housing.

39. The device of aspect 38 wherein the drive mechanism includes a spring aligned with the secondary axis, wherein in response to setting a dose, the spring is under a tension, wherein the spring is configured to generate a force when the tension is released that is transferred to the drive ribbon to move the drive ribbon from the retracted configuration to the extended configuration.

40. The device of aspect 38 wherein the drive mechanism includes an electric motor drivingly coupled with an element disposed along the secondary axis, the electric motor is configured to generate a force that is transferred to the drive ribbon to move the drive ribbon from the retracted configuration to the extended configuration.

41. The device of aspect 40 further comprising an electrical power source disposed within the cartridge housing, the electric power source operably coupled to the electric motor when the cartridge housing is secured to the housing to thereby power the electric motor.

42. The device of any one of aspects 32-41 wherein the housing is adapted to accommodate one of a plurality of cartridges, each of the cartridges including a cartridge housing with a drive ribbon being disposed within the cartridge housing and a container being mounted on the cartridge housing, each of the cartridges being interchangeably and detachably securable to the housing.

43. The device of aspect 38 wherein an electronic module is disposed on the housing, and a cartridge includes the cartridge housing and the drive ribbon, the cartridge further comprising a digital memory device, the electronic module being in communication with the digital memory device of the cartridge when coupled with the housing, wherein, after completing an injection procedure, the electronic module is configured to record data on the digital memory device related to the injection procedure.

44. The device of aspect 43 wherein the data recorded on the digital memory device includes data related to the volume of medication remaining in the container.

45. The device of any one of aspects 1-44 wherein the cartridge is disposable.

46. The device of aspect 42 wherein the drive mechanism includes an electric motor drivingly coupled with an element disposed along the secondary axis, the electric motor configured to generate a force that is transferred to the drive ribbon to move the drive ribbon from the retracted configuration to the extended configuration.

47. The device of aspect 46 wherein an electronic module is disposed on the housing, and each of the plurality of cartridges further comprises a digital memory device, the electronic module being in communication with the digital memory device of the cartridge when coupled with the housing, wherein, after completing an injection procedure, the electronic module is configured to record data on the digital memory device related to the injection procedure.

48. The device of aspect 47 wherein the drive ribbon includes a plurality of sensor targets disposed at a predefined spacing along the drive ribbon, and the device further comprising a sensor adapted to sense the sensor targets, whereby sensing a movement of the sensor targets past the sensor as the drive ribbon is extended is used to control movement of the drive ribbon to the extended configuration.

49. The device of aspect 48 wherein the sensor is supported by the housing and the sensor targets are disposed on the radially inward facing surface of the extended portion of the drive ribbon.

50. A medication delivery device for use with a container having a container body holding a medication and defining an outlet, the container includes a piston disposed within the container body wherein advancement of the piston within the container body expels medication through the outlet, the delivery device comprising: a housing adapted to couple with the container; and a drive assembly coupled with the housing and adapted to advance the piston within the container, wherein the drive assembly comprises: a drive ribbon having a distal edge section and a proximal edge section, the drive ribbon having a retracted configuration and an extended configuration, wherein a retracted portion of the drive ribbon in the retracted configuration defines a spiral and an extended portion of the drive ribbon in the extended configuration defines a helix, the drive ribbon being incrementally movable from the retracted configuration to the extended configuration to advance said piston within the container body, wherein movement of the drive ribbon from the retracted configuration to the extended configuration defines a drive axis, wherein one of the distal edge section and the proximal edge section defines a plurality of edge projections, and the other of the distal edge section and the proximal edge section defines a plurality of openings configured to receive corresponding edge projections in an interlocking manner when the drive ribbon is in the extended configuration.

51. The device of aspect 50, wherein a radially outward facing surface of the drive ribbon comprises a plurality of regularly spaced surface projections, each of the surface projections bounded by intersecting first and second grooves.

52. The device of aspect 51, wherein a portion of the surface projections overlaps one of the distal and proximal edge sections in a manner to extend over the other of the distal and proximal edge sections when the drive ribbon is in the extended configuration.

53. A medication delivery device, comprising: a drive module including a module housing, a motor disposed within the module housing, and a drive gear operably coupled to a shaft of the motor; a cassette including a cassette housing configured to couple to the module housing; the cassette including a container body holding a medication and defining an outlet, the cassette including a piston disposed within the container body; a drive ribbon incrementally axially extendable to advance the piston within the container body to expel medication through the outlet; and a thrust member including a driven gear element operably coupled with the drive gear, the thrust member engaged with the drive ribbon and movable to extend or retract the drive ribbon.

54. The device of aspect 53, wherein the cassette housing houses the drive ribbon and the thrust member.

55. The device of one of aspects 53-54, wherein the cassette housing includes at least one a power source to power the electric motor of the drive module and an electronics module disposed within the module housing and a memory containing data about a type of medication, a remaining volume of the medication, a date of manufacture, and/or a serial number, wherein the memory is in communication with the electronics module of the module housing when the cassette housing is attached to the module housing.

56. The device of any one of aspects 53-55, wherein the cassette housing includes an attachment feature to securely couple the cassette housing to the module housing.

57. The device of aspect 56, wherein the attachment feature is configured to allow the cassette housing to be selectively detached from the module housing.

58. The device of aspect 57, wherein the module housing includes a releasable latch to allow the cassette housing to be detached from the module housing.

59. The device of any one of aspects 53-58, wherein the cassette further comprises a collar axially disposed from the thrust member along the cassette housing, the collar including one or more axial ribs received by corresponding axial grooves defined by the drive ribbon.

60. The device of aspect 59, wherein the thrust member is disposed radially outside the drive ribbon, the thrust member including an internal thread engageable with a corresponding lateral grooves defined by the drive ribbon.

61. The device of any one of aspects 53-60, further comprising an electronics module in communication with an encoder sensor configured to detect a coded pattern defined by the drive ribbon in order to determine at least one of a type of medication, an original quantity of medication, angular position of drive ribbon, axial position of drive ribbon, speed of extension and/or retraction of drive ribbon, and stoppage of drive ribbon or in order to control movement of the drive ribbon.

What is claimed is:

1. A medication delivery device for use with a container having a container body holding a medication and defining an outlet, the container includes a piston disposed within the container body wherein advancement of the piston within the container body expels the medication through the outlet, the delivery device comprising:
    a housing adapted to couple with the container; and
    a drive assembly coupled with the housing and adapted to advance the piston within the container, wherein the drive assembly comprises:
    a drive ribbon having a distal edge section and a proximal edge section, the drive ribbon being movable between a retracted configuration and an extended configuration about a drive axis, wherein a retracted portion of the drive ribbon in the retracted configuration defines a spiral and an extended portion of the drive ribbon in the extended configuration defines a helix, wherein a part of the distal edge section and a part of the proximal edge section associated with the retracted portion of the drive ribbon are not interlocked, and a part of the distal edge section and a part of the proximal edge section associated with the extended portion of the drive ribbon are interlocked, and
    a thrust member engaged with the drive ribbon and rotatable relative to the drive ribbon and the housing, wherein, in response to the rotation of the thrust member, the drive ribbon is movable between the retracted configuration and the extended configuration without any rotation relative to the housing or the container.

2. The device of claim 1 wherein the thrust member is axially stationary.

3. A medication delivery device for use with a container having a container body holding a medication and defining an outlet, the container includes a piston disposed within the container body wherein advancement of the piston within the container body expels the medication through the outlet, the delivery device comprising:
    a housing adapted to couple with the container; and
    a drive assembly coupled with the housing and adapted to advance the piston within the container, wherein the drive assembly comprises:
    a drive ribbon having a distal edge section and a proximal edge section, the drive ribbon being movable between a retracted configuration and an extended configuration about a drive axis, wherein a retracted portion of the drive ribbon in the retracted configuration defines a spiral and an extended portion of the drive ribbon in the extended configuration defines a helix; and
    a thrust member engaged with the drive ribbon and rotatable relative to the drive ribbon and the housing, wherein, in response to the rotation of the thrust member, the drive ribbon is movable between the retracted configuration and the extended configuration without any rotation relative to the housing or the container, wherein the thrust member includes a helical thread engageable with the drive ribbon, the device further comprising a rotational restraint member rotationally fixed relative to the housing and engaged with the drive ribbon to prevent relative rotation between the extended portion of the drive ribbon and the rotational restraint member.

4. The device of claim 3 wherein one of the rotational restraint member and the extended portion of the drive ribbon defines an axially extending key and the other one of the rotational restraint member and the extended portion of the drive ribbon defines an axially extending keyway to accommodate said key.

5. The device of claim 4 wherein the rotational restraint member is disposed radially outside of the drive ribbon at an engagement location where the rotational restraint member is engaged with the drive ribbon to prevent rotation of the drive ribbon.

6. The device of claim 4 wherein the rotational restraint member is disposed radially inside of the drive ribbon at an engagement location where the rotational restraint member is engaged with the drive ribbon to prevent rotation of the drive ribbon.

7. The device of claim 4 wherein the helical thread of the thrust member is disposed radially outside of the drive ribbon at an engagement location where the helical thread is engaged with the drive ribbon.

8. The device of claim 7 wherein the thrust member is axially captured by the rotational restraint member.

9. The device of claim 4 wherein the helical thread of the thrust member is disposed radially inside of the drive ribbon at an engagement location where the helical thread is engaged with the drive ribbon.

10. A medication delivery device for use with a container having a container body holding a medication and defining an outlet, the container includes a piston disposed within the container body wherein advancement of the piston within the container body expels the medication through the outlet, the delivery device comprising:
  a housing adapted to couple with the container; and
  a drive assembly coupled with the housing and adapted to advance the piston within the container, wherein the drive assembly comprises:
  a drive ribbon having a distal edge section and a proximal edge section, the drive ribbon being movable between a retracted configuration and an extended configuration about a drive axis, wherein a retracted portion of the drive ribbon in the retracted configuration defines a spiral and an extended portion of the drive ribbon in the extended configuration defines a helix; and
  a thrust member engaged with the drive ribbon and rotatable relative to the drive ribbon and the housing, wherein, in response to the rotation of the thrust member, the drive ribbon is movable between the retracted configuration and the extended configuration without any rotation relative to the housing or the container, wherein, in response to the rotation of the thrust member, the thrust member is movable axially in a proximal direction and a distal end of the drive ribbon remains axially stationary, and wherein, to advance the piston within the container body, the thrust member and the extended portion of the drive ribbon are axially moved in a distal direction.

11. The device of claim 10 wherein the thrust member includes a helical thread engageable with the drive ribbon, the helical thread disposed radially outside of the drive ribbon at an engagement location where the helical thread is engaged with the drive ribbon, the device further comprising a rotational restraint member rotationally fixed relative to the housing and engaged with the drive ribbon to prevent relative rotation between the extended portion of the drive ribbon and the rotational restraint member.

12. The device of claim 10 wherein the thrust member includes a helical thread engageable with the drive ribbon, the helical thread disposed radially inside of the drive ribbon at an engagement location where the helical thread is engaged with the drive ribbon, the device further comprising a rotational restraint member rotationally fixed relative to the housing and engaged with the drive ribbon to prevent relative rotation between the extended portion of the drive ribbon and the rotational restraint member.

13. The device of claim 10 further comprising a drive spring, the drive spring being tensioned as the thrust member is rotated to extend the drive ribbon, wherein, in response to release of a tension of the drive spring, the drive spring is configured to axially advance the thrust member and the extended portion of the drive ribbon.

14. A medication delivery device comprising:
  a housing;
  a drive assembly coupled with the housing; and
  a container having a container body holding a medication and defining an outlet, wherein the container is removably coupled to the housing, the container includes a piston disposed within the container body wherein advancement of the piston within the container body expels the medication through the outlet,
  wherein the container body comprises a drive ribbon having a distal edge section and a proximal edge section, the drive ribbon having a retracted configuration and an extended configuration, wherein a retracted portion of the drive ribbon in the retracted configuration defines a spiral and an extended portion of the drive ribbon in the extended configuration defines a helix, wherein upon actuation of the drive assembly the drive ribbon is configured to be movable from the retracted configuration to the extended configuration to advance said piston within the container body, wherein the movement of the drive ribbon from the retracted configuration to the extended configuration defines a drive axis, wherein a radially outward facing surface of the drive ribbon comprises a plurality of regularly spaced surface projections, each of the surface projections bounded by intersecting first and second grooves.

15. The device of claim 14, wherein one of the distal edge section and the proximal edge section defines a plurality of edge projections, and the other one of the distal edge section and the proximal edge section defines a plurality of openings configured to receive corresponding edge projections of the plurality of edge projections in an interlocking manner when the drive ribbon is in the extended configuration.

16. The device of claim 14, wherein a portion of one of the distal and proximal edge sections in a one of the distal edge section and the proximal edge section in a manner to extend over the other one of the distal edge section and the proximal edge section when the drive ribbon is in the extended configuration.

17. The device of claim 14, wherein, when the drive ribbon is extended axially, the first grooves are extended in a helical shape and the second grooves are extended in an axial direction, wherein a driven member comprises a helical thread in engagement with one of the first grooves of the drive ribbon, and wherein the housing includes a plurality of axial ribs in engagement with the second grooves of the drive ribbon.

18. A medication delivery device, comprising:
- a drive module including a module housing, a motor disposed within the module housing, and a drive gear operably coupled to a shaft of the motor;
- a cassette including a cassette housing configured to couple to the module housing, the cassette including a container body holding a medication and defining an outlet, the cassette including a piston disposed within the container body;
- a drive ribbon having a helical portion that is axially extendable to advance the piston within the container body to expel the medication through the outlet; and
- a thrust member including a driven gear element operably coupled with the drive gear, the thrust member engaged with the drive ribbon and movable to axially extend or retract the helical portion of the drive ribbon without rotation of the helical portion relative to the container body.

19. The device of claim 18, wherein the cassette housing houses the drive ribbon and the thrust member.

20. The device of claim 18, wherein the cassette housing includes at least one power source to power the motor of the drive module and an electronics module disposed within the module housing and a memory containing data about a type of the medication, a remaining volume of the medication, a date of manufacture, and/or a serial number, wherein the memory is in communication with the electronics module of the module housing when the cassette housing is attached to the module housing.

21. The device of claim 18, wherein the cassette housing includes an attachment feature to securely couple the cassette housing to the module housing.

22. The device of claim 21, wherein the attachment feature is configured to allow the cassette housing to be selectively detached from the module housing.

23. The device of claim 22, wherein the module housing includes a releasable latch to allow the cassette housing to be detached from the module housing.

24. The device of claim 18, wherein the cassette further comprises a rotational restraint axially disposed from the thrust member along the cassette housing, the rotational restraint including one or more axial ribs received by corresponding axial grooves defined by the drive ribbon.

25. The device of claim 24, wherein the thrust member is disposed radially outside the drive ribbon, the thrust member including an internal thread engageable with a corresponding lateral grooves defined by the drive ribbon.

26. The device of claim 18, further comprising an electronics module in communication with an encoder sensor configured to detect a coded pattern defined by the drive ribbon in order to determine at least one of a type of the medication, an original quantity of the medication, an angular position of the drive ribbon, an axial position of the drive ribbon, a speed of extension and/or retraction of the drive ribbon, and stoppage of the drive ribbon or in order to control movement of the drive ribbon.

27. The device of claim 18, wherein the drive ribbon comprises a plurality of sensor targets disposed at a predefined spacing along the drive ribbon, and the module housing or the cassette further comprises an electronic module and a sensor in communication with the electronic module and adapted to sense the sensor targets, whereby sensing a movement of the sensor targets past the sensor as the drive ribbon is extended is used to detect data related to an injection procedure.

28. The device of claim 18, wherein the module housing is adapted to accommodate one of a plurality of cassettes, each of the cassettes being interchangeably and detachably securable to the module housing.

29. The device of claim 28, wherein the module housing comprises an electronic module, and the cassette further comprises a digital memory device, the electronic module being in communication with the digital memory device of the cassette when coupled with the module housing, wherein, after completing an injection procedure, the electronic module is configured to record data on the digital memory device related to the injection procedure.

* * * * *